(12) United States Patent
Akselrod et al.

(10) Patent No.: US 7,623,912 B2
(45) Date of Patent: Nov. 24, 2009

(54) METHOD, APPARATUS AND SYSTEM FOR CHARACTERIZING SLEEP

(75) Inventors: Solange Akselrod, Givat Shmuel (IL); Armanda Lia Baharav, Savyon (IL); Zvika Shinar, Binyamina (IL)

(73) Assignee: Ramot At Tel Aviv University Ltd., Tel-Aviv (IL)

( * ) Notice: Subject to any disclaimer, the term of this patent is extended or adjusted under 35 U.S.C. 154(b) by 769 days.

(21) Appl. No.: 10/528,456

(22) PCT Filed: Sep. 18, 2003

(86) PCT No.: PCT/IL03/00753

§ 371 (c)(1),
(2), (4) Date: Mar. 18, 2005

(87) PCT Pub. No.: WO2004/026133

PCT Pub. Date: Apr. 1, 2004

(65) Prior Publication Data

US 2006/0235315 A1 Oct. 19, 2006

Related U.S. Application Data

(60) Provisional application No. 60/439,029, filed on Jan. 10, 2003, provisional application No. 60/411,829, filed on Sep. 19, 2002.

(51) Int. Cl.
*A61B 5/04* (2006.01)
(52) U.S. Cl. .................................................. 600/513
(58) Field of Classification Search ................. 600/300, 600/513, 515, 517
See application file for complete search history.

(56) References Cited

U.S. PATENT DOCUMENTS 5,265,617 A * 11/1993 Verrier et al. ............... 600/517

(Continued)

FOREIGN PATENT DOCUMENTS

WO WO 2004/026133 4/2004

OTHER PUBLICATIONS

Shinar et al. "Automatic Detection of Slow-Wave-Sleep Using Heart Rate Variability", Computers in Cardiology, 28: 593-596, 2001.

(Continued)

*Primary Examiner*—George Manuel

(57) ABSTRACT

A method of determining sleep stages from signals of electrical activity recorded of a chest of a sleeping subject, the signals being measured over a plurality of epochs. The method comprising: (a) extracting a series of cardiac R-R intervals from the signals and obtaining a time-frequency decomposition from the series of cardiac R-R intervals; (b) using the time-frequency decomposition to determine at least one Slow-Wave-Sleep (SWS) period and at least one Non-SWS (NSWS) period; (c) from the at least one NSWS period, determining at least one sleep-onset (SO) period and a plurality of non-sleep periods; (d) extracting a plurality of electromyogram (EMG) parameters from a portion of the signals, the portion corresponds to a NSWS period other than the at least one SO period and other than the plurality of non-sleep period; (e) using the plurality of EMG parameters to determine at least one REM period thereby also to obtain also at least one light-sleep (LS) period defined as a NSWS period other than the SO periods, other than the non-sleep periods and other than the REM periods; thereby determining the sleep stages of the sleeping subject.

333 Claims, 26 Drawing Sheets

10

```
┌─────────────────────────────────┐
│              12                 │
│    Extracting a series of RRIs  │
└─────────────────────────────────┘
              │
┌─────────────────────────────────────────┐
│                  14                     │
│  Obtaining a time-frequency decomposition│
└─────────────────────────────────────────┘
              │
┌─────────────────────────────────────────┐
│                  16                     │
│  Determining SWS periods and NSWS periods│
└─────────────────────────────────────────┘
```

U.S. PATENT DOCUMENTS

| | | | |
|---|---|---|---|
| 5,797,840 A | | 8/1998 | Akselrod et al. |
| 5,902,250 A | * | 5/1999 | Verrier et al. ............... 600/515 |
| 2004/0073098 A1 | * | 4/2004 | Geva et al. ................. 600/300 |
| 2006/0235315 A1 | | 10/2006 | Akselrod et al. |

OTHER PUBLICATIONS

Official Action Dated Oct. 2, 2008 From the US Patent Office Re.: U.S. Appl. No. 10/528,456.

Baharav et al. "Fluctuations in Autonomic Nervous Activity During Sleep Displayed by Power Spectrum Analysis of Heart Rate Variability", Neurology, 45(6): 1183-1187, 1995. Abstract.

Berlad et al. "Power Spectrum Analysis and Heart Rate Variability in Stage 4 and REM Sleep: Evidence for State-Specific Changes in Autonomic Dominance", Journal of Sleep Research, 2(2): 88-90, 1993. Abstract.

Bonnet et al. "Heart Rate Variability: Sleep Stage, Time of Night, and Arousal Influences", Electroencephalography and Clinical Neurophysiology, 102: 390-396, 1997.

Monti et al. "Autonomic Control of the Cardiovascular System During Sleep in Normal Subjects", European Journal of Applied Physiology, 87: 174-181, 2002.

Penzel et al. "Systematic Comparison of Different Algorithms for Apnoea Detection Based on Electrocardiogram Recordings", Medical & Biological Engineering & Computing, 40: 402-407, 2002.

Scholz et al. "Vegetative Background of Sleep: Spectral Analysis of the Heart Rate Variability", Physiology & Behavior, 62(5): 1037-1043, 1997.

Shinar et al. "Autonomic Changes During Wake-Sleep Transition: A Heart Rate Variability Based Approach", Autonomic Neuroscience: Basic and Clinical, 11P., 2006.

Shinar et al. "R Wave Duration as A Measure of Body Position Changes During Sleep", Computers in Cardiology, 26: 49-52, 1999.

Van De Borne et al. "Effects of Wake and Sleep Stages on the 24-h Autonomic Control of Blood Pressure and Heart Rate in Recumbent Men", American Journal of Physiology, Heart Circulation Physiology, 266(35): H548-H554, 1994.

* cited by examiner

10

```
┌─────────────────────────────┐
│ 12                          │
│ Extracting a series of RRIs │
└─────────────────────────────┘
              │
┌─────────────────────────────────────┐
│ 14                                  │
│ Obtaining a time-frequency decomposition │
└─────────────────────────────────────┘
              │
┌──────────────────────────────────────┐
│ 16                                   │
│ Determining SWS periods and NSWS periods │
└──────────────────────────────────────┘
```

```
┌──────────────────────────┐
│ 22                       │
│ Extracting EMG parameters │
└──────────────────────────┘
              │
┌──────────────────────────────────────┐
│ 24                                   │
│ Determining REM periods and NREM periods │
└──────────────────────────────────────┘
```

```
┌─────────────────────────────┐
│ 32                          │
│ Extracting a series of RRIs │
└─────────────────────────────┘
              │
┌──────────────────────────────────────────┐
│ 34                                       │
│ Constructing a Poincare plot from the RRI series │
└──────────────────────────────────────────┘
              │
┌──────────────────────────────────────┐
│ 36                                   │
│ Determining REM periods and NREM periods │
└──────────────────────────────────────┘
```

Fig. 3

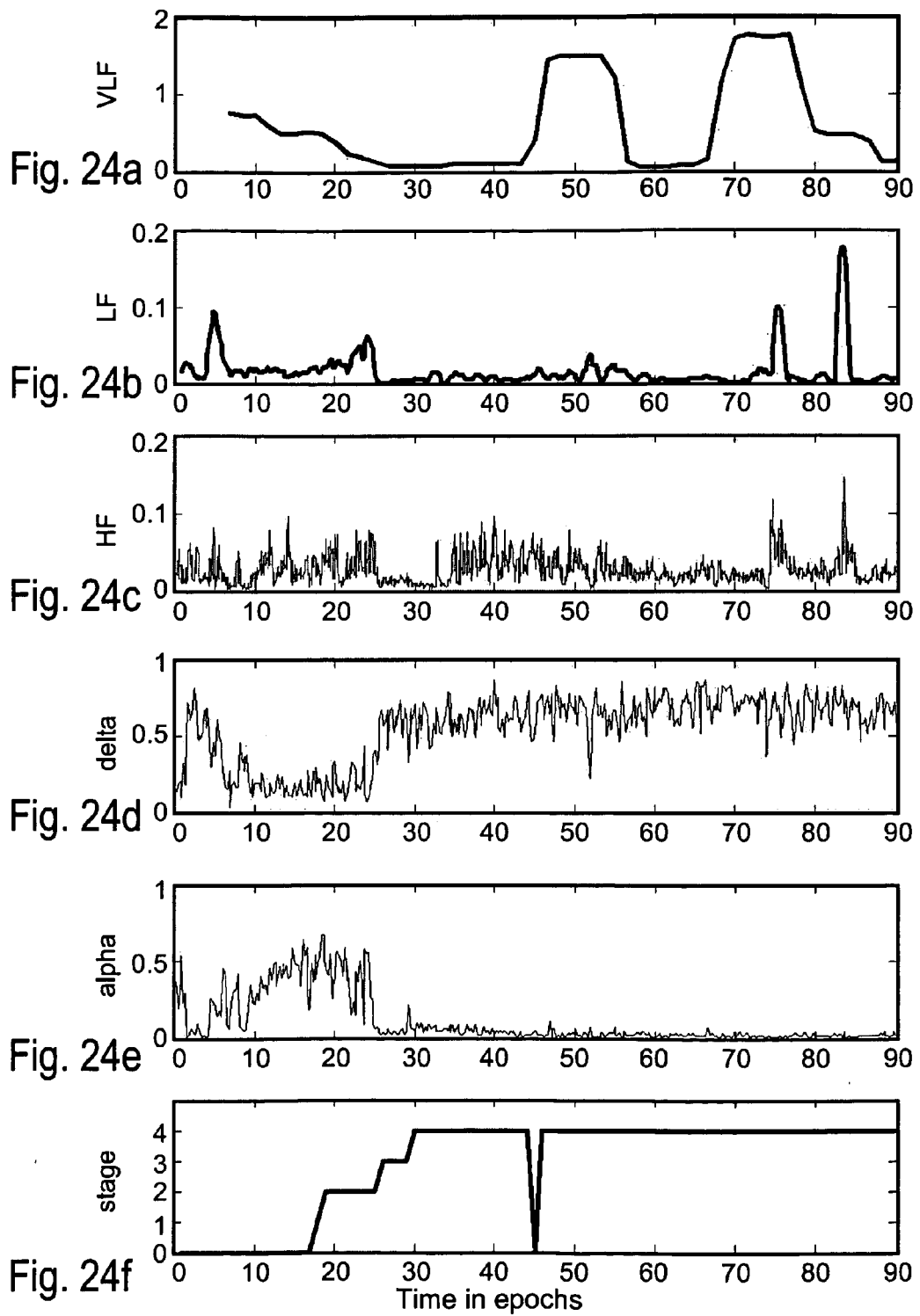

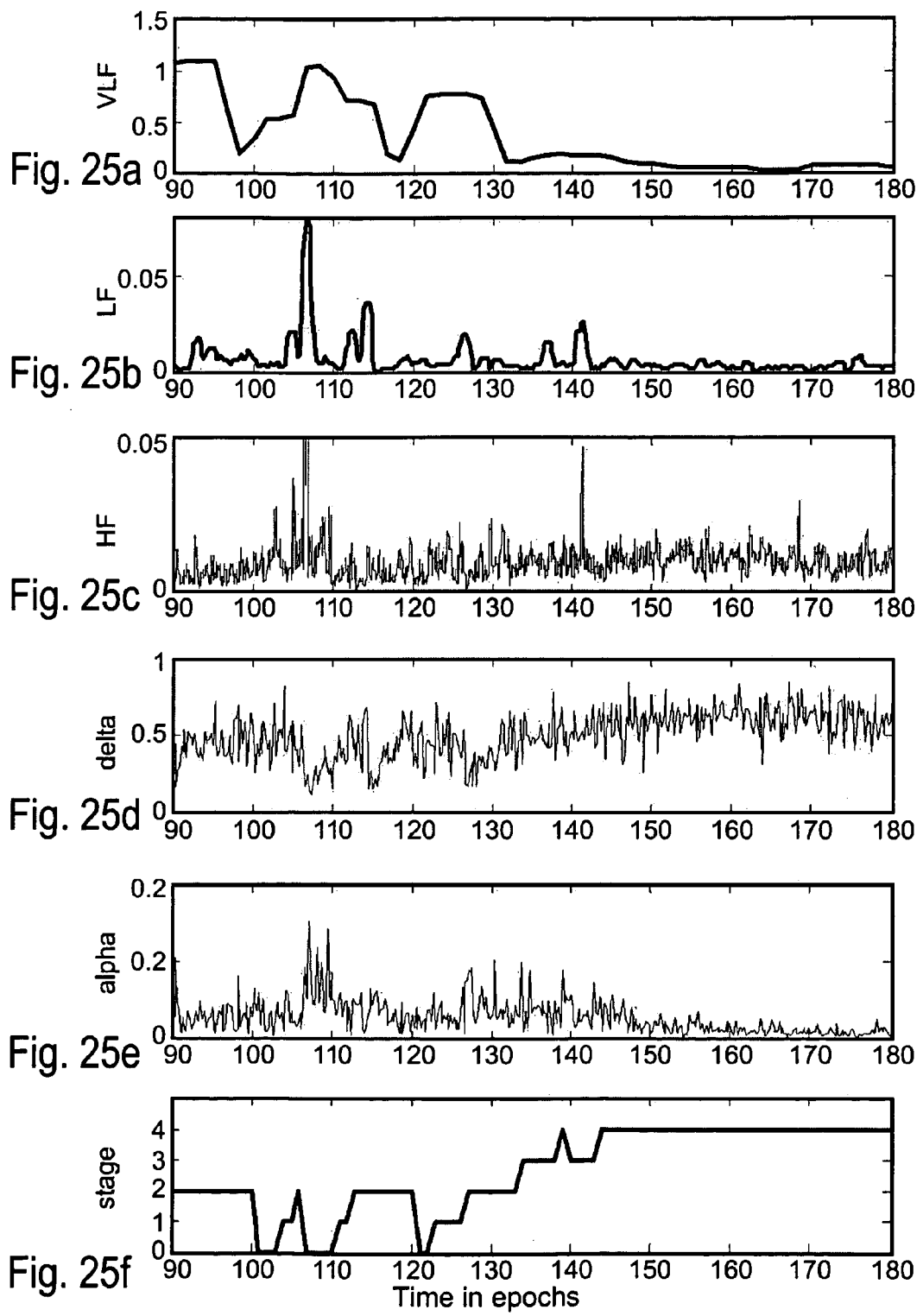

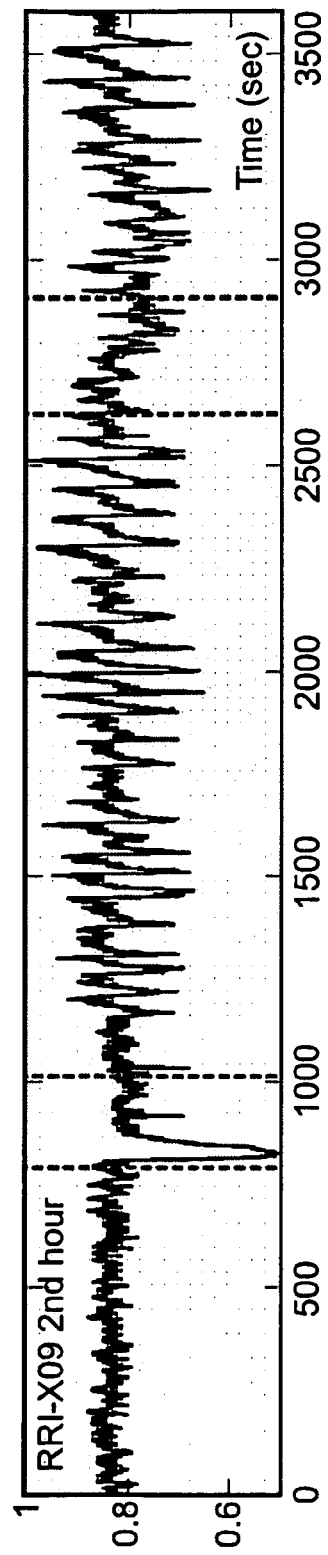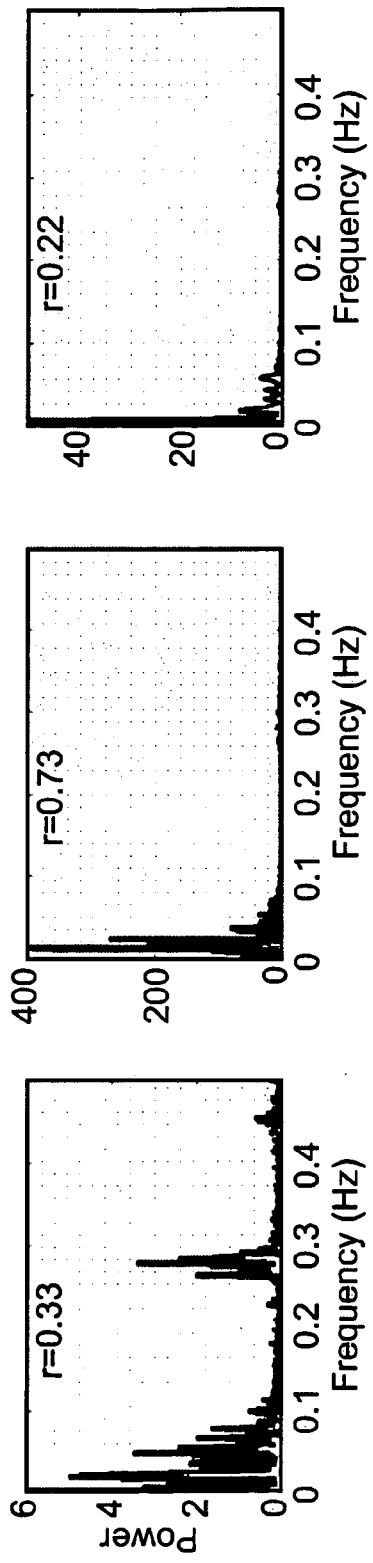
Fig. 38a
Fig. 38b
Fig. 38c
Fig. 38d

METHOD, APPARATUS AND SYSTEM FOR CHARACTERIZING SLEEP

RELATED PATENT APPLICATION

This application is a National Phase Application of PCT/IL03/00753 having International Filing Date of 18 Sep. 2003, which claims priority from U.S. Provisional Patent Application No. 60/411,829 filed 19 Sep. 2002 and from U.S. Provisional Patent Application No. 60/439,029 filed 10 Jan. 2003.

FIELD AND BACKGROUND OF THE INVENTION

The present invention relates to methods, apparati and systems for characterizing sleep and, more particularly, to methods, apparati and systems for an efficient determination of sleep stages, body positions and/or sleep disorders of a sleeping subject, using only data derived from signals of electrical activity recorded of a chest of a sleeping subject, such as electrocardiogram (ECG) signals, reflecting cardiac electrical activity, and signals inherently associated with ECG signals, reflecting autonomic nervous system activity and electrical activity of muscles, other than the heart muscle itself, present in the chest of the sleeping subject.

The growing interest in sleep and its disorders, including their influence on health, well-being and public safety (such as in car accidents) have caused a continuously increasing need to perform sleep investigations for both research and clinical purposes. Substantial research has been undertaken directed toward understanding the nature of sleep and of sleep disorders. These researches yielded considerable information concerning human patterns of sleep and wakefulness, and of physiological activities occurring during human sleep. In addition, substantial information has been obtained concerning various sleep disorders.

It is common to divide the sleep of a normal healthy individual into a succession of three states of being, known as Wakefulness, Rapid-Eye-Movement (REM) sleep and Non-REM (NREM) sleep. NREM sleep is subdivided into four sleep stages, which are enumerated from Stage1 to Stage-4 according to the increasing threshold to the influence of external stimuli, these stages are also known as the depth of sleep.

NREM and REM sleep alternate throughout the night in cycles: each sleep cycle lasts about 90-120 minutes; normally each cycle starts with NREM followed by REM. The night contains 4-5 sleep cycles, where, within each cycle along the night, the relative duration of REM sleep increases and the relative duration of NREM decreases. Altogether, the period of NREM sleep represents more than 60% of the night sleep and REM around 30%. Normally, REM sleep first occurs about 90 minutes after sleep-onset (beginning of Stage-1), at the end of the first sleep cycle. This first REM period is short and might be easily overlooked. Each subsequent cycle lasts approximately the same time with shorter and lighter stages of NREM and extending REM periods as the night goes on. Thus, towards morning hours sleep becomes lighter (longer stage 2) and individuals dream more (longer REM). A person may complete between four and six cycles in a typical night's sleep. The overall percentage of the duration of NREM stages and the REM stage is typically about 70% of NREM and about 30% of REM in a healthy adult person.

The percentage of REM sleep is highest during infancy and early childhood, drops off during adolescence and young adulthood, and remains stable thereafter. Total sleep time is longest during early infancy (newborns sleep about 18 hour a day) and sleep times decreases gradually to normal adult values, around 8 hours a night. Paradoxically, the sleep needs during adolescence are increased while the social and curricular needs at this age cause sleep deprivation. In the old age sleep needs do not change, however the ability to sleep is somewhat reduced. NREM sleep becomes lighter, REM remains stable at about 25-30% of total sleep time, the sleep latency increases, and generally sleep is more fragmented than in younger individuals. Monitoring an individual's sleep pattern is crucial for diagnosing sleep disorders, follow up results of treatment of sleep disturbances, and conducting research in the field of sleep.

To date, sleep stages are monitored and examined clinically with a polysomnograph (PSG), which provides data regarding the electrical activity of brain, muscles and eye movement during sleep. The PSG data are analyzed according to a gold standard procedure attributed to Rechtschaffen and Kales (R&K) [Rechtschaffen A., Kales A., eds., "A manual of standardized terminology, techniques and scoring system for sleep staging in human subjects", Washington D.C.: US Government Printing Office, NIH Publication 204, 1968]. The R&K criteria are primarily based on the analysis of three collected bio-signals: (i) electroencephalogram (EEG), (ii) electrooculogram (EOG), and (iii) electromyogram (EMG). The standard procedure is as follows: EEG signals are derived primarily from the cortex of the brain. At the same time an EMG signal which monitors muscle activity, generally from one of the muscles of the mandible (submental) is measured, together with left eye and right eye EOG (signals produced by eyeball movements relative to the skull). These EEG, EMG and EOG signals are conventionally recorded on a multi-channel physiological recorder.

The number of physiologic inputs which are required in the PSG procedure may vary. Specifically, the monitored signals include EEG (2-4 leads), EOG (2 leads), EMG (chin and limbs; 1-3 or more leads), airflow, respiratory effort (1-2 leads), oxygen saturation, electrocardiogram (ECG), body position and a microphone. Data is stored during the sleep, and the analysis is typically done off-line, according to the standard R&K criteria.

For Stage-1 sleep, which is often considered to be first in the sequence (in models where waking is not included), there is some slowing in EEG frequency, the brain activity is similar to that of wakefulness, there is a slow rolling eye movements and a certain decrease in EMG amplitude. The eyes are closed during Stage-1 sleep, but if aroused from it, a person may feel as if he or she has not slept. Stage-1 usually lasts a few minutes.

Stage-2 is a period of light NREM sleep during which PSG readings are characteristic. EEG signal displays Sleep spindles and biphasic waves-K complexes, EOG signals shows no eye movements in normal subjects free of pharmacological treatments and the EMG signal amplitude is lower than during wakefulness. K-complexes are spontaneous and can be induced by means of sudden auditory stimuli. The heart rate slows, and body temperature decreases. At this point, the body prepares to enter deep sleep. Stages-1 and -2 are collectively known as Light Sleep (LS).

Stages-3 and -4 are deep sleep stages, with Stage-4 being more intense than Stage-3. These stages are known as Slow-Wave-Sleep (SWS). During SWS, especially during Stage-4, the EEG is characterized by slow waves of high amplitude and pattern synchronization. EOG shows no eye movements and the EMG amplitude is significantly lower than during wakefulness.

REM sleep is distinguishable from NREM sleep by changes in physiological states, including its characteristic Rapid-Eye-Movements. However, EEG signal shows wave patterns in REM to be similar to Stage-1 sleep and wakefulness with mixed frequencies and low amplitude desynchronized activity. The eye movements are rapid and similar to the wakefulness eye movements. The skeletal, weight bearing muscles become atonic—the EMG amplitude is extremely low. During normal REM sleep, heart rate and respiration speed up and become erratic, while the face, fingers and legs may twitch. Intense dreaming occurs during REM sleep and there is increased metabolism in certain brain regions. Paradoxically, paralysis occurs simultaneously in the major voluntary muscle groups and the muscles of the upper airways. It is generally thought that REM-associated muscle paralysis is meant to keep the body from acting out the dreams that occur during this stage.

The waking stage is referred to as relaxed wakefulness, during this time period, which varies according to the environmental conditions and individual's characteristics the body prepares for sleep. Normally, as a person becomes sleepier, the body begins to slow down. Muscles begin to relax, and eye movement slows to a roll and the responsiveness to external stimuli decreases steeply with sleep onset.

During sleep the muscles of the upper part of the throat relax. For healthy individual, the upper part of the throat remains open enough to permit the flow of air into the lungs. Some individuals, however, suffer from increased upper airway resistance.

Several sleep disorders and symptoms are associated with increased upper airway resistance, for example, snoring and obstructive apnea. The ability to maintain upper airway patency during the normal respiratory cycle is the result of a delicate equilibrium between the forces that promote airway closure and dilation. Factors predisposing upper airway obstruction include anatomic narrowing, abnormal mechanical linkage between airway dilating muscles and airway walls, muscle weakness, and abnormal neural regulation.

Despite the misleadingly benign clinical presentation, the pathological consequences of sleep apnea, especially in children, may be severe, and some pathological consequences are still being uncovered. Several immediate consequences of upper airway obstruction during sleep are recognized. These include, sleep fragmentation, increased work of breathing, alveolar hypoventilation and intermittent hypoxemia.

Many sleep disorders, in particular snoring, sudden infant death syndrome and obstructive sleep apnea syndrome, are position-dependent. Knowing the body position during sleep is important for study, diagnosis and treatment strategy of such sleep disorders.

Other disorders or disturbances are also related to frequent body position changes during sleep.

Quality of sleep, which is closely related to the amount of body position changes [De Koninck J. et al., "Sleep positions in the young adult and their relationship with the subjective quality of sleep", 1983, *Sleep,* 6: 52]. Pulmonary blood flow, which was suggested to be influenced by gravity, and its distribution was shown to depend on body posture [Hakim T. S. et al., "Effect of body posture on spatial distribution of pulmonary blood flow", *J Appl Physiol.,* 1988, 64(3):1160-70].

Very recently, a connection was found between sleep position and kidney stones [Bijan S., Lu A. F., and Stoller M. L., "Correlation of unilateral urolithiasis with sleep posture" *The J. Urol.,* 2001, 165:1085-1087].

Furthermore, in ST monitoring and other ECG-based applications, where measurements of ECG segments are relevant (e.g. ischemia), movement of the subject is considered artifact [Adams M. G., Drew B. J., "Body position effects on the ECG-implication for ischemia monitoring", 1997, *J elec-* *trocard,* 30:285-291]. Knowing changes in the body position may be of advantage so as to screen out movement artifacts.

Hence, in addition to the above physiologic inputs, a standard whole night PSG procedure often includes body position monitoring, for example, using specific sensors or visual means, such as a video camera. Determination of body position during sleep may also assists in diagnosing sleep disorders originating from frequent body position changes during sleep.

Whether or not the body position monitoring is included, the PSG procedure is uncomfortable for the subject, artifacts in the acquired signals are very frequent and cause difficulties in data interpretation with the need to redo the study or to increase greatly the time required for the interpretation. Automatic data scoring, although available, is generally not very reliable. Thus, often an expert is reviewing the acquired data and analyses/scores it epoch by epoch. This manual data interpretation is cumbersome and tinted with subjectivity. Standard sleep studies are thus expensive and cumbersome, their reliability is often limited, especially when the data collected is of bad quality and the interpretation is automatic. In addition, the sleep of the subject is influenced by both the requirement to sleep in the laboratory and the multitude of sensors used, which leads to an undesired effect of a measurement influencing the results of the measurement.

It is recognized that sleep is accompanied by cardiocirculatory changes which are a direct consequence of alterations in the autonomic nervous system (ANS). Broadly speaking, during sleep parasympathetic activity is increased while sympathetic activity decreases with phasic activations-deactivations in REM sleep [Parmeggiani P. L. and Morrison A. R., "Alterations in human functions during sleep", *Central Regulation of Autonomic Functions,* Lowey A. D. and Spyer K. M., eds., Oxford University Press, 1990, 367].

Recently, analysis of ECG signals in general and Heart-Rate-Variability (HRV) in particular, have been used to quantify the behavior of the ANS, thereby to characterize different sleep stages using different ANS behavior [Berlad I, Shlitner A, Ben-Haim S, Lavie P. "Power spectrum analysis and heart rate variability in stage 4 and REM sleep: Evidence for state specific changes in autonomic dominance", *J. Sleep Res.* 1993, 2:88; Baharav et al. "Fluctuations in autonomic nervous activity during sleep displayed by power spectrum analysis of heart rate variability", *Neurology* 1995, 45:1183; Bonnet M. H., and Arand, D. L., "Heart rate variability: sleep stage, time of night, and arousal influence", *EEG Cli. Neurophy* 1997, 102:390; Scholtz U. J., Bianchi A. M., Cerutti S, Kubicki S., "Vegetative Background of Sleep: Spectral Analysis of the Heart Rate Variability" *Physiol Behav,* 1997, 62:1037; Baharav A., Shinar Z., Sivan Y., Toledo E., Keselbrener L., and Akselrod S., "Autonomic changes associated with sleep onset investigated by time-frequency decomposition of heart rate variability", *Sleep* 1998, 21:208; Monti A, Medigue C, Nedelcoux H, Escourrou P., "Autonomic control of the cardiovascular system during sleep in normal subjects" *Eur J Appl Physiol,* 2002, 87:174].

The ANS plays a cardinal role in the control of cardiovascular function. Heart rate (HR), heart excitability and contractility are under the constant influence of the parasympathetic-sympathetic balance. Parasympathetic nerves and sympathetic fibers innervate the Sino-Atrial (SA) node; the parasympathetic influence is inhibitory while the sympathetic influence is excitatory. The parasympathetic fibers to the SA node are driven by inhibitory and excitatory inputs from peripheral receptors (baroreceptors, chemoreceptors, cardiac, pulmonary and airway receptors). Behavioral adaptive influence of the heart rate at the sinus node is mediated by supramedullary inputs to the cardiovagal neurons. The origin of the sympathetic innervation of the heart is located at the T2-T5 segment of the spinal cord and the preganglionic fibers synapse in the cervical ganglia; the post synaptic ganglionic fibers innervate the SA node (predominantly Right sympathetics increase HR) as well as the Atrio-Venticular (AV) node (predominantly Left sympathetics—increase AV conduction and cardiac contractility).

Normal cardiac function is regulated by the complex balance of the sympathetic and parasympathetic outflows to the heart. This balance is also responsible for the susceptibility to arrhythmias: while vagal activity has a protective role, sympathetic activity lowers the threshold to ventricular fibrillation. Normal heart function, heart rate included, is modulated by the fluctuations in the sympathetic and parasympathetic flow to the heart. These fluctuations induce beat-to-beat variability in heart rate and arterial pressure. Hence, the analysis of the instantaneous fluctuations in cardiovascular variables supplies valuable information on the autonomic control in an intact organism.

The early methods of analysis of HRV to study the ANS employed algorithms based on Fast-Fourier-Transform (FFT) [Akselrod et al. "Power spectrum analysis of heart rate fluctuations: a quantitative probe of beat to beat cardiovascular control", *Science* 1981, 213:220] and autoregressive methods [Malliani et al. "Cardiovascular neural regulation explored in the frequency domain", *Circulation*, 1991, 84:482]. These pioneer methods require stationary signals for a relatively long time period, hence allow for estimation of the autonomic function under steady state conditions. However, it has been realized that spreading eventual time-dependent changes in frequency content over the entire time window, results in obscuring any insight into the time axis within the trace length.

To overcome the non physiologic assumption of stationary conditions, new mathematical methods have been developed. Their quantitative description is based on the use of time-frequency spectral decomposition of the simultaneous HR, blood pressure (BP) and respiratory signals. A sequential estimation of power spectra, such as the use of a time shifted short time Fourier transform [Nawab S. H. and Quatieri T. F., "Short-Time Fourier Transform", *Advanced Topics in Signal Processing*, Lim and Oppenheim, eds, Englewood Cliffs, N.J., Prentice Hall 1988, 289] represents the most straightforward attempt to overcome this limitation. However it suffers from the intrinsic compromise, which involves its loss in time resolution within the power spectrum of each sub-trace, as well as its severe limitation regarding the minimum frequency it can focus on.

Various approaches have been recently developed in order to overcome these limitations (to this end see, e.g., a review by Cohen L., entitled "Time-frequency distributions" and published in *Proc. IEEE* 1989, 77:941). These approaches include, Selective Discrete Algorithm (SDA) [Keselbrener L and Akselrod S. "Selective discrete Fourier transform algorithm for time-frequency analysis: Methods and application on simulated and cardiovascular signals" *IEEE Trans. Biomed. Eng.* 1996, 43:789], modified Wigner-Ville [Novak P and Novak V, "Time-frequency Mapping of the Heart Rate, Blood Pressure and Respiratory Signals", *Medical & Biological Engineering and Computing*, 1993, 31:103], time-dependent autoregression [Bianchi et al., "Time-Variant Power Spectrum Analysis for the detection of Transient episode in HRV Signals", *IEEE Transactions on Biomedical Eng.*, 1993, 40: 136], and Wavelets [Meyer Y., "Wavelets: Algorithms and applications", Ed. SIAM, Philadelphia 1993].

The above studies were primarily aimed at investigating autonomic activity (in steady and non-steady conditions) using HRV analysis, and when focusing on sleep, previous studies were primarily directed at investigating sleep physiology by means of HRV analysis. However, prior art methods fail to exploit HRV for the purpose of scoring sleep, in general, and determining the various sleep stages in particular.

There is thus a widely recognized need for, and it would be highly advantageous to have, a method, apparatus and system for determining sleep stages of a subject, based on data derived solely from electrical signals recorded of a chest of a sleeping subject, and devoid of the limitations associated with prior art methodologies.

SUMMARY OF THE INVENTION

According to one aspect of the present invention there is provided a method of determining a Slow-Wave-Sleep (SWS) period and a Non-SWS (NSWS) period from signals of electrical activity recorded of a chest of a sleeping subject, the signals being measured over a plurality of epochs, the method comprising: extracting a series of cardiac R-R intervals from the signals and obtaining a time-frequency decomposition from the series of cardiac R-R intervals; and using the time-frequency decomposition to determine the SWS period; thereby determining the SWS period and the NSWS period of the sleeping subject.

According to another aspect of the present invention there is provided a method of determining a Rapid-Eye-Movement (REM) sleep and a Non-REM (NREM) sleep from signals of electrical activity recorded of a chest of a sleeping subject, the signals being measured over a plurality of epochs, the method comprising: extracting a plurality of electromyogram (EMG) parameters from the signals; and using the plurality of EMG parameters to determine at least one REM period; thereby determining the REM sleep and the NREM sleep of the sleeping subject.

According to yet another aspect of the present invention there is provided a method of determining a REM sleep and an NREM sleep from signals of electrical activity recorded of a chest of a sleeping subject, the signals being measured over a plurality of epochs, the method comprising: extracting a series of cardiac R-R intervals from the signals; constructing a Poincare plot of the series of cardiac R-R intervals; and using the Poincare plot to determine the REM sleep and the NREM sleep of the sleeping subject.

According to further features in preferred embodiments of the invention described below, the method further comprising calculating a plurality of moments with respect to a predetermined line along the Poincare plot, each of the plurality of moments being calculated within a predetermined time-window.

According to still further features in the described preferred embodiments the REM sleep is defined by a plurality of epochs, each characterized by a moment which is below a predetermined threshold.

According to still further features in the described preferred embodiments the method further comprising normalizing each of the plurality of moments.

According to still another aspect of the present invention there is provided a method of determining sleep stages from signals of electrical activity recorded of a chest of a sleeping subject, the signals being measured over a plurality of epochs, the method comprising: extracting a series of cardiac R-R intervals from the signals and obtaining a time-frequency decomposition from the series of cardiac R-R intervals; using the time-frequency decomposition to determine at least one SWS period and at least one NSWS period; from the at least one NSWS period, determining at least one sleep-onset (SO) period and a plurality of non-sleep periods; extracting a plurality of EMG parameters from a portion of the signals, the portion corresponds to a NSWS period other than the at least one SO period and other than the plurality of non-sleep period; using the plurality of EMG parameters to determine at least one REM period thereby obtaining also at least one light-sleep (LS) period defined as a NSWS period other than the at least one SO period, other than the plurality of non-sleep periods and other than the at least one REM period; thereby determining the sleep stages of the sleeping subject.

According to further features in preferred embodiments of the invention described below, the method further comprising determining, from the at least one LS period, at least one Stage-2 period thereby obtaining also a Stage-1 period, the Stage-1 period being defined as a LS period other than the at least one Stage-2.

According to still further features in the described preferred embodiments the obtaining the time-frequency decomposition comprises calculating, for each epoch, at least one time-dependent power spectrum component selected from the group consisting of a very-low-frequency (VLF) power spectrum, a low-frequency (LF) power spectrum and a high-frequency (HF) power spectrum.

According to still further features in the described preferred embodiments the SWS period is defined by a plurality of epochs, each characterized by at least one power parameter which is below a predetermined threshold, the at least one power parameter is selected from the group consisting of the VLF power spectrum, the LF power spectrum, the HF power spectrum, and a combination between two of the VLF, the LF and the HF power spectra.

According to still further features in the described preferred embodiments at least one of the VLF, the LF and the HF power spectra are calculated within a window along the series of cardiac R-R intervals, the window being characterized by a duration which is a function of a respective frequency.

According to still further features in the described preferred embodiments the method further comprising determining a frequency resolution.

According to still further features in the described preferred embodiments the frequency resolution is from 0.001 Hz to 0.03 Hz.

According to still further features in the described preferred embodiments the method further comprising determining a time resolution.

According to still further features in the described preferred embodiments the time resolution is from 1 second to 30 seconds.

According to still further features in the described preferred embodiments the method further comprising determining an onset and a termination of the time-dependent power spectra.

According to still further features in the described preferred embodiments at least one of the VLF, the LF and the HF power spectra are calculated by a wavelet transform.

According to still further features in the described preferred embodiments the wavelet transform is selected from the group consisting of a discrete wavelet transform and a continuous wavelet transform.

According to still further features in the described preferred embodiments at least one of the VLF, the LF and the HF power spectra are calculated by a selective discrete spectral transform.

According to still further features in the described preferred embodiments the selective discrete spectral transform is selected from the group consisting of: a Fourier transform, a Haar transform, a Hartley transform, a sine transform, a cosine transform, and a Hadamard transform.

According to still further features in the described preferred embodiments the determining at least one SO period comprises calculating at least one SO parameter and defining the SO period to be at least one epoch being characterized by at least one SO parameter which is above a predetermined threshold, over a predetermined time range.

According to still further features in the described preferred embodiments the method further comprising calculating the predetermined frequency limits.

According to still further features in the described preferred embodiments the calculating the predetermined frequency limits comprises obtaining a steady state power spectrum from series of cardiac R-R intervals, and applying a minimum-cross-entropy method on the steady state power spectrum, so as to provide the frequency limits.

According to still further features in the described preferred embodiments the minimum-cross-entropy method is executed so as to separate between frequency peaks of the steady state power spectrum.

According to still further features in the described preferred embodiments the method further comprising normalizing the at least one SO parameter.

According to still further features in the described preferred embodiments the method further comprising analyzing the at least one SO parameter using a plurality of statistical quantities.

According to still further features in the described preferred embodiments the method further comprising: (a) filtering the series of cardiac R-R intervals using a low-pass-filter, thereby providing a first series of signals; and (b) defining the at least one awakening period as a plurality of epochs each associated with at least one of the first series of signals which is below a predetermined threshold.

According to still further features in the described preferred embodiments the low-pass-filter is at about 0.01 Hz.

According to still further features in the described preferred embodiments the method further comprising: (a) filtering the series of cardiac R-R intervals using a band-pass-filter, thereby providing a second series of signals; and (b) defining the at least one arousal period as a plurality of epochs each associated with at least one of the second series of signals which is below a predetermined threshold.

According to still further features in the described preferred embodiments the extracting a plurality of EMG parameters is effected by at least one procedure selected from the group consisting of: eliminating P waves, eliminating T waves and eliminating QRS-complexes from the signals.

According to still further features in the described preferred embodiments the eliminating P waves and the eliminating T waves from the signals is by high pass filtering.

According to still further features in the described preferred embodiments the high pass filtering is at a threshold frequency of about 10 Hz.

According to still further features in the described preferred embodiments the eliminating QRS-complexes is by a combination of gating and/or subtraction.

According to still further features in the described preferred embodiments the REM sleep is defined by a plurality of epochs, each characterized by at least one of the plurality of EMG parameters which is below a predetermined threshold.

According to still further features in the described preferred embodiments the at least one Stage-2 period is defined by a plurality of epochs, each associated to a cardiac R-R interval corresponding to a K-complex.

According to still another aspect of the present invention there is provided a method of determining a body position or a change in the body position from signals of electrical activity recorded of a chest of a sleeping subject, the signals being characterized by QRS complexes, the method comprising: extracting R-wave durations from the QRS complexes, thereby obtaining an R-wave duration (RWD) function; and using the RWD function to determine the body position or the change in the body position of the sleeping subject.

According to still further features in the described preferred embodiments the change in the body position is defined when a change of the RWD function is above a predetermined threshold.

According to still further features in the described preferred embodiments the change of the RWD function is calculated using at least one local average of the RWD function.

According to still further features in the described preferred embodiments the change of the RWD function is defined as a difference between two local averages of the RWD function.

According to still further features in the described preferred embodiments the two body positions, comprise a first body position, defined when a value of the RWD function is high and a second body position, defined when a value of the RWD function is low.

According to still further features in the described preferred embodiments the method further comprises defining at least two segments of each of the QRS complexes and determining width of each of the at least two segments, thereby obtaining, for each QRS complex, a set of widths, the set being representative of the body position.

According to still further features in the described preferred embodiments each of the segments has a first endpoint and a second endpoint, the first and the second endpoints being characterized by a zero nth-order derivative of a respective R-wave of the QRS complex, where n is a positive integer.

According to still further features in the described preferred embodiments the four body positions comprise: a first body position, defined when a value of the left segment is high and a value of the right segment is high; a second body position, defined when a value of the left segment is low and a value of the right segment is high; a third body position, defined when a value of the left segment is high and a value of the right segment is low; and a fourth body position, defined when a value of the left segment is low and a value of the right segment is low.

According to still further features in the described preferred embodiments the method further comprises applying a clustering procedure on each the sets of widths, so as to define a plurality of clusters, each one of the plurality of clusters corresponding to a different body position.

According to still further features in the described preferred embodiments the clustering procedure is selected from the group consisting of graph theory procedure, density estimation procedure, Potts-spins-based procedure, hierarchical procedure and partitional procedure.

According to still further features in the described preferred embodiments the partitioned procedure is selected from the group consisting of a K-means procedure, an adaptive K-means procedure, hard C-means procedure and fuzzy C-means procedure.

According to still further features in the described preferred embodiments the hierarchical procedure is selected from the group consisting of a nearest neighbor procedure and a minimal spanning tree procedure.

According to still another aspect of the present invention there is provided a method of characterizing a sleep of a sleeping subject, the method comprising: calculating at least one autonomic balance index (ABI), each corresponding to a different sleep stage of the sleeping subject and being calculated using a weight of the sleep stage and at least one power parameter; and using the at least one ABI for characterizing the sleep of the sleeping subject.

According to still further features in the described preferred embodiments if one or more of the at least one ABI is larger than a predetermined threshold then determining an obstructive sleep apnea for the sleeping subject.

According to still further features in the described preferred embodiments the method further comprises summing the at least two ABIs thereby obtaining a total ABI.

According to still further features in the described preferred embodiments if the total ABI is larger than a predetermined threshold then determining an obstructive sleep apnea for the sleeping subject.

According to still further features in the described preferred embodiments the method further comprises determining periods of the SWS using time-frequency decomposition of the series of cardiac R-R intervals.

According to still further features in the described preferred embodiments the method further comprises determining periods of the REM sleep using a plurality of EMG parameters extracted from the signals.

According to still further features in the described preferred embodiments the method further comprises determining periods of the REM sleep using a Poincare plot of the series of cardiac R-R intervals.

According to still further features in the described preferred embodiments the method further comprises: obtaining also periods of the LS, defined as a period other than the SWS period, other than the SO periods, other than the non-sleep periods and other than the REM periods.

According to still another aspect of the present invention there is provided a method of determining a sleep apnea from signals of electrical activity recorded of a chest of a sleeping subject, the signals being measured over a plurality of epochs, the method comprising: (a) extracting a series of cardiac R-R intervals from the signals; (b) determining awakening periods of the sleeping subject and excluding cardiac R-R intervals corresponding to the awakening periods from the series of cardiac R-R intervals; (c) obtaining a power spectrum from the series of cardiac R-R intervals; and (d) using the power spectrum to determine the sleep apnea of the sleeping subject.

According to still further features in the described preferred embodiments the method further comprises determining body positions or a change in a body position of the sleeping subject prior to step (b), and executing steps (b)-(d) separately for each one of the body positions.

According to still further features in the described preferred embodiments the method further comprises discarding signals corresponding to abnormal heart beats of the sleeping subject, prior to step (a).

According to still further features in the described preferred embodiments the method further comprises interpolating the signals so as to compensate missing heart beats of the sleeping subject, prior to step (a).

According to still further features in the described preferred embodiments the obtaining the power spectrum is by a discrete transform.

According to still further features in the described preferred embodiments the discrete transform is selected from the group consisting of a steady state discrete transform and a time-dependent discrete transform.

According to still further features in the described preferred embodiments step (d) comprises obtaining, for each period other than the awakening period, a power spectrum component of the power spectrum, and if the power spectrum component is above a predetermined threshold then identifying sleep apnea for the period.

According to still further features in the described preferred embodiments the method further comprises: employing a pattern recognition procedure on a portion of the series of cardiac R-R intervals, so as to identify representative patterns of sleep apnea; and identifying periods corresponding to the representative patterns as sleep apnea periods.

According to still further features in the described preferred embodiments the portion of the series of cardiac R-R intervals corresponds to body positions having durations lower than a predetermined threshold.

According to still further features in the described preferred embodiments the predetermined threshold equals about 200 seconds plus total awakening time in a respective body position.

According to still further features in the described preferred embodiments the portion of the series of cardiac R-R intervals corresponds to periods characterized by a power spectrum component which is below a predetermined threshold, the power spectrum component is power of signals being at a frequency range representing sleep apnea.

According to an additional aspect of the present invention there is provided an apparatus for determining a Slow-Wave-Sleep (SWS) period and a Non-SWS (NSWS) period from signals of electrical activity recorded of a chest of a sleeping subject, the signals being measured over a plurality of epochs, the apparatus comprising: an R-R extractor for extracting a series of cardiac R-R intervals from the signals; a decomposer for obtaining a time-frequency decomposition from the series of cardiac R-R intervals; and an SWS determinator, for determining the SWS period using the time-frequency decomposition; thereby to determine the SWS period and the NSWS period of the sleeping subject.

According to yet an additional aspect of the present invention there is provided an apparatus for determining a REM sleep and a NREM sleep from signals of electrical activity recorded of a chest of a sleeping subject, the signals being measured over a plurality of epochs, the apparatus comprising: an EMG extractor for extracting a plurality of EMG parameters from the signals; and a REM determinator for using the plurality of EMG parameters to determine the REM sleep and the NREM sleep of the sleeping subject.

According to still an additional aspect of the present invention there is provided an apparatus for determining a REM sleep and a NREM sleep from signals of electrical activity recorded of a chest of a sleeping subject, the signals being measured over a plurality of epochs, the apparatus comprising: an R-R extractor, for extracting a series of cardiac R-R intervals from the signals; a plotter, for constructing a Poincare plot of the series of cardiac R-R intervals; and a REM determinator, for using the Poincare plot to determine the REM sleep and the NREM sleep of the sleeping subject.

According to still further features in the described preferred embodiments the apparatus further comprising electronic-calculating functionality for calculating a plurality of moments with respect to a predetermined line along the Poincare plot, each of the plurality of moments being calculated within a predetermined time-window.

According to still further features in the described preferred embodiments the apparatus further comprising electronic-calculating functionality for normalizing each of the plurality of moments.

According to a further aspect of the present invention there is provided an apparatus for determining sleep stages from signals of electrical activity recorded of a chest of a sleeping subject, the signals being measured over a plurality of epochs, the apparatus comprising: a R-R extractor for extracting a series of cardiac R-R intervals from the signals; a decomposer, for obtaining a time-frequency decomposition from the series of cardiac R-R intervals; a SWS determinator for using the time-frequency decomposition to determine at least one SWS period and at least one NSWS period; a SO determinator for determining at least one SO period onset period from the at least one NSWS period; a non-sleep determinator for determining plurality of non-sleep periods from the at least one NSWS period; an EMG extractor, for extracting a plurality of EMG parameters from a portion of the signals, the portion corresponds to a NSWS period other than the at least one SO period and other than the plurality of non-sleep periods; a REM determinator for using the plurality of EMG parameters to determine at least one REM period thereby to obtain also at least one LS period defined as a NSWS period other than the at least one SO period, other than the plurality of non-sleep periods and other than the at least one REM period; thereby to determine the sleep stages of the sleeping subject.

According to still further features in the described preferred embodiments the apparatus further comprising a Stage-2 determinator for determining, from the at least one LS period, at least one Stage-2 period, thereby to obtain also a Stage-1 period, the Stage-1 period being defined as a LS period other than at least one Stage-2 period.

According to still further features in the described preferred embodiments the apparatus further comprising electronic-calculating functionality for normalizing the at least one SO parameter.

According to still further features in the described preferred embodiments the apparatus further comprising a statistical analyzer for analyzing the at least one SO parameter using a plurality of statistical quantities.

According to yet a further aspect of the present invention there is provided a system for determining a SWS period and a NSWS period of a sleeping subject, the system comprising: an apparatus for providing signals of electrical activity of a chest of the sleeping subject, measured over a plurality of epochs; an R-R extractor for extracting a series of cardiac R-R intervals from the signals; a decomposer for obtaining a time-frequency decomposition from the series of cardiac R-R intervals; and an SWS determinator, for determining the SWS period using the time-frequency decomposition; thereby to determine the SWS period and the NSWS period of the sleeping subject.

According to still a further aspect of the present invention there is provided a system for determining a REM sleep and a NREM sleep of a sleeping subject, the system comprising: an apparatus for providing signals of electrical activity of a chest of the sleeping subject, measured over a plurality of epochs; an EMG extractor for extracting a plurality of EMG parameters from the signals; and a REM determinator for using the plurality of EMG parameters to determine the REM sleep and the NREM sleep of the sleeping subject.

According to still a further aspect of the present invention there is provided a system for determining a REM sleep and a NREM sleep of a sleeping subject, the system comprising: an apparatus for providing signals of electrical activity of a chest of the sleeping subject, measured over a plurality of epochs; an R-R extractor, for extracting a series of cardiac R-R intervals from the signals; a plotter, for constructing a Poincare plot of the series of cardiac R-R intervals; and a REM determinator, for using the Poincare plot to determine the REM sleep and the NREM sleep of the sleeping subject.

According to still further features in the described preferred embodiments the apparatus for providing signals comprises cardiac electrodes, adapted for attachment to a plurality of predetermined locations on the chest of the sleeping subject, the plurality of predetermined locations are selected so as to substantially optimize heart-beat reads from the signals.

According to still further features in the described preferred embodiments the apparatus for providing signals comprises a single lead, adapted for attachment to a predetermined location on the chest of the sleeping subject, the predetermined location is selected so as to substantially optimize heart-beat reads from the signals.

According to still further features in the described preferred embodiments each of the plurality of predetermined locations is adjacent to a different muscle.

According to still further features in the described preferred embodiments at least two of the plurality of predetermined locations are adjacent to the same muscle.

According to still further features in the described preferred embodiments the system further comprising electronic-calculating functionality for calculating a plurality of Moments with respect to a predetermined line along the Poincare plot, each of the plurality of Moments being calculated within a predetermined time-window.

According to still further features in the described preferred embodiments the plurality of Moments is a plurality of Moments of inertia.

According to still further features in the described preferred embodiments the REM determinator is programmed to define the REM period by a plurality of epochs, each characterized by a Moment which is below a predetermined threshold.

According to still further features in the described preferred embodiments the predetermined line along the Poincare plot is a straight line, forming a predetermined angle with respect to an axis of the Poincare plot.

According to still further features in the described preferred embodiments the predetermined angle equals about 45 degrees.

According to still further features in the described preferred embodiments the system further comprising electronic-calculating functionality for normalizing each of the plurality of Moments.

According to still a further aspect of the present invention there is provided a system for determining sleep stages of a sleeping subject, the system comprising: an apparatus for providing signals of electrical activity of a chest of the sleeping subject, measured over a plurality of epochs; an R-R extractor for extracting a series of cardiac R-R intervals from the signals; a decomposer, for obtaining a time-frequency decomposition from the series of cardiac R-R intervals; a SWS determinator for using the time-frequency decomposition to determine at least one SWS period and at least one NSWS period; a SO determinator for determining at least one SO period onset period from the at least one NSWS period; a non-sleep determinator for determining a plurality of non-sleep periods from the at least one NSWS period; an EMG extractor, for extracting a plurality of EMG parameters from a portion of the signals, the portion corresponds to a NSWS period other than the at least one SO period and other than the plurality of non-sleep period; a REM determinator for using the plurality of EMG parameters to determine at least one REM period thereby to obtain also at least one LS period defined as a NSWS period other than the at least one SO period, other than the plurality of non-sleep periods and other than the at least one REM period; thereby to determine the sleep stages of the sleeping subject.

According to still further features in the described preferred embodiments the apparatus for providing signals is an ECG apparatus.

According to still further features in the described preferred embodiments the apparatus for providing signals comprises cardiac electrodes, adapted for attachment to a plurality of predetermined locations on the chest of the sleeping subject, the plurality of predetermined locations are selected so as to substantially optimize heart-beat reads from the signals and to substantially optimize EMG reads from the signals.

According to still further features in the described preferred embodiments the apparatus for providing signals comprises a single lead, adapted for attachment to a predetermined location on the chest of the sleeping subject, the predetermined location is selected so as to substantially optimize heart-beat reads from the signals and to substantially optimize EMG reads from the signals.

According to still further features in the described preferred embodiments the system further comprising a Stage-2 determinator for determining, from the at least one LS period, at least one Stage-2 period, thereby to obtain also a Stage-1 period, the Stage-1 period being defined as a LS period other than at least one Stage-2 period.

According to still further features in the described preferred embodiments the decomposer is operable to calculate, for each epoch, at least one time-dependent power spectrum component selected from the group consisting of a VLF power spectrum, a LF power spectrum and a HF power spectrum.

According to still further features in the described preferred embodiments the SWS determinator is programmed to define the SWS period by a plurality of epochs, each characterized by at least one power parameter which is below a predetermined threshold, the at least one power parameter is selected from the group consisting of the VLF power spectrum, the LF power spectrum, the HF power spectrum, and a combination between two of the VLF, the LF and the HF power spectra.

According to still further features in the described preferred embodiments the combination is a ratio.

According to still further features in the described preferred embodiments the predetermined threshold is constant.

According to still further features in the described preferred embodiments the predetermined threshold is a first function of an average value of the at least one power parameter.

According to still further features in the described preferred embodiments the first function is a linear function.

According to still further features in the described preferred embodiments the predetermined threshold varies with time.

According to still further features in the described preferred embodiments the decomposer is operable to calculate the VLF, the LF and the HF power spectra within a window along the series of cardiac R-R intervals, the window being characterized by a duration which is a function of a respective frequency.

According to still further features in the described preferred embodiments the function of the respective frequency is inversely related to the respective frequency.

According to still further features in the described preferred embodiments the window has an aperture selected from the group consisting of: a rectangular aperture, a Hamming aperture, a Hanning aperture, a Blackman aperture, a Gaussian window, a Lorentzian window, a sinc window, a power of a sine window and a power of a cosine window.

According to still further features in the described preferred embodiments the decomposer comprises a wavelet processor.

According to still further features in the described preferred embodiments the wavelet processor is selected from the group consisting of a discrete wavelet processor and a continuous wavelet processor.

According to still further features in the described preferred embodiments the decomposer comprises a selective discrete spectral processor.

According to still further features in the described preferred embodiments the decomposer further comprises a spectral transform selector for selecting a transform from the group consisting of: a Fourier transform, a Haar transform, a Hartley transform, a sine transform, a cosine transform, and a Hadamard transform.

According to still further features in the described preferred embodiments the SO determinator comprises electronic-calculating functionality for calculating at least one SO parameter and for defining the SO period to be at least one epoch being by at least one SO parameter which is above a predetermined threshold, over a predetermined time range.

According to still further features in the described preferred embodiments the predetermined time range is from 2 epochs to 10 epochs.

According to still further features in the described preferred embodiments the at least one SO parameter comprises at least one integrated power spectrum calculated by integrating at least one of the power spectra over predetermined frequency limits.

According to still further features in the described preferred embodiments the at least one SO parameter further comprises at least one time-dependent power ratio calculated using the at least one integrated power spectrum.

According to still further features in the described preferred embodiments the SO determinator further comprises electronic-calculating functionality for calculating the predetermined frequency limits.

According to still further features in the described preferred embodiments the system further comprising electronic-calculating functionality for normalizing the at least one SO parameter.

According to still further features in the described preferred embodiments the system further comprising a statistical analyzer for analyzing the at least one SO parameter using a plurality of statistical quantities.

According to still further features in the described preferred embodiments the plurality of statistical quantities selected from the group consisting of an average, a variance and a t-test.

According to still further features in the described preferred embodiments the plurality of non-sleep periods comprises at least one awakening period and/or at least one arousal period.

According to still further features in the described preferred embodiments the non-sleep determinator comprises: (a) a low-pass filter for filtering the series of cardiac R-R intervals, thereby to provide a first series of signals; and (b) an awakening period definer for defining the at least one awakening period as a plurality of epochs each associated with at least one of the first series of signals which is below a predetermined threshold.

According to still further features in the described preferred embodiments the low-pass-filter is at about 0.01 Hz.

According to still further features in the described preferred embodiments the predetermined threshold is about 0.85 of an averaged value of the first series of signals.

According to still further features in the described preferred embodiments the non-sleep determinator comprises: (a) a band-pass-filter for filtering the series of cardiac R-R intervals, thereby providing a second series of signals; and (b) an arousal period definer for defining the at least one arousal period as a plurality of epochs each associated with at least one of the second series of signals which is below a predetermined threshold.

According to still further features in the described preferred embodiments the band-pass-filter is characterized by a lower band limit of about 0.05 Hz and an upper band limit of about 0.2 Hz.

According to still further features in the described preferred embodiments the predetermined threshold is about 0.85 of an averaged value of the second series of signals.

According to still further features in the described preferred embodiments the predetermined profile is characterized by a specific width and a specific depth.

According to still further features in the described preferred embodiments the EMG extractor comprises an eliminator for eliminating at least one signal selected from the group consisting of: a P wave, a T wave and a QRS-complex.

According to still further features in the described preferred embodiments the eliminator comprises at least one high pass filter for filtering out the P wave and the T wave.

According to still further features in the described preferred embodiments the high pass filter is characterized by a threshold frequency of about 10 Hz.

According to still further features in the described preferred embodiments the eliminator is operable comprises to eliminate the QRS-complex by a combination of gating and/or subtraction.

According to still further features in the described preferred embodiments the plurality of EMG parameters are selected from the group consisting of: normalized amplitude (mrEMG), normalized mean power (nPWR), zero-crossing average (ZC), median frequency (MF), mean power frequency (MPF), Expected Zero Crossing (EZC), power variance (PVAR), turns (NT) and Complexity (Cmplx).

According to still further features in the described preferred embodiments the REM determinator is programmed to define the REM period by a plurality of epochs, each characterized by at least one of the plurality of EMG parameters which is below a predetermined threshold.

According to still further features in the described preferred embodiments the Stage-2 determinator is programmed to define the at least one Stage-2 period by a plurality of epochs, each associated to a cardiac R-R interval corresponding to a K-complex.

According to still further features in the described preferred embodiments the cardiac R-R interval corresponding to the K-complex is characterized by a specific width and a specific depth.

According to still another aspect of the present invention there is provided an apparatus for determining a body position or a change in the body position from signals of electrical activity recorded of a chest of a sleeping subject, the signals being QRS complexes, the apparatus comprising: an RWD extractor for extracting R-wave durations from the QRS complexes, thereby to obtain an R-wave duration function a body position determinator for determining the body position or the change in the body position of the sleeping subject using the RWD function.

According to still further features in the described preferred embodiments the apparatus further comprises a segment calculator for defining at least two segments of each of the QRS complexes and determining width of each of the at least two segments, thereby to obtain, for each QRS complex, a set of widths, the set being representative of the body position.

According to still another aspect of the present invention there is provided an apparatus of characterizing a sleep of a sleeping subject, the apparatus comprising: an ABI calculator, for calculating at least one ABI, each corresponding to a different sleep stage of the sleeping subject, the ABI calculator is operable to calculated the ABI using a weight of the sleep stage and at least one power parameter; and a sleep characterizer for characterizing the sleep of the sleeping subject using the at least one ABI.

According to still further features in the described preferred embodiments the apparatus further comprises an obstructive sleep apnea determinator, for determining an obstructive sleep apnea for the sleeping subject if one or more of the at least one ABI is larger than a predetermined threshold.

According to still further features in the described preferred embodiments the ABI calculator is operable to sum the at least two ABIs thereby to provide a total ABI.

According to still further features in the described preferred embodiments the apparatus further comprises an obstructive sleep apnea determinator, for determining an obstructive sleep apnea for the sleeping subject if the total ABI is larger than a predetermined threshold.

According to still further features in the described preferred embodiments the sleep stage is selected from the group consisting of a SWS, a REM sleep and an LS.

According to still further features in the described preferred embodiments the apparatus further comprises: an R-R extractor, for extracting a series of cardiac R-R intervals from signals of electrical activity recorded of a chest of the sleeping subject; a decomposer, for obtaining a time-frequency decomposition from the series of cardiac R-R intervals; and an SWS determinator for using the time-frequency decomposition to determine periods of the SWS.

According to still further features in the described preferred embodiments the apparatus further comprises an EMG extractor, for extracting a plurality of EMG parameters from signals of electrical activity recorded of a chest of the sleeping subject; the portion corresponds to a NSWS period other than the at least one SO period and other than the plurality of non-sleep period; a REM determinator for using the plurality of EMG parameters to determine periods of the REM sleep.

According to still further features in the described preferred embodiments the apparatus further comprises an R-R extractor, for extracting a series of cardiac R-R intervals from the signals; a plotter, for constructing a Poincare plot of the series of cardiac R-R intervals; and a REM determinator, for using the Poincare plot to determine periods of the REM sleep.

According to still further features in the described preferred embodiments the apparatus further comprises: a SO determinator for determining periods of SO from the signals; a non-sleep determinator for determining periods of non-sleep from the signals; an EMG extractor, for extracting a plurality of EMG parameters from a portion of the signals, the portion corresponding to periods other than the SWS periods, other than the SO periods and other than the non-sleep periods; a REM determinator for using the plurality of EMG parameters to determine periods of the REM sleep, thereby to obtain also periods of the LS defined as periods other than the SWS periods, other than the SO periods, other than non-sleep periods and other than the REM periods.

According to still another aspect of the present invention there is provided an apparatus for determining a sleep apnea from signals of electrical activity recorded of a chest of a sleeping subject, the signals being measured over a plurality of epochs, the apparatus comprising: an R-R extractor for extracting a series of cardiac R-R intervals from the signals; a non-sleep determinator for determining awakening periods of the sleeping subject and excluding cardiac R-R intervals corresponding to the awakening periods from the series of cardiac R-R intervals; a decomposer for calculating a power spectrum from the series of cardiac R-R intervals; and a sleep apnea determinator for using the power spectrum and determining the sleep apnea of the sleeping subject.

According to still further features in the described preferred embodiments the apparatus further comprises a body positions determinator for determining body positions or a change in a body position of the sleeping subject.

According to still further features in the described preferred embodiments the apparatus further comprises a discrete transformer for obtaining the power spectrum.

According to still further features in the described preferred embodiments the apparatus further comprises a pattern recognition functionality for identifying representative patterns of sleep apnea.

According to still another aspect of the present invention there is provided a system for determining a body position or a change in the body position of a sleeping subject, the system comprising: an apparatus for providing signals of electrical activity of a chest of the sleeping subject, characterized by QRS complexes; an R-wave duration (RWD) extractor for extracting R-wave durations from the QRS complexes, thereby to obtain an R-wave duration function a body position determinator for determining the body position or the change in the body position of the sleeping subject using the RWD function.

According to still further features in the described preferred embodiments the RWD extractor is operable to define the change in the body position when a change of the RWD function is above a predetermined threshold.

According to still further features in the described preferred embodiments the predetermined threshold is a standard deviation of the RWD function.

According to still further features in the described preferred embodiments the body position determinator is operable to calculate at least one local average of the RWD function.

According to still further features in the described preferred embodiments the body position determinator is operable to calculate a difference between two local averages of the RWD function.

According to still further features in the described preferred embodiments the body position is one of two body positions.

According to still further features in the described preferred embodiments the body position determinator is operable to define a first body position, when a value of the RWD function is high and a second body position, when a value of the RWD function is low.

According to still further features in the described preferred embodiments the system further comprises a segment calculator for defining at least two segments of each of the QRS complexes and determining width of each of the at least two segments, thereby to obtain, for each QRS complex, a set of widths, the set being representative of the body position.

According to still further features in the described preferred embodiments the segment calculator is operable to calculate nth-order derivatives of R-waves of the QRS complex, where n is a positive integer, and further wherein the segment calculator is operable to locate zeros of the nth-order derivatives.

According to still further features in the described preferred embodiments the at least two segments comprise a left segment and a right segment and the body position is one of four body positions.

According to still further features in the described preferred embodiments the body position determinator is operable to define: a first body position, when a value of the left segment is high and a value of the right segment is high; a second body position, when a value of the left segment is low and a value of the right segment is high; a third body position, when a value of the left segment is high and a value of the right segment is low; and a fourth body position, when a value of the left segment is low and a value of the right segment is low.

According to still another aspect of the present invention there is provided a system for determining a sleep apnea of a sleeping subject, the system comprising: an apparatus for providing signals of electrical activity of a chest of the sleeping subject, measured over a plurality of epochs; an R-R extractor for extracting a series of cardiac R-R intervals from the signals; a non-sleep determinator for determining awakening periods of the sleeping subject and excluding cardiac R-R intervals corresponding to the awakening periods from the series of cardiac R-R intervals; a decomposer for calculating a power spectrum from the series of cardiac R-R intervals; and a sleep apnea determinator for using the power spectrum and determining the sleep apnea of the sleeping subject.

According to still further features in the described preferred embodiments the system further comprises a body positions determinator for determining body positions or a change in a body position of the sleeping subject.

According to still further features in the described preferred embodiments the system further comprises a discrete transformer for obtaining the power spectrum.

According to still further features in the described preferred embodiments the discrete transformer is selected from the group consisting of a steady state discrete transformer and a time-dependent discrete transformer.

According to still further features in the described preferred embodiments the discrete transformer is operable to perform a transform selected from the group consisting of a discrete Fourier transform, a discrete Hartley transform, a discrete sine transform, a discrete cosine transform, a discrete Hadamard transform, a discrete Haar transform and a discrete wavelet transform.

According to still further features in the described preferred embodiments the sleep apnea determinator is operable to obtain a power spectrum component of the power spectrum, and to identify sleep apnea if the power spectrum component is above a predetermined threshold.

According to still further features in the described preferred embodiments the power spectrum component is power of signals being at a frequency range representing sleep apnea.

According to still further features in the described preferred embodiments the frequency range is from about 0.01 Hz to about 0.04 Hz.

According to still further features in the described preferred embodiments the predetermined threshold is about half of a total power of the power spectrum.

According to still further features in the described preferred embodiments the system further comprises a pattern recognition functionality for identifying representative patterns of sleep apnea.

According to still further features in the described preferred embodiments the representative patterns are characterized by a U-shape of the cardiac R-R intervals.

The present invention successfully addresses the shortcomings of the presently known configurations by providing methods, apparati and systems for determining sleep stages, body positions and/or sleep disorders, based on data derived solely from electrical signals recorded of a chest of a sleeping subject. The methods, apparati and systems of the invention enjoy properties far exceeding those characterizing prior art techniques.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

Implementation of the method, apparatus and system of the present invention involves performing or completing selected tasks or steps manually, automatically, or a combination thereof. Moreover, according to actual instrumentation and equipment of preferred embodiments of the method, apparatus and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method, apparatus and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a flowchart of a method of determining a SWS period and a NSWS period from signals of electrical activity recorded of a chest of a sleeping subject, according to the present invention;

FIG. 2 is a flowchart of a method of determining a REM sleep and NREM sleep from signals of electrical activity recorded of a chest of a sleeping subject, using a plurality of electromyogram parameters, according to the present invention;

FIG. 3 is a flowchart of a method of determining a REM sleep and NREM sleep from signals of electrical activity recorded of a chest of a sleeping subject, using a Poincare plot, according to the present invention;

FIG. 24a shows integrated VLF power as a function of time calculated for a second sleep onset study detailed in Example 4, below;

FIG. 24b shows integrated LF power as a function of time calculated for the second sleep onset study of Example 4;

FIG. 24c shows integrated LF power as a function of time calculated for the second sleep onset study of Example 4;

FIG. 24d shows EEG power spectrum in Delta frequency band as a function of time calculated for the second sleep onset study of Example 4;

FIG. 24e shows EEG power spectrum in Alpha frequency band as a function of time calculated for the second sleep onset study of Example 4;

FIG. 24f shows sleep stages as measured and identified based on standard sleep scoring criteria, for the second sleep onset study of Example 4;

FIGS. 25a-f show the same parameters of FIG. 24, for a different subject, which also participated in the second sleep onset study of Example 4;

FIGS. 38a-d shows power spectra of three adjacent segments of the RRI series.

DESCRIPTION OF THE PREFERRED EMBODIMENTS

Figure 4:
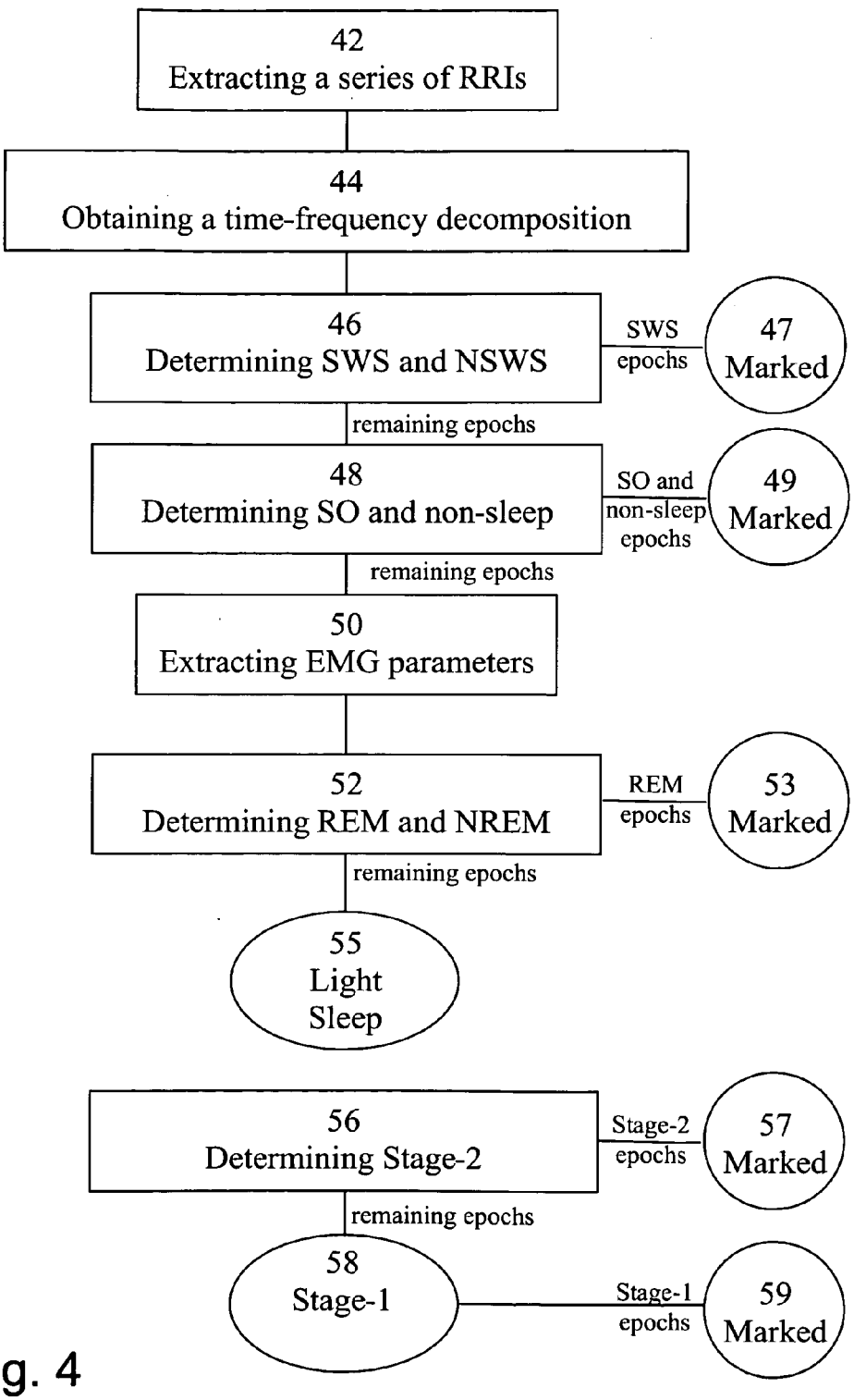
FIG. 4 is a flowchart of a method of determining various sleep stages from signals of electrical activity recorded of a chest of a sleeping subject, according to the present invention.

The present invention is of a method, apparatus and a system for determining sleep stages, body positions and/or sleep disorders of a sleeping subject using signals of electrical activity recorded of a chest of a sleeping subject, such as electrocardiogram (ECG) signals, reflecting cardiac electrical activity, and signals inherently associated with ECG signals, reflecting electrical activity of muscles, other than the heart muscle itself, present in the thorax of the sleeping subject. Specifically, the present invention can be used to determine, REM sleep, and NREM sleep of a sleeping subject. More specifically, the present invention can be used to determine REM sleep, Slow-Wave-Sleep, sleep onset, non-sleep periods and light sleep periods of the sleeping subject. Further, the present invention can be used for determining sleep apnea and correlate occurrences of all the above sleep stages with sleep apnea and the body position of the sleeping subject.

The principles and operation of a method, apparatus and a system for determining sleep stages of a sleeping subject according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

It the embodiments described below, signals, reflecting electrical activity of muscles, are recorded from the sleeping subject and analyzed thereafter. It is to be understood, that the recording procedure may be any known procedure for recording signals of electrical activity of muscles present in the thorax of the sleeping subject. Specifically, the signals may be recorded from the front side, the back side, the left side or the right side of the sleeping subject. The terms "thorax" and "chest" are used interchangeably throughout the specification.

According to one aspect of the invention, there is provided a method of determining a Slow-Wave-Sleep (SWS) period and a Non-SWS (NSWS) period from signals of electrical activity recorded of a chest of a sleeping subject, measured over a plurality of epochs. The method is generally referred to herein as method 10, and is illustrated in the flowchart of FIG. 1.

The signals of electrical activity may be recorded by an appropriate medical equipment, such as, but not limited to, an ECG apparatus or equivalent. The recorded signals may be, for example, ECG signals, reflecting cardiac electrical activity. More specifically, the signals may reflect electrical activity associated with heart-beats of the sleeping subject.

Referring now to FIG. 1, in a first step of method 10, designated by Block 12, a series of cardiac R-R intervals is extracted from the ECG signals. ECG signals include, inter alia, the so-called P waves, T waves and QRS complexes, which QRS complexes include Q waves, R-waves and S waves. An R-R interval (RRI) is the elapsed time between two successive R-waves of the ECG signals. Two known definitions exist for the R peak: (i) the highest (absolute value) peak in the QRS complex; and (ii) the first positive peak in the QRS complex. It should be understood, that, in all the embodiments detailed herein, any of the above definitions may be used when extracting the RRIs.

The RRI series serves for measuring heart rate changes, commonly referred to as Heart-Rate-Variability (HRV). The heartbeat changes are a direct consequence of alterations in the autonomic nervous system (ANS), which alterations, as further demonstrated hereinafter, can be used to determine many sleep stages, e.g., SWS. The procedure of extracting RRI series from the ECG signals is well known in the art and can be executed, either manually or automatically, e.g., by an R-wave detector which, in one embodiment, can be associated with the medical apparatus which provides the signals.

In a second step of method 10, designated by Block 14, a time-frequency decomposition is obtained from the RRI series. The time-frequency decomposition may be obtained in any way known in the art for calculating the frequency content of the RRI series. According to a preferred embodiment of the present invention, the time-frequency decomposition is obtained by calculating, for each epoch, at least one time-dependent power spectrum component. The power spectrum components include, but are not limited to, a very-low-frequency (VLF) power spectrum, a low-frequency (LF) power spectrum and a high-frequency (HF) power spectrum. As a general rule, the frequency bands reflect different activities of the autonomic nervous system. Specifically, high-frequencies reflect the fast reacting parasympathetic activity while low- and very-low-frequencies reflect both the parasympathetic and the slow reacting sympathetic activities. As further detailed and exemplified hereinunder, the SWS, as well as other sleep stages, can be characterized by various autonomic activities, which are expressed through HRV. A detailed description of a method of obtaining the time-frequency decomposition, according to a preferred embodiment of the present invention, is provided hereinafter.

In a third step of method 10, designated by Block 16, the time-frequency decomposition is used for determining the SWS period. Once the SWS periods are determined, the NSWS periods are defined as all the sleep periods other than the SWS periods.

According to a preferred embodiment of the present invention, the SWS period is defined by a plurality of epochs, each characterized by at least one power parameter which is below a predetermined threshold. The power parameters are preferably the VLF, LF and HF power spectra or any combination thereof. For example, one power parameter may be the ratio LF/HF, and another power parameter may be the ratio VLF/HF. The ratio LF/HF is also known as the sympathovagal balance.

The predetermined threshold, which is used for separating the SWS periods from the NSWS periods may be chosen in more than one way. In addition, according to a preferred embodiment of the present invention, more than one threshold may be used, so as to construct a set of criteria for identifying the SWS periods.

For example, it has been confirmed [Baharav A, Kotagal S, Gibbons V, et al., "Fluctuations in autonomic nervous activity during sleep displayed by power spectrum analysis of heart rate variability", *Neurology*, 45:1183-1187, 1995] that during SWS sleep there is an enhanced parasympathetic activity. Which enhanced parasympathetic activity is expressed by an increased percentage of the HF power at the expense of a reduction in the percentage of the LF power. Thus, in one preferred embodiment, a constant threshold may be imposed on the value of the LF power and/or the VLF power. A typical numerical value for this threshold is below the median (e.g., at about one third) of the possible range of the LF and/or VLF powers.

As used herein, the term about refers to ±10%.

Beside a constant threshold, the SWS period may also be identified using a threshold which varies from one sleeping subject to another, using a parameter which is particular to the sleeping subject, in a manner described herein.

Hence, in another preferred embodiment, one power parameter may be averaged over the entire sleep of the sleeping subject. This average power parameter, which can be considered as a particular power average for the sleeping subject, may be used for choosing the threshold. In other words, the threshold, separating between the SWS periods and the NSWS periods, is a function of the particular power average of the sleeping subject. For example, supposing that the power parameter is a ratio between LF power and HF power. Then, denoting the average of LF/HF for the entire sleep of the sleeping subject by (LF/HF), the predetermined threshold is a function of (LF/HF). According to a preferred embodiment of the present invention the threshold may be a linear function of (LF/HF) where the parameters of linear function are determined from experimental measurements, as further demonstrated in the Examples section that follows.

As can be understood from the above discussion, the threshold(s) of the above embodiments are time-independent. However, in yet another preferred embodiment of the present invention, the threshold(s) may also vary with time. During sleep, the power balance between the VLF, LF and HF power gradually increases. In this preferred embodiment, the numerical values of the above threshold may be adapted to the overall tendency of power balance to change over the sleep. For example, if a constant threshold is used, this constant threshold is selected to be smaller during the beginning of the sleep and higher towards the end of the sleep. If the threshold is a function of some average power parameter (e.g., (LF/HF)), the parameters of the function are selected so that the value of the function is smaller during the beginning of the sleep and higher towards the end of the sleep.

It is to be understood, that in addition to the above examples for selecting the thresholds separating between the SWS periods and the NSWS periods, other thresholds may be used, independently or in combination with the above examples to construct an optimal set of criteria.

Beside SWS periods, the present invention successfully addresses the problem of determining other sleep stages. Following is a description of two methods, referred to herein as method 20 and method 30, which, as will be explained, may be use independently or in combination to determine REM sleep and NREM sleep.

Reference is now made to FIG. 2, which is a flowchart of method 20 for determining REM sleep and NREM sleep from signals of electrical activity recorded of a chest of a sleeping subject, measured over a plurality of epochs.

As further detailed hereinbelow, the recorded signals may comprise, for example, signals inherently associated with ECG signals, reflecting electrical activity of muscles, other than the heart muscle itself, present in the chest of the sleeping subject. Similarly to method 10, the signals of electrical activity may be recorded by an appropriate medical equipment, such as, but not limited to, an ECG apparatus or equivalent.

In a first step of method 20, designated by Block 22, a plurality of electromyogram (EMG) parameters is extracted from the recorded signals. The P waves, the T waves and the QRS complexes of the heart-beat signals are generated by an electric dipole created by current flow between polarized and depolarized regions of the heart. The EMG information, on the other hand, is expressed through other deflections appearing, e.g., in ECG signals. Hence, according to a preferred embodiment of the present invention the first step is executed by eliminating P waves, T waves and QRS complexes, from the ECG signals. This may be done, for example by a combination of gating and/or subtraction techniques. A gating is a process of selecting a portion of the signal according to predetermined criteria, while a subtraction is a process of subtracting an average pattern from the signal. According to a preferred embodiment of the present invention, the gating criteria can be, selection of the signal segment between T wave and P wave, and the subtraction criteria can be subtraction of the average QRS pattern from the original signal. In addition, the P waves, the T waves and the QRS complexes may also be eliminated by high pass filtering at a predetermined threshold. A typical high-pass threshold is about 10 Hz.

In a second step of method 20, designated by Block 24, the EMG parameters are used to determine at least one REM period, which may be defined, for example, as a plurality of epochs, each characterized by at least one EMG parameter which is below a predetermined threshold. Once the REM periods are determined, the NREM periods are defined as all the sleep periods other than the REM periods.

It would be appreciated that the efficiency of method 20 depends on the procedure by which the signals are recorded, e.g., using leads of an ECG apparatus. In standard ECG leads, however, EMG signals are suppressed, typically by positioning different electrodes on different muscles or by using appropriate filters. Therefore, prior to the execution of method 20, the locations of the electrodes on sleeping subject are preferably selected so as to optimize those signals which correspond to the EMG parameters. This may be done, for example, by positioning two electrodes on a single skeleton muscle of the chest of the subject (e.g., Pectoralis Major or Pectoralis Minor).

Many EMG parameters are known [to this end see, e.g., Bartolo A, Roberts C, Dzwonczyk R R and Goldman E: "Analysis of diaphragm EMG signals comparison of gating vs. subtraction for removal of ECG contamination", *J. Appl. Phsiol.*, 80:1898-1902, 1996], and can be used for identifying the REM sleep. According to a preferred embodiment of the present invention the EMG parameters include, but are not limited to:

(i) a normalized amplitude (mrEMG), which may be defined as:

$$mrEMG = \frac{1}{N}\sum_{i=1}^{N}|s(i)|,$$

where s(i) is the ith sample of the EMG signal and N is the signal's section length;

(ii) a normalized mean power (nPWR), which may be defined as:

$$nPWR = \frac{1}{N}\left(\frac{1}{f_H - f_L}\right)\sum_{f=f_L}^{f_H} P(f),$$

where P(f) is the power spectrum at frequency f, and $f_L$ and $f_H$ are the low- and high-frequency limits, respectively;

(iii) a zero-crossing average (ZC), which may be defined as the number of intersects between the EMG signal and the zero level, divided by 2N;

(iv) a median frequency (MF), which may be defined from the equation:

$$\sum_{f=f_L}^{MF} P(f) = \sum_{f=MF}^{f_H} P(f);$$

(v) a mean power frequency (MPF), which may be defined as:

$$MPF = \sum_{f=f_L}^{f_H} fP(f) \bigg/ \sum_{f=f_L}^{f_H} P(f);$$

(vi) an expected zero crossing (EZC), which may be defined as:

$$EZC = \sqrt{\sum_{f=f_L}^{f_H} f^2 P(f) \bigg/ \sum_{f=f_L}^{f_H} P(f)};$$

(vii) a power variance (PVAR), which may be defined as:

$$PVAR = \sum_{f=f_L}^{f_H} [P(f) - \overline{P(f)}]^2 / N_f,$$

where $N_f$ is the number of frequencies between $f_L$ and $f_H$ at which the power, P, is calculated and where an overline represents an average;

(viii) a turns parameter (NT), which may be defined as the number of changes in EMG signal derivative sign, divided by 2N; and (ix) a complexity parameter (Cmplx), which may be defined as:

$$Cmplx = \sum_{f=f_L}^{f_H} f^4 P(f) \bigg/ \sum_{f=f_L}^{f_H} P(f).$$

A typical value for the low-frequency, $f_L$, is about 20 Hz, and a typical value for the high-frequency, $f_H$, is such that the frequency range $f_L \leq f \leq f_H$ includes about 95% of the total power in the frequencies from $f_L$ to one half of the EMG sample rate.

Reference is now made to FIG. 3, which is a flowchart of method 30 for determining REM sleep and NREM sleep from signals of electrical activity recorded of a chest of a sleeping subject, as further detailed hereinabove.

In a first step of method 30, designated by Block 32, an RRI series is extracted from the ECG signals, as detailed hereinabove, with respect to the first step of method 10.

In a second step of method 30, designated by Block 34, a Poincare plot is constructed from the RRI series. A Poincare plot is a graph generated from a vector of data. Typically, a Poincare plot is a two-dimensional graph in which a particular point on the graph represents a dependence of one datum of the vector on a preceding datum of the same vector, where the latter datum (the preceding) may be referred to as "the cause" and the former datum may be referred to as "the effect". In other words, the Poincare plot represents the dependence of a data set on its history. The gap between "the cause" and "the effect" may vary. According to a preferred embodiment of the present invention, the gap is from about one heart-beat to about 10 heart-beats or more.

In a third step of method 30, designated by Block 36, the Poincare plot is used for determining the REM sleep and the NREM sleep of the sleeping subject. While reducing the present invention to practice, it has been unexpectedly uncovered that the REM sleep is related to certain moments, each calculated for points of the Poincare plot, which are selected within a predetermined time-widow (e.g., a two-minute time-window, a three-minute time-window, etc.).

Many moments may be defined on the Poincare plot for the purpose of determining a REM sleep, as further detailed below. One such moment is a moment of inertia. Broadly speaking, the moment of inertia is calculated by performing a summation of a plurality of squared distances of a plurality of points from a point, a line or a plane of reference, where each term in the summation is weighted by a respective mass. In one embodiment, all the points on the Poincare plot have equal "masses". Hence, the moment of inertia is defined by $IM = m\Sigma D_i^2$, where $D_i$ is a distance of the ith point of the Poincare plot from a predetermined line along the plot, m is an arbitrary mass parameter and the summation is over at least a portion of the points. The predetermined line may be, for example, a straight line, forming a predetermined angle (e.g., 45°) with respect to one axis of the Poincare plot.

Irrespective of the type of moments being chosen, the calculated moments may be normalized by dividing each moment by the total number of points. In addition, some of the points of the Poincare plot, failing to obey some statistical requirement, may be excluded from the calculation. For example, in embodiments in which the moments of inertia are used the statistical requirement may be that the distance, D, is smaller than the average of absolute D plus one standard deviation of D.

According to a preferred embodiment of the present invention, the REM sleep is defined by a plurality of epochs, each characterized by a moment which is below a predetermined threshold. Once the REM sleep is determined, the NREM sleep is defined as all the sleep periods other than the REM periods.

As stated, method 20 and method 30 may be executed either independently or in combination. Specifically, each of method 20 and method 30 may be solely executed to identify the REM sleep, or, alternatively, both method 20 and method 30 may be executed to determine the REM sleep of the same sleeping subject, and the respective results may be processed using statistical techniques so as to improve the accuracy of the analysis. It should be understood, that both method 20 and method 30 may be employed on the same dataset, where for each method a different portion of the dataset is used. For example, if the dataset includes ECG signals recorded of the chest of the sleeping subject using an ECG apparatus, then, for method 30, the R-waves of the ECG are used, while for method 20, the EMG portion of the ECG is used. The EMG portion of the ECG is also referred to in the literature as the "noise", the "background" or the "contamination" of the ECG. As further demonstrated in the Examples section that follows, information may be simultaneously extracted both from this "noise" and from the heart-beat signal using non-standard leads of the ECG apparatus (e.g., by locating both ECG electrodes on the Pectoralis Major or the Pectoralis Minor). Hence, the present invention successfully exploits both the ECG itself and its associated "noise" which is EMG signals associated with electrical activity of the chest muscles other than the heart itself.

Methods of determining specific sleep stages of a sleeping subject (e.g., methods 10, 20 and 30) may also be combined to obtain a powerful tool for providing a detailed and substantially complete analysis of the various sleep stages of the subject over the entire sleep.

Hence, according to another aspect of the present invention, there is provided a method of determining sleep stages from signals of electrical activity recorded of a chest of a sleeping subject, measured over a plurality of epochs (hereinafter the dataset). The method is generally referred to herein as method 40, and is illustrated in the flowchart of FIG. 4.

Method 40 is directed at determining the sleep stages in a manner that each epoch identified as a sleep stage is marked and excluded from the dataset. This approach has the advantage that (i) no epoch is identified as belonging to more than one sleep stage; and (ii) sleep stages which are difficult to be distinguish may be better identified, because the corresponding epochs propagate through the steps of the analysis and are therefore being filtered by different criteria.

Referring now to FIG. 4, in a first step of method 40, designated by Block 42, a series of RRIs is extracted from the ECG signals, as further detailed hereinabove. In a second step, designated by Block 44, a time-frequency decomposition is obtained from the RRI series. As already stated, the time-frequency decomposition may be obtained in any known way, and a detailed description of a method of obtaining such decomposition is provided hereinafter. Similarly to method 10, the time-frequency decomposition is preferably obtained by calculating, for each epoch, at least one time-dependent power spectrum component, each of which may independently be a VLF, an LF, an HF power spectrum or any other frequency-band power spectrum.

In a third step, designated by Block 46, the time-frequency decomposition is used for determining at least one SWS period and at least one NSWS period. The SWS and the NSWS periods may be determined, e.g., by executing the respective method steps of method 10. Block 47 represents the epochs which are identified and marked as SWS periods. Once the SWS periods are determined the marked epochs are excluded from the dataset, while the remaining epochs (NSWS) are used for the following steps.

In a forth step, designated by Block 48, at least one sleep-onset (SO) period and a plurality of non-sleep periods are determined from the remaining epochs. SO is commonly referred to as a transition between quiet wakefulness and sleep. The SO periods are preferably defined as at least one epoch which is characterized by at least one SO parameter which is above a predetermined threshold, over a predetermined time range (typically 2-10 epochs). As can be understood, the SO parameters are selected so as to characterize a transition between quiet wakefulness and sleep. Although it is known that SO detection is a complicated task, it has been found by the inventors of the present invention that the time-frequency decomposition may be used to detect unique changes of autonomic function involved in the process of falling asleep. These unique changes are preferably used as parameters for determining the SO periods.

Thus, in one embodiment, the SO parameters are calculated by integrating, over predetermined frequency limits, at least one of the power spectra calculated in the second step of method 40. In another embodiment, the SO parameters are defined as time-dependent power ratios calculated using the integrated power spectra. The time-dependent power ratios may be, for example, a ratio between two integrated power spectra or a ratio between an integrated power spectrum and an integrated total power.

Beside integration limits which are the frequency thresholds defining the various power spectrum components, other integration limits may be used so as to optimize the ability of the SO parameters to characterize transition between quiet wakefulness and sleep.

One procedure for calculating the integration limits, according to a preferred embodiment of the present invention, is by obtaining a steady state power spectrum from the RRI series and employing a method known as a minimum-cross-entropy method so as to separate between frequency peaks of the steady state power spectrum. The steady state power spectrum may be obtained by any known mathematical transform such as, but not limited to, a Fourier transform. The minimum-cross-entropy method is found, e.g., in the following publications, the contents of all of which are hereby incorporated by reference: Kullback, S., "Information Theory and Statistics", John Wiley, New York, 1959; Seth, A. K., Kapur J. N., "A comparative assessment of entropic and non-entropic methods of estimation", *Maximum Entropy and Bayesian Methods*, Fougere, P. F. (Ed.), Kluwer Academic Publishers, 451-462, 1990; Brink, A. D., Pendock N. E., "Minimum Cross-Entropy Threshold Selection", *Patt. Recog.* 29:179-188, 1996. The advantage of using the minimum-cross-entropy threshold method is that this method, without assuming any a priori knowledge about the original spectrum distribution, sets the optimal integration limits so that the difference in the information content between the original and segmented spectra is minimized. A more detailed description of the minimum-cross-entropy method is provided in Appendix 1 of the Examples section. According to a preferred embodiment of the present invention, irrespectively of the method in which the SO parameters are calculated, each SO parameter is normalized and/or analyzed by calculating a plurality of statistical quantities. The statistical quantities include, but are not limited to, an average, a variance and a t-test. The normalization may be, for example, by dividing each SO parameter by its average. The advantage of normalizing the SO parameters is to minimize influence of variation in HRV power and ratio values.

As stated, in the fourth step the plurality of non-sleep periods are determined. Broadly speaking, non-sleep periods are accompanied first by an acceleration of the heart-rate (i.e., a decrement of the RRI values) and second by a deceleration of the heart-rate (i.e., an increment of the RRI values), where the RRI decrement is slower than its increment. In addition, before a non-sleep period the RRI values are typically above the RRI mean value. As further detailed hereinunder, these characteristics are used for the purpose of determining the epochs of non-sleep periods from the RRI series.

There are different types of non-sleep periods occurring during sleep, which, according to a preferred embodiment of the present invention, can be determined by method 40. These include, but are not limited to, awakening periods and arousal periods. For a detailed definition of awakenings and arousals during sleep the reader is referred to an article by Bonnet M. et al., entitled "EEG arousals: scoring rules and examples: a preliminary report from the Sleep Disorders Atlas Task Force of the American Sleep Disorders Association", published in *Sleep*, 15(2):173-84, 1992.

The main difference between awakenings and arousals is at the scale at which these non-sleep periods affect the ECG signal. Specifically the awakening periods, which are typically characterized by trace duration of at least 30 seconds, affect the ECG signal in the low frequencies region while the arousals periods, which are typically characterized by trace duration of 5-10 seconds, affect the ECG signal in the intermediate-high frequencies region.

Thus, according to a preferred embodiment of the present invention, the RRI series is filtered using a low-pass-filter thereby providing a first series of signals. Then, the awakening periods are defined as a plurality of epochs each associated with at least one of the first series of signals which is below a predetermined threshold.

Similarly, for the purpose of determining the arousal periods, the RRI series is preferably filtered using a band-pass-filter thereby providing a second series of signals. Then, the arousal periods are defined as a plurality of epochs each associated with at least one of the second series of signals which is below a predetermined threshold.

Typical thresholds for the awakening and arousals periods are about 0.85 of the averaged value of the first series and the second series of signals, respectively. A typical cutoff frequency for the low-pass-filter is about 0.01 Hz, and typical cutoff frequencies of the band-pass-filter are 0.05 Hz for the low limit and about 0.2 Hz for upper band limit.

Block 49 represents the epochs which are identified and marked in the fourth step. Once the SO periods and the non-sleep periods are identified, the corresponding epochs are excluded from the dataset, while the remaining epochs are used for the following steps.

Thus, in a fifth step, designated by Block 50 of FIG. 4, a plurality of EMG parameters is extracted from the remaining portion of the dataset. This step is preferably executed similarly to the respective step of method 20. In a sixth step, designated by Block 52 and preferably executed similarly to the respective step of method 20, the EMG parameters are used to determine at least one REM period, e.g., as a plurality of epochs, each characterized by at least one EMG parameter which is below a predetermined threshold. Block 53, represents the epochs which are identified and marked as REM.

Once the REM periods are identified, the corresponding epochs are excluded from the dataset, while the remaining epochs are used for a seventh step of method 40. In the seventh step, designated by Block 55, all the remaining epochs (once the sixth step is completed) are defined as Light-Sleep (LS) periods.

In a preferred embodiment, designated by Block 56, at least one Stage-2 period is defined from the remaining portion of the dataset (the LS portion), thereby obtaining also a Stage-1 period which is defined as all the LS epochs other than those identified as Stage-2 epochs. Block 57 represents the epochs which are identified and marked as Stage-2 and Blocks 58 and 59 represent all the remaining epochs which are defined (Block 58) and marked (Block 59) as Stage-1.

According to a preferred embodiment of the present invention the Stage-2 periods are defined by a plurality of epochs, each associated to an RRI corresponding to a K-complex, which is characterized by a specific width and a specific depth. Similarly to the detection of the non-sleep periods, the specific shape of the RRI may be identified, for example, by employing at least one filter at a predetermined frequency threshold.

Thus, method 40 with its various steps, allows for a determination of many sleep stages and transitions of the sleeping subject, including: SWS, NSWS, SO, non-sleep, REM, LS, Stage-2 and Stage-1. One of ordinarily skill in the art would appreciate that the above sleep stages and transitions, as determined by methods 10, 20, 30 and 40, may also be used for determining all the sleep parameters which are presently measured in a standard PSG procedure. These parameters include, but are not limited to, sleep latency to SO, REM latency from SO to REM onset, sleep architecture (which is typically the percentage and absolute duration of LS, SWS and/or REM sleep), wake after SO, total sleep time, sleep efficiency (which is typically the ratio between the total sleep time and the time from the beginning to the end of the sleep study), and sleep fragmentation by arousals and awakenings (which is typically the ratio between the number of arousals and/or awakenings to the total sleep time).

A particular advantage of the present embodiments of the invention is that the number of leads which are used for the measurement procedure is much smaller than the number of leads in a standard PSG procedure. For example, all the above parameters may be determined using a single lead. It is to be understood, however, that using more than one lead is not excluded from the invention.

A detailed description of a method of obtaining the time-frequency decomposition, according to a preferred embodiment of the present invention, is now provided. The method, referred to herein as Selective Discrete Algorithm (SDA), was developed by Keselbrener L. and Akselrod S. and is found, e.g., in U.S. Pat. No. 5,797,840 and in an article entitled "Selective discrete Fourier transform algorithm for time-frequency analysis: Methods and application on simulated and cardiovascular signals" published in *IEEE Trans. Biomed. Eng.*, 43:789, 1996, both of which are hereby incorporated by reference.

The SDA is a variable window method for time-dependent spectral analysis. This algorithm has been extensively validated on physiological signals (e.g., physiological signals in humans modulated by the ANS) under a variety of transient conditions. Generally speaking, the power spectrum of physiological signals in humans modulated by the ANS can be divided into the VLF range (below 0.04 Hz), the LF range (from 0.04 Hz to 0.15 Hz) and the HF range (above 0.15 Hz displaying a peak at about 0.2 Hz for adults and a peak at about 0.4 Hz for children). The HF range is mediated by the fast reacting parasympathetic nervous system, the LF range is mediated by both the parasympathetic nervous system and the slower reacting sympathetic nervous system and the VLF range is mediated by thermoregulation and unknown systems.

The SDA is directed at determining the power content of frequencies of interest embedded in the physiological signal. The essence of the SDA derives from a basic rule according to which the amount of information which is required to estimate the power of fluctuations is a decreasing function of the frequency of interest. More specifically, in order to estimate the power of a high frequency fluctuation, only a short string of data is required, while a low frequency fluctuation demands a much wider time window.

Hence, according to a preferred embodiment of the present invention, a selective windowed time-frequency (t-f) analysis is performed for providing the time-dependent power spectrum of the RRI series. For each time of interest and for each frequency of interest, a minimal time-window is chosen over the relevant digitized signal, as further detailed hereinbelow. According to a preferred embodiment of the present invention, a series of windows are generated along the signal within which the power spectrum of the frequencies under investigation is to be analyzed. Then, the power spectrum for a particular frequency within each window is determined.

According to a preferred embodiment of the present invention, the duration of the windows is generally a decreasing function of the frequency under investigation, preferably inversely proportional to the frequency. Hence, low frequencies are investigated using long time windows while high frequencies are investigated using short time windows. The t-f analysis can be at a wide range of resolutions, both in frequency and in time. Typically, the frequency resolution is in the order of 0.005 Hz at the low frequency end of the spectrum, with time resolution in the order of one minute. For the higher frequency end, frequency resolution is in the order of 0.02 Hz with time resolution of a few seconds. The time and frequency resolutions preferably reach intermediate values around the center of the t-f plane.

The selective windowed t-f analysis may be implemented by more than one way, for example, in one embodiment a wavelet transform is used, in another embodiment a selective discrete spectral transform is used, and the like.

In the embodiment in which wavelet transform is used, the aperture, duration and the time resolution between consecutive windows are defined by a prototype function h(t), a scale parameter, a, and a shift parameter, b, according to the wavelet transform $\int h_{ab}(t)f(t)dt$. Further information on wavelet processing, is found in an article by Daubaechies I., entitled "The Wavelet Transform, Time Frequency Localization and Signal Analysis", published in *IEEE Transactions on Information Theory*, Vol. 36. No. 5, 1990 the contents of which are hereby incorporated by reference.

As well known in the art, for a large scale parameter value, the prototype function is stretched such that the prototype wavelet acts as a low frequency function while, for a small scale parameter value, the prototype function is contracted such that the wavelet function acts a high frequency function. Hence, depending on the value assigned to scaling parameter, a, the wavelet function dilates or contracts in time, causing the corresponding contraction or dilation in the frequency domain. Thus, the wavelet transform provides a flexible time-frequency resolution and analyzes higher frequencies with better time resolution but poorer frequency resolution than lower frequencies.

In the embodiment in which a selective discrete spectral transform is used, a predetermined number of data points are selected from the windows. Based on the data points, the power spectrum of the frequency within the windows is calculated, using a mathematical transform, which may be, for example, a Fourier transform, a Haar transform, a Hartley transform, a sine transform, a cosine transform, a Hadamard transform, and the like. According to a preferred embodiment of the present invention the data points are selected by employing a low pass filter and undersampling technique such as moving average. Typically, the same number of data points is provided, irrespective of the duration of the windows, so as not to generate artifacts or normalization problems.

As mentioned hereinabove, the duration of windows is preferably inversely related to the frequency under investigation. Depending on the type of the selective windowed t-f analysis which is used, the duration of windows typically lies from about 2 periods to about 10 periods of the frequency under investigation. The windows can have different apertures including, but not limited to, a rectangular aperture, a Hanmming aperture, a Hanning aperture, a Blackman aperture, a Gaussian window, a Lorentzian window, a sinc window, any power of a sine window, any power of a cosine window, any derivative of these windows, and the like.

Some corrections may be employed to the obtained power spectra, depending on the combination of the type of transform and the aperture of the window. For example, if the Fourier transform is used with a rectangular window, then, to ensure the highest possible frequency resolution by minimizing side lobes, the obtained power spectra are preferably corrected by dividing by the corresponding sinc function.

The calculated power spectra may be represented for example, in a 3D form, a 2D contour map form and the like. For example, if a power spectrum is represented by a 3D time dependent power spectrum graph, a first axis of the graph may represent frequencies, a second axis may represent time and a third axis may represent the power spectrum. Irrespective of the selected representation, the t-f resolution is substantially inhomogeneous, so that an optimal time-resolution is achieved for each frequency. Specifically, low frequencies have high frequency resolution and reduced time resolution, while high frequencies have lesser frequency and better time resolution.

While conceiving the present invention it has been realized that the sleep of a sleeping subject can be characterized using indices derived from the time-frequency decomposition.

Figure 5:
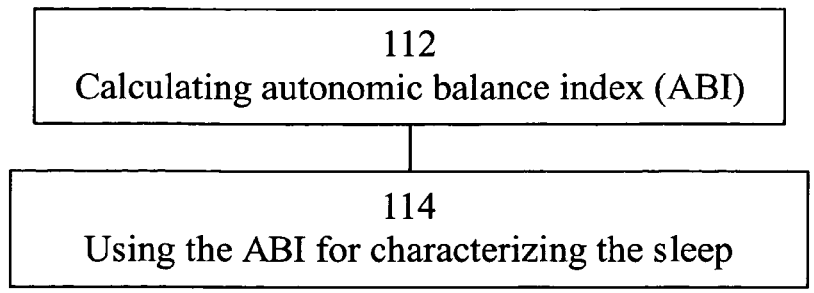
FIG. 5 is a flowchart of a method of characterizing a sleep of a sleeping subject, according to the present invention.

Hence, according to another aspect of the present invention, there is provided a method of characterizing a sleep of a sleeping subject. The method, generally referred to herein as method 110, is illustrated in the flowchart of FIG. 5. In a first step of method 110, designated by Block 112 at least one autonomic balance index (ABI), is calculated and in a second step, designated by block 114, the ABIs are used to characterize the sleep as further detailed hereinbelow.

According to a preferred embodiment of the present invention each ABI characterizes a different sleep stage and is calculated (e.g., by multiplication) using a weight of the sleep stage and at least one power parameter. According to a preferred embodiment of the present invention the power parameters may be, for example, the VLF, LF and HF power spectra. The power parameters may also be a combination (e.g., a ratio) between two of the VLF, LF and HF power spectra. The sleep stages can include any known sleep stage, such as, but not limited to, the sleep stages mentioned above.

Thus, according to a preferred embodiment of the present invention each the ABI has the following general from:

$$ABI_S = W_S P_S,$$

where the subscript S represents a particular sleep stage, W is the weight of the respective sleep stage and P is the power parameter.

The weight, W, may be the percentage of the sleep stage, S, from the entire sleep. For example, if the power parameter is the ratio LF/HF and an ABI of the REM sleep is to be calculated, then the percentage of the REM sleep from the entire sleep is multiplied by ratio LF/HF of the REM sleep.

According to a preferred embodiment of the present invention, for each power parameters, a total ABI may be calculated, e.g., using the equation:

$$ABI = \sum_S ABI_S,$$

where the summation is over a plurality of sleep stages, such as, but not limited to, LS, SWS and REM. Such a combination may be used to provide a general score of the entire sleep of the sleeping subject.

The ABI may be used for many applications in medicine for the purpose of quantifying a specific sleep stage and/or the entire sleep of a subject. The quantification may then be associated to certain observed sleep phenomena, and used for a comparison between different groups of subjects.

For example, the ABIs may be used for determining sleep apnea of the sleeping subject. As demonstrated in the example section that follows, there is a strong correlation between sleep apnea syndrome and the ABI of the present invention. Hence, according to a preferred embodiment of the present invention if one or more of the ABIs is larger than a predetermined threshold then an obstructive sleep apnea is determined. The predetermined threshold depends on the type of ABI which is used as the apnea discriminator. Typical values for this threshold include, without limitations, 0.05 for $ABI_{SWS}$ and 0.08 for $ABI_{wake}$, $ABI_{LS}$ and $ABI_{REM}$.

As stated, the present invention is also directed at determining body positions, e.g., for the purpose of identifying sleep disorders such as snoring, sleep apnea multiple body position changing and the like. It is recognized that there is a relationship between the QRS complex of the ECG signal and the anatomical position of the heart in the chest. A straightforward example is the effect of respiration, which modulates the angle of the mean electric axis of the heart, and can be applied (using two leads) to obtain an electrocardiogram-derived-respiration signal [Moody G. B. et al., "Derivation of respiratory signals from multi-lead ECGs", 1985, *Comp. Cardiol.*, 12:113-116].

While conceiving the present invention it has been hypothesized and while reducing the present invention to practice it has been realized that different body positions affect the shape of the QRS complex of the ECG signal, and, more particularly the width of the R-wave of the QRS complex.

Figure 6:
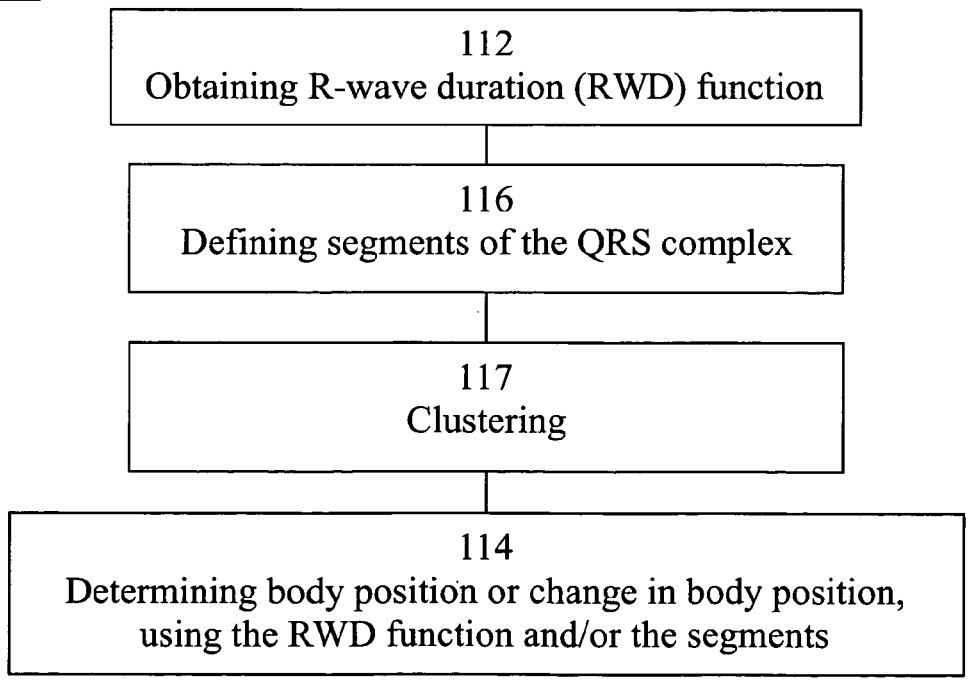
FIG. 6 is a flowchart of a method of determining a body position or a change in the body position of a sleeping subject, according to the present invention.

Hence, according to an additional aspect, there is provided a method of determining a body position or a change in the body position. The method, referred to herein as method 120 is illustrated in the flowchart of FIG. 6. Similarly to the above methods, the input to method 120 is series of signals of electrical activity recorded of the chest, as further detailed hereinabove. The body positions of the sleeping subject are then determined using information derived from these signals, preferably devoid of any visual means such as video camera and the like. The advantage of method 120 is the ability to combine the determination of body positions with other determinations (e.g., of the various sleep stages) in a single measurement. In addition, as further detailed hereinafter and demonstrated in the Examples section that follows, the method and its combining with the above methods can be fully automatic, so that the efforts to determine, for example, which sleep stage corresponds to which body position is minimized.

Referring to FIG. 6, in a first step of method 120, designated by Block 122, at least one R-wave duration (RWD) is extracted from the QRS complexes of the signals. The RWD may be extracted by any way known in the art. For example, a robust definition of the RWD, which can be applied to different shapes of QRS and represent a consistent characteristic of the QES complex is disclosed in an article by Shinar et al., entitled "R-Wave Duration as a Measure of Body Position Changes During Sleep" published in Computers in Cardiology 26:49-52 (1999), the contents of which are hereby incorporated by reference.

Figure 7:
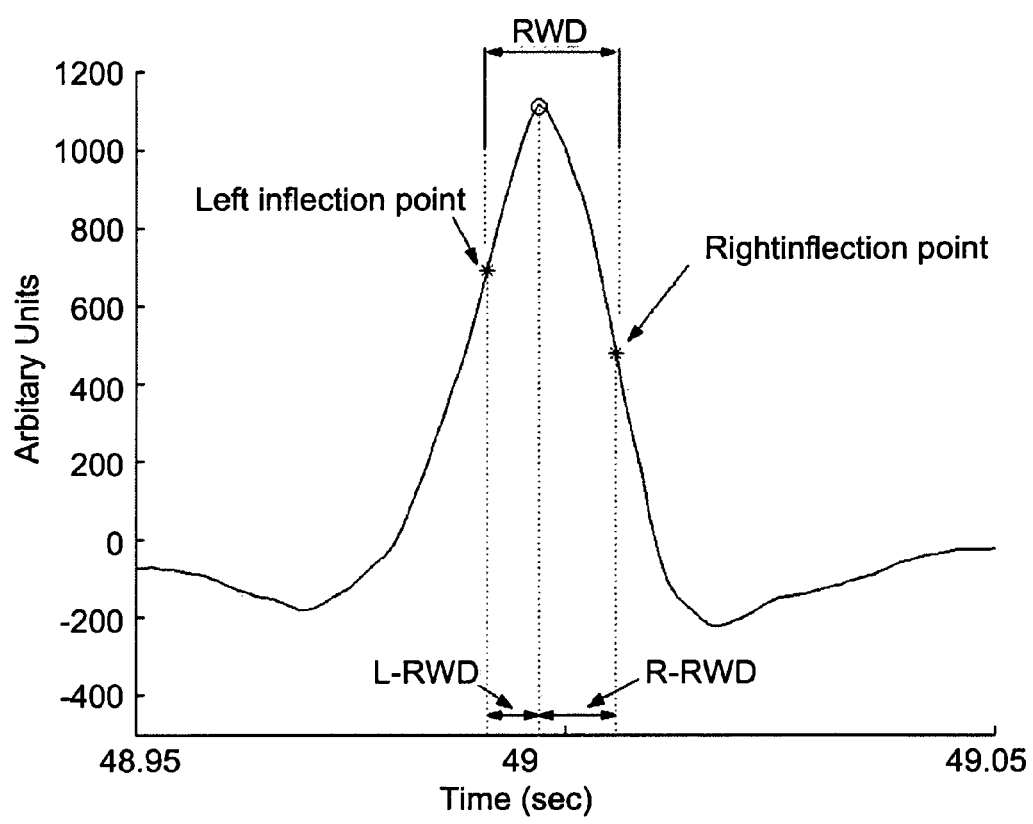
FIG. 7 shows a QRS complex, where two segments are defined for the R wave, a left segment, designated L-RWD and defined between the R wave peak (circle) and its left inflection point (asterisk), and a right segment, designated R-RWD and defined between the R wave peak and its right inflection point (asterisk); the R-wave duration, designated RWD is defined as between the two inflection points, according to the present invention.

FIG. 7, shows a typical QRS complex, where the peak of the R-wave is marked with a circle. Two inflection points are marked by asterisks to the left and the right of the peak. According to a preferred embodiment of the present invention the RWD is preferably defined as the time between two inflection points adjacent to the R-wave peak. It is to be understood, however, that any other definition of the RWD is within the scope of the present invention.

Irrespectively of the method by which the RWD is defined, once all the QRS complexes are processed, and for each complex, an RWD is extracted, an RWD function is defined.

As used herein, an RWD function refers to a mathematical quantity which returns, for each heart beat (i.e., for each instant of the sleep) the respective RWD. A typical graphical representation of the RWD function is exemplified in FIG. 35, in the Examples section that follows.

In a second step of method 120, designated by Block 114, the RWD function is used for determining the body position or the change in the body position of the sleeping subject.

It has been uncovered by the Inventors of the present invention that a sudden change in the RWD function corresponds to a change in the body position. Thus, according to a preferred embodiment of the present invention a change in the body position is defined when a change of RWD function is above a predetermined threshold. One way to determine a sudden change in the RWD function is by defining a moving window and calculating several statistical quantities (average, standard deviation, etc.) within the moving window, so that each QRS complex or a group of QRS complexes (e.g., an epoch of sleep) is characterized by a set of statistical quantities. The relations between the statistical quantities in the set are then used for determining whether or not a change in the body position has occurred.

For example, in one embodiment, two averages and two standard deviations are calculated separately within the left hand and the right hand sides of the moving window. Then, a change in the body position is identified if the difference between the two averages is larger than the sum of the two standard deviations. A skilled artisan will appreciate that other similar criteria may be used for locating a sudden change in the RWD function, such as, but not limited to, using a derivative of the RWD function or by transforming the RWD using a mathematical transform which is sensitive to sudden changes.

Additionally, as stated, the RWD function can be exploited for determining body position (rather than only a change in the body position). As demonstrated in the Examples section that follows, the RWD function may be exploited in more than one way to determine the body position of the sleeping subject. Although any individual may lie in many different positions while sleeping, in practice, for all presently known purposes, especially for diagnosis and study of sleep disorders, there is a discrete and finite number of body positions of interest. Hence, the ability of the QRS complex to serve as a discriminator between different body positions depends on the method by which this function is discretized. The Inventors of the present invention have found a unique method of discretizing the RWD function, by defining segments of the QRS complex and using these segments to span a well defined discrete basis of states, in which each state is representative of a different body position.

Hence, according to a preferred embodiment of the present invention method 120 further comprises an optional step, designated by Block 116, in which at least two segments are defined for each of the QRS complexes, so that each QRS complex is attributed to a set of segments, or, more particularly, to a set of widths, as each segment is characterized by its width.

It will be appreciated that the number of segments of each QRS complex and the number of leads, through which the QRS complexes are measured, determine the size of the discrete basis of state, hence the number of different states body positions which can be identified. Generally, as each QRS complex is attributed to a set of numbers, the entire data set is composed of multi-dimensional points. Such data set is not uniformly occupied by the multi-dimensional points. Instead, some regions in the space are sparse while others are crowded by clusters of points. The present invention successfully exploits this non-uniformity for the purpose of identifying body position, whereby each cluster corresponds to one body position, and the points (i.e., the QRS complexes) are identified according to the cluster to which they belong. The procedure for identifying the sparse and the crowded regions, and discovering the overall distribution patterns of the dataset is known in the art as clustering.

Hence, according to a preferred embodiment of the present invention method 120 also comprise an optional step, represented by Block 117, in which a clustering procedure is applied on the set of widths, so as to so as to define a plurality of clusters, where each cluster corresponding to a different body position. Any clustering procedure may be used, either manual (e.g., by visual means) or automatic, using a data processor and an appropriate algorithm.

Clustering methods are known, and are typically based on a variety of mathematical and/or physical principles. Representative examples include, without limiting, graph theory methods, density estimation methods (e.g., scale-space), Potts-spins-based methods, hierarchical methods (e.g., nearest neighbor, minimal spanning tree), partitional methods (e.g., K-means, adaptive K-means, hard/fuzzy C-means) and the like.

For simplicity, suppose that the widths of the segments are classified in a binary fashion, using a single threshold, so that when a width is above the threshold, it is said to be "high" and if it is below the threshold it is said to be "low". For a single lead and k segments for each QRS complex, the number of possible states is $2^k$. Using two leads will square this number. Furthermore, classifying the width using two thresholds (e.g., "low", "medium", "high"), results in $3^k$ states for each lead, and so on.

In its simplest usage, each QRS complex is comprised of one segment which is the RWD. Thus, in this embodiment, the RWD function, as defined above, may serves as a "two-state discriminator," capable of distinguishing between two states. For example, RWD function can determine whether the subject is lying on the side (a first body position) or the subject is prone or supine (a second body position). According to a preferred embodiment of the present invention a high value of the RWD function characterizes a prone or a supine body position, whereas a low value of the RWD characterizes a side body position. It is to be understood that the interpretation of the relative terms "high" and "low" depends on the typical value of the RWD function as calculated from the signals measured of the chest of the subject (see, e.g., FIG. 35 in the Examples section that follows). For example, a high/low value of the RWD function can be a value which is higher/lower than the median or the average of the RWD over a predetermined window. A typical threshold between the "high" and the "low" values is about 10.5 milliseconds.

For more than two body position, as stated, more leads may be used and/or more segments may be defined, so that a set of numbers (rather that a single RWD value) is attributed to each QRS complex.

According to a preferred embodiment of the present invention the segments of the QRS complexes are defined, similarly to the definition of the RWD above, using derivatives of the R-wave. More specifically, the endpoints of the segments are preferably characterized by a zero nth-order derivative of a respective R-wave, where n is a positive integer. For example, referring again to FIG. 7, if there are two segments for a specific R-wave, then one endpoint of the segments is characterized by a zero second derivative (inflection point) and the other endpoint is characterized by a zero first derivative (a peak). More segments can be defined using higher order derivatives of the R-wave.

As a representative example, consider the above case of two segments. In this embodiment, each QRS complex is attributed to a left segment, referred to herein as L-RWD, and a right segment, referred to herein as R-RWD so that, for a single lead and a binary characterization of the widths, there are $2^2=4$ states ("high", "high"), ("low", "high"), ("high", "low"), and ("low", "low"), corresponding to four body positions, as follows: (i) the subject is prone when both L-RWD and R-RWD have high values; (ii) the subject lies on his right side when L-RWD is low and R-RWD is high; (iii) the subject lies on his left side when L-RWD is high and R-RWD is low; and (iv) the subject is supine when both L-RWD and R-RWD have low values.

The present invention successfully provides a method of determining a sleep apnea, generally referred to herein as method 130, which, in one embodiment, may exploit the knowledge of the body position of the sleeping subject.

Figure 8:
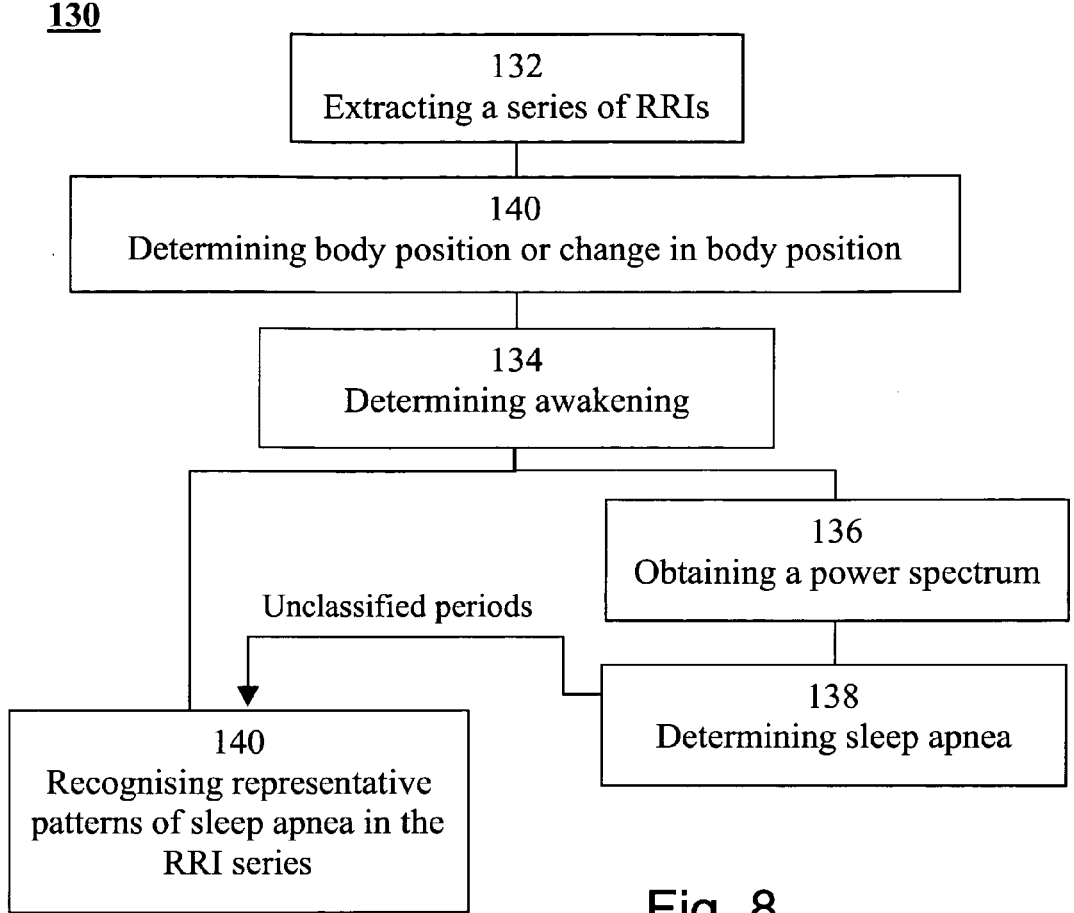
FIG. 8 is a flowchart of a method of determining a sleep apnea, according to the present invention.

Reference is now made to FIG. 8, which is a flowchart of method 130, according to a preferred embodiment of the present invention.

In a first step of method 130, designated by Block 132, an RRI series is extracted from signals of electrical activity recorded of a chest of a sleeping subject, as further detailed hereinabove, e.g., with respect to the first step of method 10. Prior to the step of extracting the RRI series, an optional step of interpolation of the input signals may be performed, so as to compensate missing heart beats of the sleeping subject.

In a second step, designated by Block 134, awakening periods of the sleeping subject are determined so as to exclude RRI corresponding to awakening periods from the RRI series. The removal the awakening periods, serves for minimizing misclassification of wake events as apnea event. The determination of wakening periods may be done in any way known in the art, for example, using a low-pass-filter, as further detailed hereinabove, with respect to the fourth step of method 40. A representative example for detecting wakening periods is provided in the Examples section that follows (see Example 4).

In a third step, designated by Block 136 a power spectrum is obtained from the RRI series, preferably by a discrete transform. Either a steady state of a time-dependent discrete transform may be used. Examples of discrete transforms which may be used include, but are not limited to, Fourier transform, Hartley transform, sine transform, cosine transform, Hadamard transform, Haar transform and wavelet transform.

Typically, apnea events occur at a frequency ranging from about 0.01 Hz to about 0.04 Hz. Thus, according to a preferred embodiment of the present invention the power spectrum obtained in the third step of the method preferably includes a power spectrum component at a frequency range representing sleep apnea, e.g., 0.01-0.04 Hz (corresponding to apnea events of 25-100 seconds). High power in this range is characteristic of recurrent apneas cycle, and is indicative of the presence respiratory disturbance events in the entire period of interest.

In a fourth step of method 130, designated by Block 138, the power spectrum is used to determine the sleep apnea of the sleeping subject. This may be done by comparing the above power spectrum component to a predetermined threshold (e.g., the total power or a predetermined portion thereof), so that if the power spectrum component is above the threshold, then the respective sleep epoch is identified as an apnea event.

The above method successfully detects multiple apnea events by means of power spectral analysis of the RRI. However, as apnea is a position related syndrome, it is recognized that it is important to classify the apneic events of a specific subject according to his recumbent body position, for example for selecting an appropriate treatment.

As stated, method 130 successfully correlates between the body position of the sleeping subject and the suspected algorithm. Thus, according to a preferred embodiment of the present invention the method further comprises an optional step, designated by Block 140, in which body positions or a change in the body position of the sleeping subject are determined, prior to the second step (Block 134). This step may be done either using a conventional method (e.g., by visual means) or by method 120 as further detailed hereinabove. Once the body positions of the sleeping subject are known, all the epochs of the sleep are preferably divided, so that the above steps of the method are executed separately for each one of body positions. In other words, if the entire sleep time contains n epochs, and it was found that there were p position changes throughout the sleep, then the dataset is divided into p+1 subsets: $n_1, n_2, \ldots, n_{p+1}$, where $n_1+n_2+\ldots+n_{p+1}=n$. Each subset is treated separately, generally by executing the steps designated by Blocks 132, 134, 136 and 138.

One will appreciate that for long enough subsets (e.g., subsets having a duration longer than about 200 seconds), the above method steps can be executed without any modification. On the other hand, the duration of some of the above subsets, especially once the awakening periods are excluded therefrom, may be too short for obtaining a reliable discrete transform.

The present invention successfully provides an additional step for detecting sleep apnea, which may be used either independently, or, more preferably as a supplementary step for method 130, for the purpose of detecting apnea events, occurring, e.g., in short duration subsets. This embodiment is also useful for detecting sporadic apnea events in long duration subsets which were not classified as apneic using the power spectrum.

Thus, according to a preferred embodiment of the present invention, method 130 comprises an optional step, designated by Block 140, in which a pattern recognition procedure is employed on a portion of the RRI series, so as to identify representative patterns of sleep apnea. It was found by the Inventors of the present invention that apnea events are represented by a decrease followed by a rapid increase in RRI. Thus, according to a preferred embodiment of the present invention the representative patterns are characterized by a U-shape of the RRI series. Any pattern recognition procedure may be employed for detecting the U-shape patterns. One way is to detect transient decreases in the RRI below a predetermined threshold.

Figure 9:
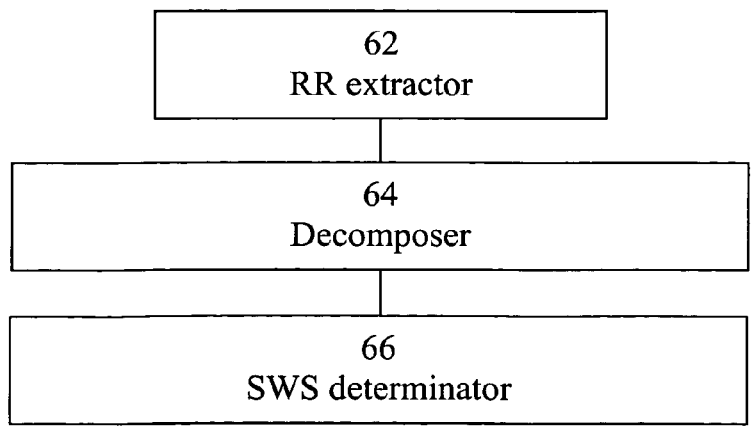
FIG. 9 is a schematic illustration of an apparatus for determining a SWS period and a NSWS period from signals of electrical activity recorded of a chest of a sleeping subject, according to the present invention.

Reference is now made to FIG. 9 which illustrates an apparatus for determining an SWS period and a NSWS period from signals of electrical activity recorded of a chest of a sleeping subject, according to an additional aspect of the present invention. The apparatus comprising an R-R extractor 62 for extracting a series of RRI from the signals, a decomposer 64 for obtaining a time-frequency decomposition from the RRI series and an SWS determinator 66, for determining the SWS period using the time-frequency decomposition, as further detailed hereinabove, with respect to method 10.

Figure 10:
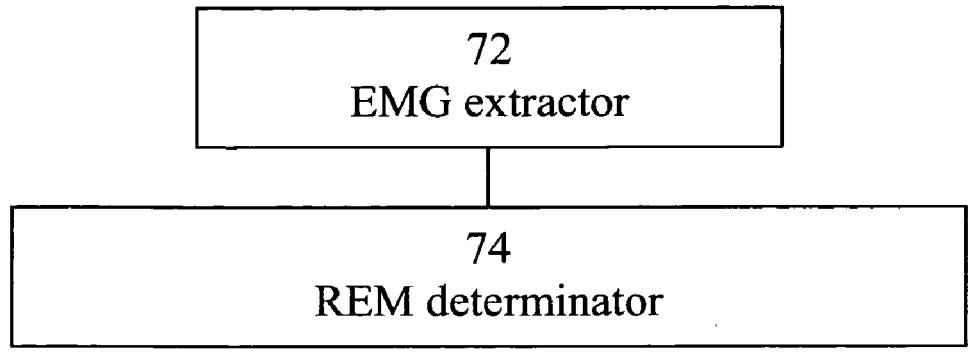
FIG. 10 is a schematic illustration of an apparatus for determining a REM sleep and a NREM sleep from signals of electrical activity recorded of a chest of a sleeping subject, using a plurality of electromyogram parameters, according to the present invention.

Reference is now made to FIG. 10 which illustrates an apparatus for determining a REM sleep and a NREM sleep from signals of electrical activity recorded of a chest of a sleeping subject, according to yet another aspect of the present invention. The apparatus comprising an EMG extractor 72 for extracting a plurality of EMG parameters from the signals, a REM determinator 74 for using the plurality of EMG parameters to determine the REM sleep and the NREM sleep of the sleeping subject, as further detailed hereinabove, with respect to method 20.

Figure 11:
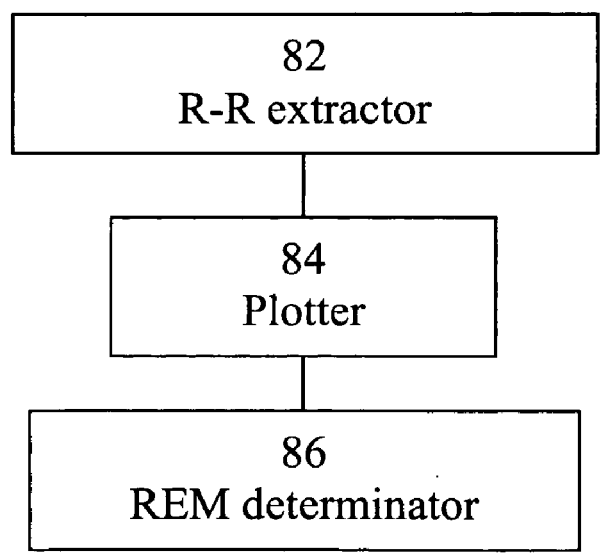
FIG. 11 is a schematic illustration of an apparatus for determining a REM sleep and an NREM sleep from signals of electrical activity recorded of a chest of a sleeping subject, using a Poincare plot, according to the present invention.

Reference is now made to FIG. 11 which illustrates an apparatus for determining a REM sleep and an NREM sleep from signals of electrical activity recorded of a chest of a sleeping subject, according to still another aspect of the present invention. The apparatus comprising an R-R extractor 82, for extracting a series of cardiac R-R intervals from the signals, a plotter 84, for constructing a Poincare plot of the series of cardiac R-R intervals, and a REM determinator 86, for using the Poincare plot to determine the REM sleep and the NREM sleep of the sleeping subject, as further detailed hereinabove, with respect to method 30.

Figure 12:
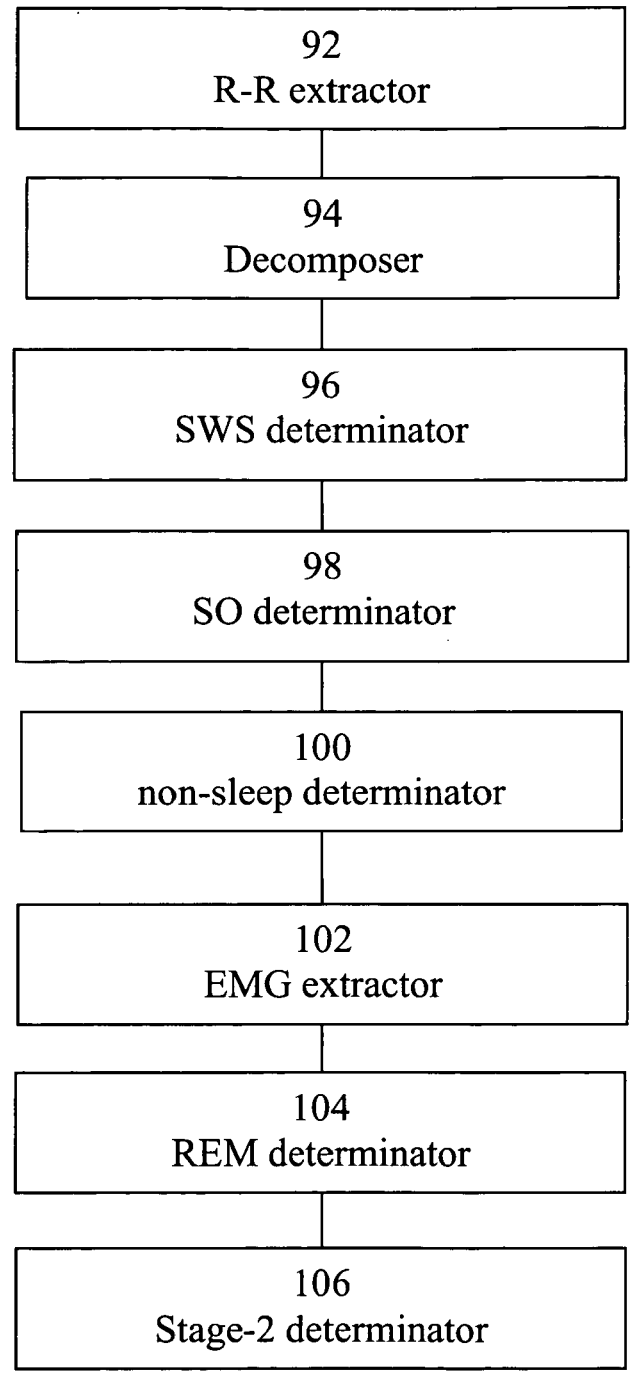
FIG. 12 is a schematic illustration of an apparatus for determining various sleep stages from signals of electrical activity recorded of a chest of a sleeping subject, according to the present invention.

Reference is now made to FIG. 12 which illustrates an apparatus for determining sleep stages from signals of electrical activity recorded of a chest of a sleeping subject, according to still a further aspect of the present invention. The apparatus comprising an R-R extractor 92 for extracting a series of cardiac R-R intervals from the signals and a decomposer 94, for obtaining a time-frequency decomposition from the series of cardiac R-R intervals. The apparatus further comprises an SWS determinator 96, an SO determinator 98 for determining at least one SO period, a non-sleep determinator 100 for determining plurality of non-sleep periods. The apparatus further comprises an EMG extractor 102, for extracting a plurality of EMG parameters from a portion of the signals. The portion corresponds to a NSWS period other than the SO periods and other than the non-sleep periods. The apparatus further comprises a REM determinator 104 for using the plurality of EMG parameters to determine at least one REM period, thereby to obtain also at least one LS period which is defined as a NSWS period other than the SO periods, other than the non-sleep periods and other than the REM periods. According to a preferred embodiment of the present invention the apparatus further comprises a Stage-2 determinator 106 for determining, from a portion of the LS periods, at least one Stage-2 period, hence the apparatus also obtain a Stage-1 period which is defined as LS periods other the Stage-2 periods. The operations of the apparatus are similar to the operations and steps described hereinabove with respect to method 40.

Figure 13:
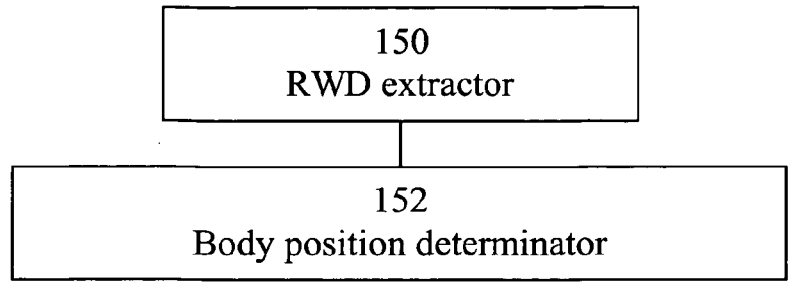
FIG. 13 is a schematic illustration of an apparatus for determining a body position or a change in the body position from signals of electrical activity recorded of a chest of a sleeping subject, according to the present invention.

Reference is now made to FIG. 13 which illustrates an apparatus for determining a body position or a change in the body position from signals of electrical activity recorded of a chest of a sleeping subject, according to still another aspect of the present invention. The apparatus comprising an RWD extractor 150 for extracting RWDs hence obtaining an RWD function, and body position determinator 152 for determining the body position or the change in the body position of the sleeping subject using the RWD function obtained by extractor 150, as further detailed hereinabove, with respect to method 120.

Figure 14:
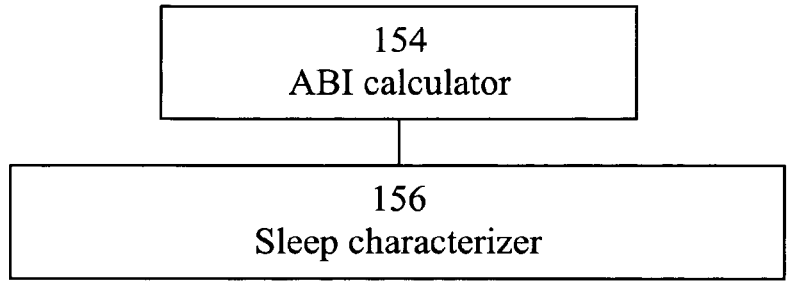
FIG. 14 is a schematic illustration of an apparatus for characterizing a sleep of a sleeping subject, according to the present invention.

Reference is now made to FIG. 14 which illustrates apparatus for characterizing a sleep of a sleeping subject, according to still another aspect of the present invention. The apparatus comprising an ABI calculator 154, for calculating at least one ABI, defined as further detailed hereinabove, and a sleep characterizer 156 for characterizing the sleep of the sleeping subject using the ABI calculated by calculator 154.

Figure 15:
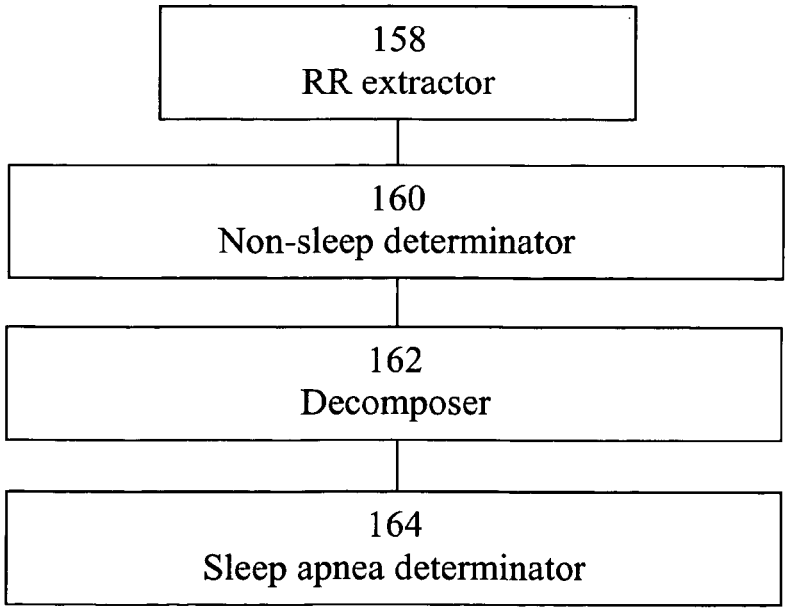
FIG. 15 is a schematic illustration of an apparatus for determining a sleep apnea from signals of electrical activity recorded of a chest of a sleeping subject, according to the present invention.

Reference is now made to FIG. 15 which illustrates an apparatus for determining a sleep apnea from signals of electrical activity recorded of a chest of a sleeping subject, according to still another aspect of the present invention. The apparatus comprising an R-R extractor 158 for extracting a series of RRIs from the signals, a non-sleep determinator 160 for determining awakening periods of the sleeping subject and excluding RRIs corresponding to the awakening periods from the RRI series, a decomposer 162 for calculating a power spectrum from the RRI series, and a sleep apnea determinator 164 for using the power spectrum obtained by decomposer 162 and determining the sleep apnea of the sleeping subject. The operations of the apparatus are similar to the operations and steps described hereinabove with respect to method 130.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Additional objects, advantages and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples which, together with the above descriptions, illustrate the invention in a non limiting fashion.

Example 1

SWS Detection

In this study the behavior of the autonomic nervous system at SWS was investigated, using time dependent power spectrum analysis.

Experimental Methods

The study was performed on 34 adult subjects. The subjects were 35±15 of age, 20 of which were males and 14 females. The subjects were arbitrarily selected from a typical adult population referred to a sleep study for a multitude of reasons. Children under 15 years of age and subjects with a heart related disease were rejected. Data from 17, arbitrarily chosen, subjects served as a training set and the other half served as a test set.

For the purpose of validating the method and to compare the results with other methods standard PSG data were also collected.

Hence, the subjects underwent a full sleep study including recordings of the following signals: 2 central EEG (digitized at 100 Hz), 2 occipital EEG (digitized at 100 Hz), chin and tibialis EMG (digitized at 100 Hz), left and right EOG (digitized at 100 Hz), ECG (digitized at 200 Hz), abdomen and thorax effort (digitized at 10 Hz), oxygen saturation (digitized at 1 Hz) and nasal air flow (digitized at 100 Hz).

The PSG data were monitored off-line and sleep stages were determined according to standard R&K criteria by a sleep expert, to provide a reference against which the automated SWS detection method was examined.

The method consisted the steps described in method 10, where the time frequency decomposition was obtained using a wavelet transform and the power components were the VLF power (0.005-0.04 Hz), the LF power (0.04-0.15 Hz) and the HF power (0.15-0.45 Hz). The RRI series was obtained by a computer-scan for peak detection.

Experimental Results

Figure 16:
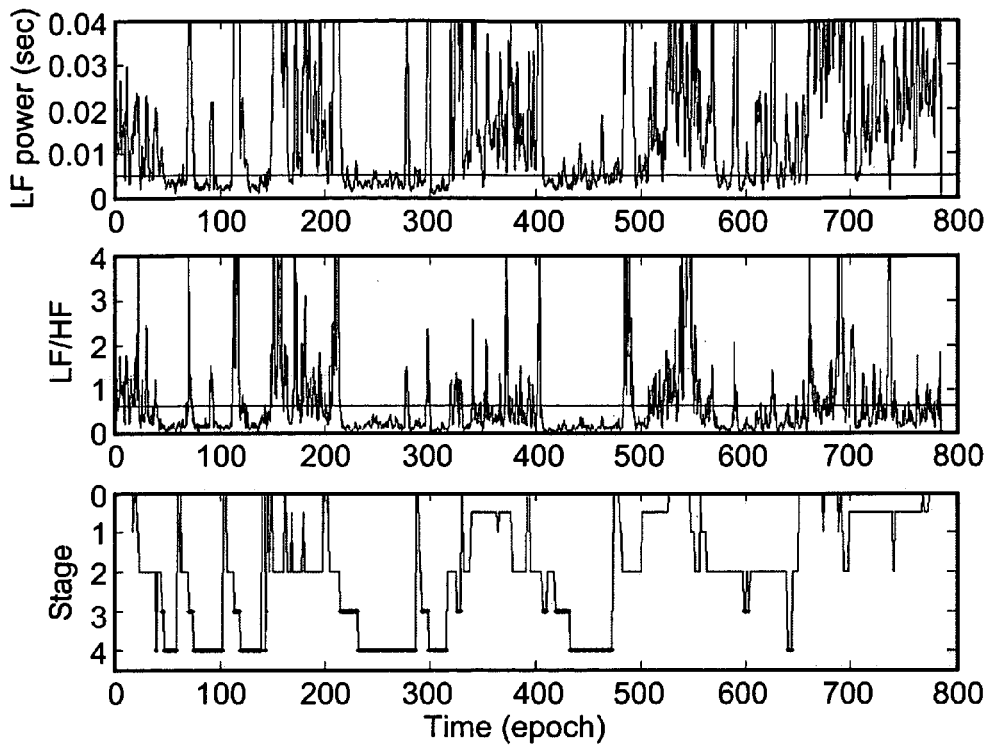
FIG. 16 shows the output of the wavelet transform of the RRI series of one subject, together with the sleep stages as determined by standard criteria.

Reference is now made to FIG. 16, which shows the output of the wavelet transform of the RRI series of subject L03, together with the sleep stages as determined by standard R&K criteria. Shown in FIG. 16 are graphs representing the time dependence of the LF power, the powers ratio LF/HF and the sleep stages as determined by the sleep expert. The time unit on the graphs is 30 seconds per one sleep epoch. The SWS period, corresponding to stages 3 and 4 are marked bold. As can be seen from FIG. 16, during SWS, the LF/HF ratio and LF power reach lowest values.

Table 1 below shows average absolute power values and standard deviation of the VLF, LF and HF powers detected during SWS, LS and REM sleep.

TABLE 1

|     | SWS           | LS            | REM           |
|-----|---------------|---------------|---------------|
| VLF | 0.014 ± 0.009 | 0.031 ± 0.021 | 0.036 ± 0.026 |
| LF  | 0.010 ± 0.009 | 0.020 ± 0.015 | 0.021 ± 0.013 |
| HF  | 0.013 ± 0.014 | 0.016 ± 0.016 | 0.015 ± 0.013 |

Average LF power and HF power during SWS have shown significant decrease ($p<0.001$, $p<0.05$ respectively) for all subjects, using one-tail-paired t-test. As can be seen from Table 1, the VLF power exhibits a similar significant decrease in power during SWS.

Figure 17:
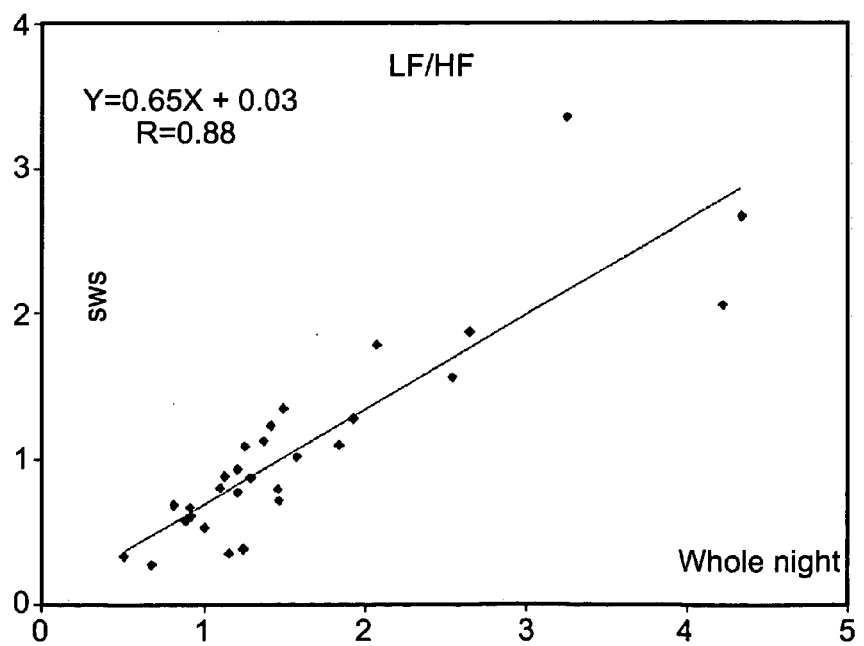
FIG. 17 shows average LF/HF ratio during SWS, as a function of the average LF/HF ratio throughout the entire night.

Reference is now made to FIG. 17 which shows the average LF/HF ratio during SWS, as a function of the average LF/HF ratio throughout the entire night. Each subject is represented by one point in FIG. 17. The solid line is a regression line of $Y=0.65X+0.03$. As can be seen from FIG. 17, there exists a substantial linear relation between the average LF/HF ratio during SWS, and the average LF/HF ratio throughout the night. This relation was used to predict the expected LF/HF balance during SWS from the average balance values during the night. Similar relations (but with different slope values) exist between the balance during other sleep stages and whole night average. A summary of these results is given in Table 2.

TABLE 2

|  | LF/HF | VLF/HF |
|---|---|---|
| SWS vs. Whole night | y = 0.65x + 0.03 (R = 0.88) | y = 0.52x + 0.14 (R = 0.91) |
| LS vs. Whole night | y = 1.01x + 0.02 (R = 0.98) | y = 0.84x + 0.31 (R = 0.95) |
| REM vs. Whole night | y = 1.35x − 0.27 (R = 0.89) | y = 1.33x − 0.31 (R = 0.84) |

The SWS was determined by selecting epochs in which the balance between the locally averaged LF or VLF power and the locally averaged HF power are below a threshold determined for each subject, using the linear regression. In addition, the SWS epochs were further filtered by a requirement that LF or VLF power was within the lower third of values. This is in accordance with the significant LF and VLF power decrease during SWS, and in accordance with a typical abundance of SWS, which is about one quarter of total sleep time.

Comparing the results as obtained by method 10, to the manually detection of the sleep expert results in an 82% and 80% matching in the training set and test set, respectively. Most of the missed classifications (13% out of 19% in test set) of NSWS were during Stage-2, typically at the second half of night. A comparison between the standard R & K classification and the results of the test set is presented in Table 3.

TABLE 3

| R & K Algorithm results | SWS | Non-SWS (stage 2) |
|---|---|---|
| SWS | 78 | 19 (13) |
| Non-SWS | 22 | 81 |

Example 2

REM Detection Using Poincare Plot

In this study the behavior of the autonomic nervous system during REM sleep was investigated, using Poincare plots of RRI series.

Experimental Methods

The study was performed on ten healthy subjects (7 males and 3 females) without any known sleep problem. For the purpose of validating the method and to compare the results with other methods, standard PSG data were also collected for two consecutive nights.

Hence, the subjects underwent a full sleep study including recordings of the following signals: two central and two occipital EEG leads (digitized at 100 Hz), two eye movement leads (digitized at 100 Hz), submental EMG (digitized at 100 Hz), leg movement (digitized at 10 Hz), nasal airflow (digitized at 100 Hz), end-tidal $CO_2$ (digitized at 12.5 Hz), oxygen saturation and pulse waveform (digitized at 1 Hz), and chest and abdominal effort (digitized at 10 Hz).

The PSG data were monitored off-line and sleep stages were determined according to standard R&K criteria by a sleep expert, to provide a reference against which the automated REM detection method was examined. The ECG signal was digitized at 200 Hz and scanned to detect and record the RRI series.

The procedure was according to method 30, i.e., using a Poincare plot, were a two-beat gap was selected for constructing the Poincare plot, and a two-minutes time window was selected was selected for calculating the moments. The calculated moments were selected to be moments-of-inertia with respect to the x=y axis of the Poincare plot, as further detailed hereinabove. Points for which the distance, D, from the x=y axis was above the average of absolute D plus one standard deviation were excluded from the calculations. In addition, a normalization procedure was employed by dividing each moment-of-inertia by the total number of accepted points.

Experimental Results

Figure 18A:
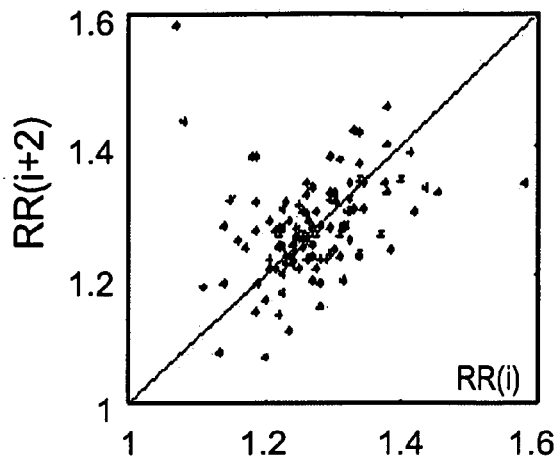
FIGS. 18a-c show typical Poincare plots for two minutes data, which, were identified as REM sleep.

FIG. 18a shows a typical Poincare plot for two minutes data, which, according to R&K criteria, were identified as REM sleep, along with the x=y axis. As can be seen, the Poincare plot of FIG. 18a is elongated with few extreme points that are far of the x=y axis.

Figure 18B:
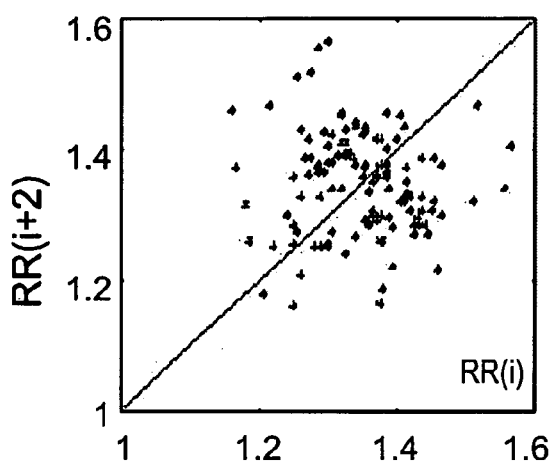

FIG. 18b shows a typical Poincare plots for other two minutes data, which, according to R&K criteria, were identified as light-sleep. FIG. 18b has more circular symmetry than FIG. 18a.

Hence, on the average, and excluding points which are far from the x=y, REM periods are characterized by a significantly lower moments-of-inertia than LS periods.

Figure 18C:
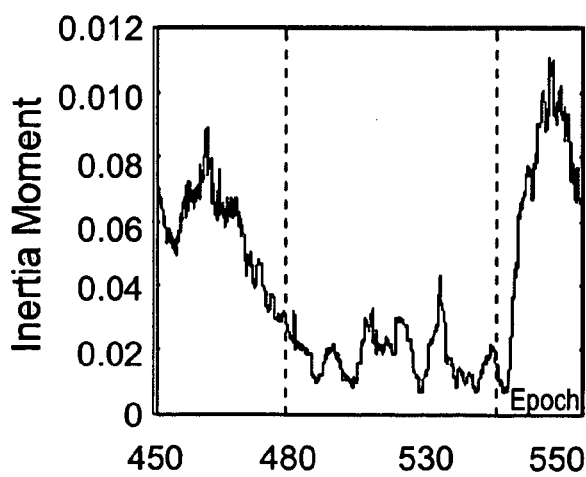

FIG. 18c shows a graph of the calculated moments-of-inertia as a function of time, measured in units of epochs. Each epoch corresponds to 30 seconds. According to R&K criteria the first 479 epochs are scored as stage 2, the epochs 480-531 are scored as REM, the epochs 532-538 are scored as wake, the epochs 539-546 are scored as Stage-1, and the epochs thereafter are scored as stage 2. The REM period is marked on FIG. 18c by two vertical dashed lines. As can be seen from FIG. 18c, more than 70% of the REM episodes had significantly lower inertia moment than other sleep stages. No significant difference between the detection rate for the first and second night was found.

Example 3

SO Detection

In this study the behavior of the autonomic nervous system at sleep onset was investigated, using time dependent power spectrum analysis.

Experimental Methods

The study was performed on thirteen healthy young subjects without any known cardiac, respiratory or neurological problems. The subjects underwent two whole night sleep studies. From the thirteen subjects, eight subjects (ages 22±5) who had no sleep related problem, and a long enough time period before SO to allow time-dependent spectral analysis, were included in this study.

For the purpose of validating the method and to compare the results with other commonly employed methods, standard PSG data were also collected.

Hence, the subjects underwent a full sleep study including recordings of the following signals: 2 central EEG (at 100 Hz), 2 occipital EEG (digitized at 100 Hz), EOG and chin EMG (digitized at 100 Hz), ECG (digitized at 200 Hz) and abdominal and chest respiratory effort, nasal and oral airflow, end-tidal $CO_2$, leg movement, oxygen saturation and pulse wave, (all of which digitized at 12.5 Hz).

The PSG data were monitored off-line and sleep stages were determined according to standard R&K criteria by a sleep expert, to provide a reference against which the automated SO detection method was examined. In addition, the PSG data were screened for any respiratory abnormalities, so as to exclude subjects with abnormal sleep characteristics from the study. In the standard R&K criteria, SO was defined as the first of two consecutive NREM Stage-1 epochs or the first epoch of any other sleep stage. Each epoch corresponds to 30 seconds.

The procedure included the following steps in which in a first step a steady state power spectrum analysis of HR and respiratory data was performed, for preliminary identification of the respiratory peak in the HR spectrum of each subject.

In this step, the RRI were converted into HR, with a uniform sampling at 10 Hz. For further details on converting RRI into HR, the reader is referred to Berger, R. D. et al., "An efficient algorithm for spectral analysis of heart rate variability", *IEEE Trans. Biomed. Eng. BME*-33, 900-904, 1986. Eight minutes data segments of the HR series were processed using a discrete Fourier transform from 4 minutes before SO to 4 minutes after SO, as determined by the standard R&K criteria. This step further included selecting one respiratory channel (out of the airflow channel and the two breathing effort channels) that had minimum acquisition artifacts. The chosen respiratory channel was analyzed using SDA around the time interval of the SO, so as to identify the main respiratory peak. In addition, the respiratory spectrum was compared to the HR spectrum so as to identify the respiratory peak in the HR spectrum.

In a second step, two thresholds were calculated as further detailed herein. The first threshold was calculated by separating the low-frequency peak from the mid-frequency peak, using the minimum-cross-entropy threshold algorithm. This algorithm was applied on the frequency range from 0.04 Hz and to the minimum value between the mid and high frequency peaks. The first threshold was then used for determining the second threshold as follows. Hence, the second threshold was calculated by separating the mid-frequency peak from the high-frequency peak, again, using the minimum-cross-entropy threshold algorithm. For the second threshold, this algorithm was applied on the frequency range from first threshold to 0.5 Hz.

In a third step, a time-frequency decomposition of the instantaneous HR data was obtained, which decomposition was further integrated according to the thresholds which were calculated in the second step. The time-frequency decomposition was performed using a 2-second time resolution. The procedure was bounded to the frequency range of 0-0.5 Hz, while for each frequency a time window of 10 periods was selected, thus a variable window width for each frequency was obtained. Once the time-frequency decomposition was calculated and integrated, the following ratios between integrated quantities were calculated: LF/T, HF/T and LF/HF, where T represents the integrated total power. Thus, this step defines six SO parameters: three HRV measures (LF, HF and T), a sympathetic power LF/T, a parasympathetic power HF/T and sympathovagal balance LF/HF, all of which are integrated quantities.

In a fourth step the SO parameters were normalized and further analyzed statistically as follows. The SO parameters were first averaged over one minute periods, starting 5 minutes before and finishing 9 minutes after SO. This resulted in 6 sets (T, LF, HF, LF/T, HF/T, and LF/HF) of 15 repeated measurements for each subject, around SO. For normalization of these sets of variables, the average of each variable was used as its own normalization factor, for each subject. One would appreciate that normalization before averaging over all subjects, minimizes effects of inter-subject variation of HRV power and ratio values. The statistical analysis included one-way repeated measures ANalysis-Of-VAriance (ANOVA) so as to examine the behavior of the log of the power and the log of the ratios of different frequency bands. This statistical analysis was performed separately before and after SO. An additional statistical analysis included a one tailed paired t-test for further examination of the type of behavior. Finally, all the normalized variables were averaged over all subjects.

Experimental Results

Figure 19:
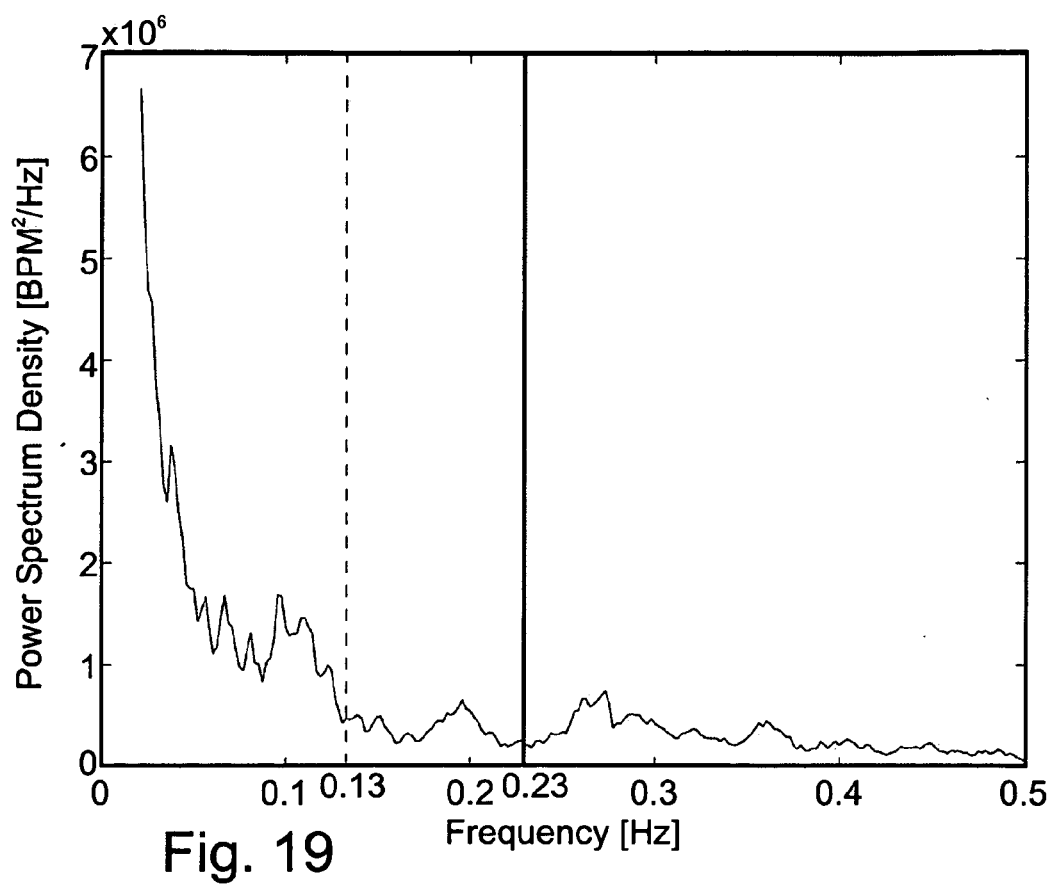
FIG. 19 shows the steady state power spectrum and the frequency thresholds for a single subject calculated for a first sleep onset study detailed in Example 3, below.

FIG. 19 shows the steady state power spectrum and the frequency thresholds for a single subject. The first and the second thresholds are represented in FIG. 19, respectively, as a dashed vertical line at 0.13 Hz and a solid vertical line at 0.23 Hz. The respiratory rate for this subject, extracted with the time-dependent analysis, was found instable during the analyzed period, yet remained within the boundaries of the HF band. This instability caused the relative widening of the respiratory (HF) range seen in FIG. 19, and was common to all subjects in this study. The power peak at about 0.2 Hz may be attributed to a superposition of the shoulders of the LF and HF peaks. This peal may also be attributed to a harmonic of the peak at about 0.1 Hz, although in other subjects this peak did not appear at a multiple frequency of the low-frequency peak. One would appreciate that this peak, being at a frequency location which varies from one subject to another, would have been ignored if arbitrary limits were predetermined for the frequency bands.

Figure 20A:
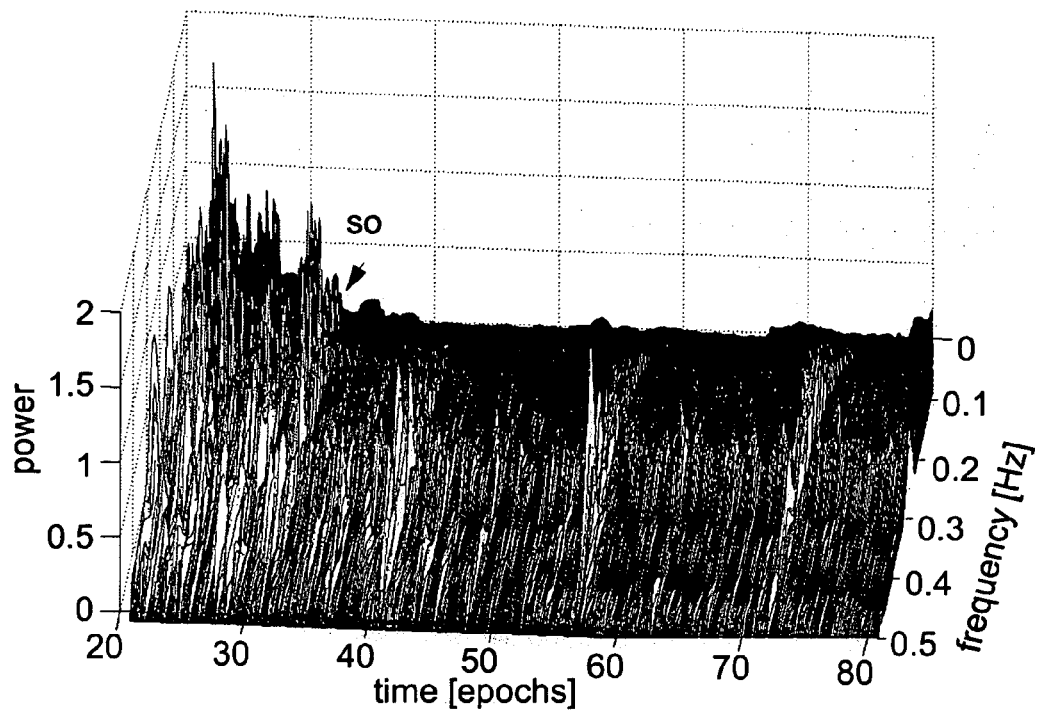
FIG. 20a is a three-dimensional plot of the time-frequency decomposition as obtained by the SDA, at a time range of 80 epochs from the beginning of the sleep study calculated for the first sleep onset study of Example 3.
Figure 20B:
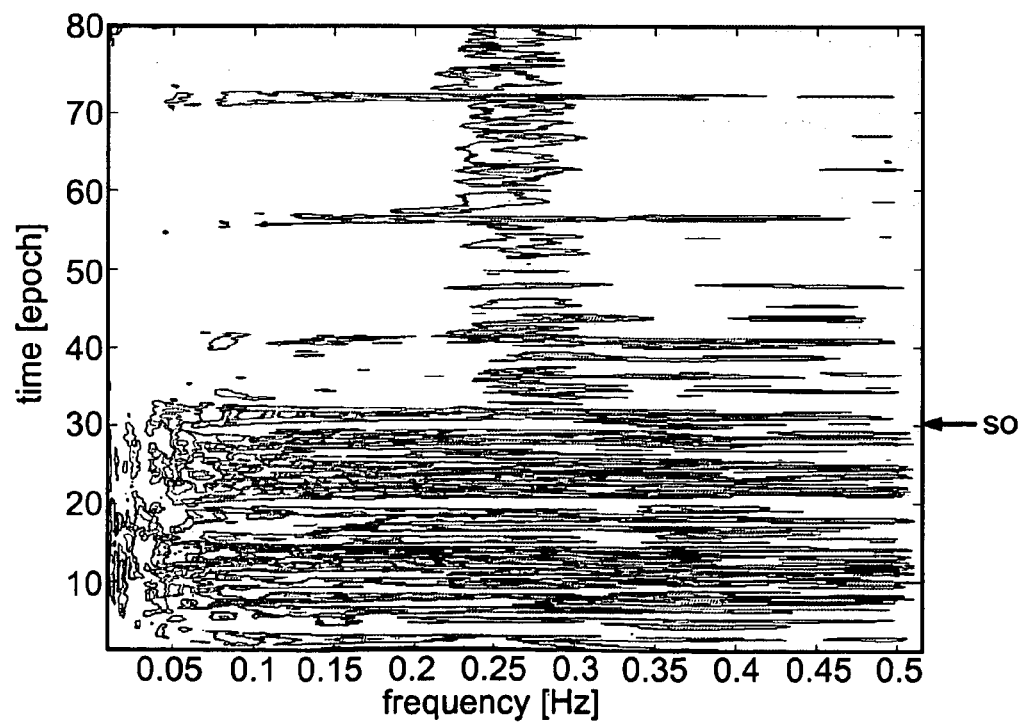
FIG. 20b is a contour plot of the time-frequency decomposition as obtained by the SDA, at a time range of 80 epochs from the beginning of the sleep study calculated for the first sleep onset study of Example 3.

FIGS. 20*a* and 20*b* are a three-dimensional plot and a contour plot of the time-frequency decomposition as obtained by the SDA, at a time range of 80 epochs from the beginning of the sleep study. The SO is marked in FIGS. 20*a-b* by an arrow, where a drop in power at all frequencies can be seen. The dominance of the high frequency peak after SO is also evident.

Figure 21A:
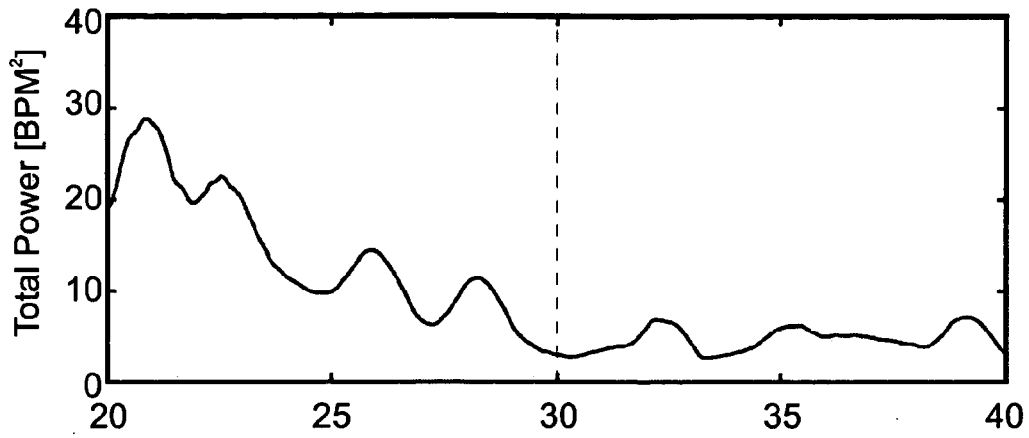
FIG. 21a shows integrated total power as a function of time calculated for the first sleep onset study of Example 3.
Figure 21B:
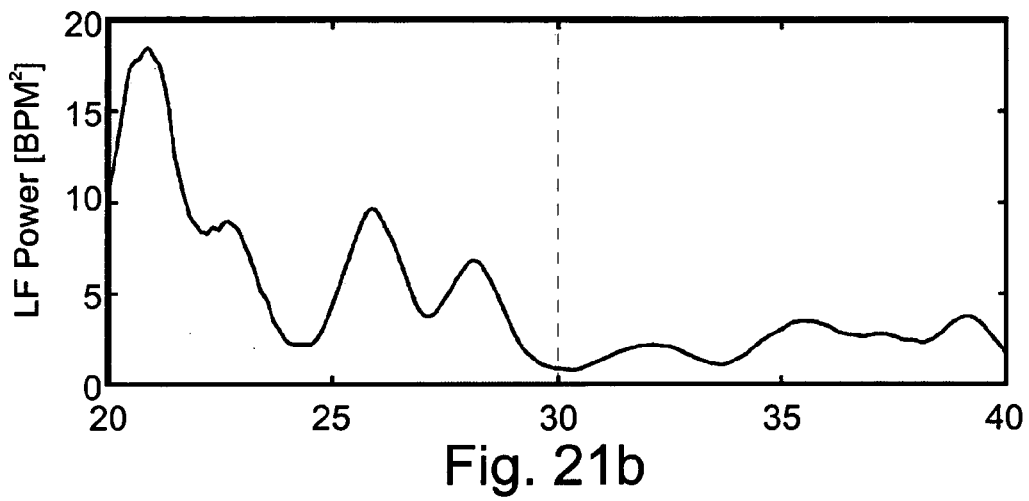
FIG. 21b shows integrated LF power as a function of time calculated for the first sleep onset study of Example 3.
Figure 21C:
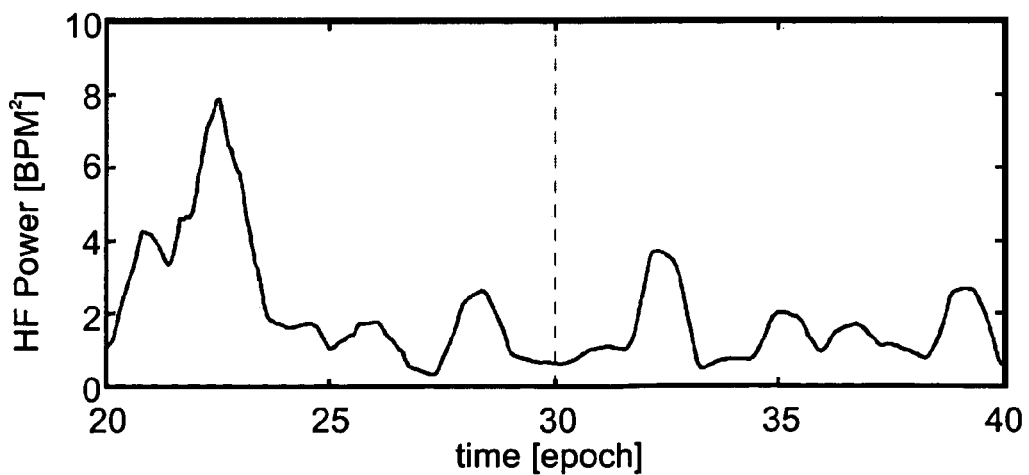
FIG. 21c shows integrated HF power as a function of time calculated for the first sleep onset study of Example 3.

FIGS. 21*a-c* show, respectively, the integrated total power, T, the integrated LF power and the integrated HF power as a function of time. An oscillatory behavior is apparent, synchronous in all bands. The power reached a peak in epochs 21, 23, 26, 28, 32, 35 and 39 in all bands, although not all peaks had the same relative amplitudes. The smoother behavior of the LF power compared to the HF power is due to the SDA algorithm that uses longer time windows for slower frequencies, hence widening the peaks. Also observed were differences in amplitudes before and after SO. Specifically, after SO the amplitudes of the oscillations decreased. All frequency bands exhibited a power drop towards SO, with a local minimum within the epoch of SO.

Figure 21D:
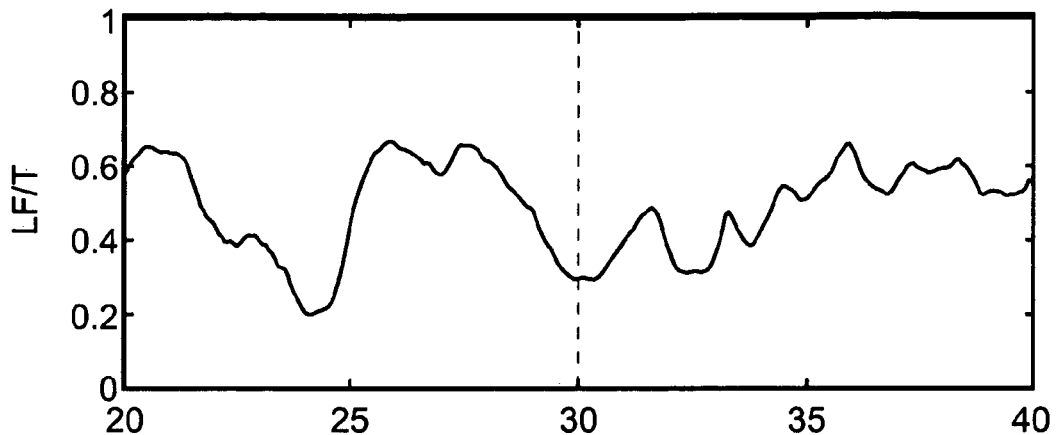
FIG. 21d shows ratio between integrated LF and total power as a function of time calculated for the first sleep onset study of Example 3.
Figure 21E:
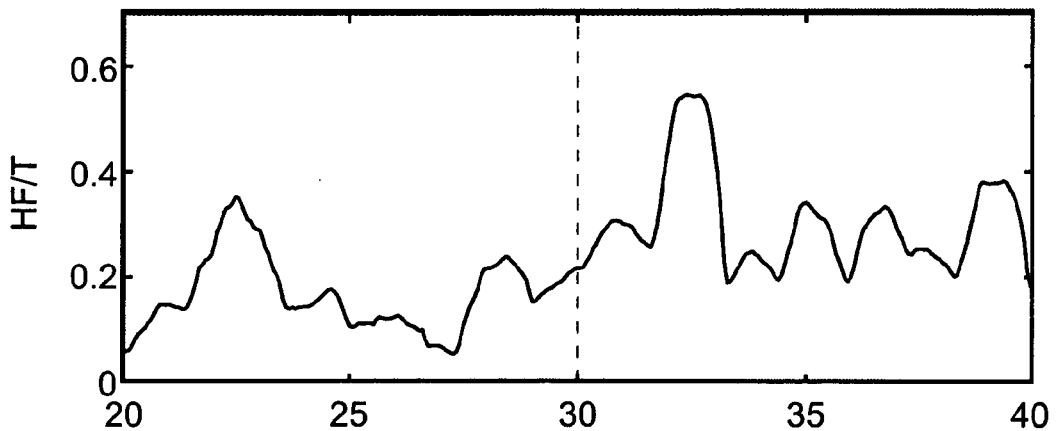
FIG. 21e shows ratio between integrated HF and total power as a function of time calculated for the first sleep onset study of Example 3.
Figure 21F:
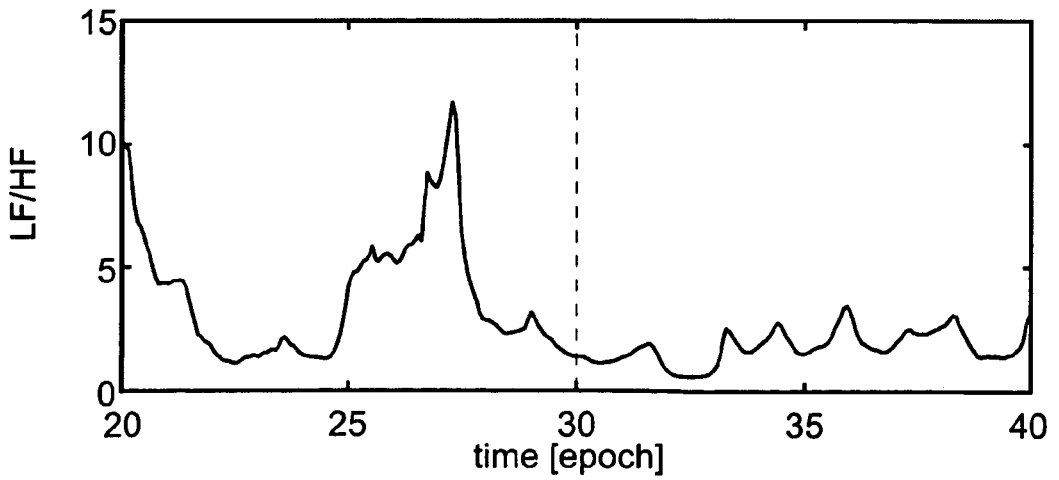
FIG. 21f shows ratio between integrated LF and integrated HF power as a function of time calculated for the first sleep onset study of Example 3.

FIGS. 21*d-f* show, respectively, the LF/T, HF/T, and LF/HF ratios. The HF/T gradually increased, while the LF/HF had a decreasing trend. The trend of the LF/T ratio was harder to define, although a slight increase was observed after SO.

The oscillations shown in FIGS. 21*a-c* were characteristic to all subjects, but the great inter-subject variability both in oscillations magnitude and in the number of oscillations prevented a useful statistical generalization of these cyclic changes. All subjects displayed some oscillations in the integrated powers, typically 2-5 cycles of oscillations before SO. The period of each oscillation was typically from 1 minute to 2 minutes. The gradients during an oscillation (consisting of power surge and dip) were larger than the overall gradient characterizing the drop of the average integrated total power.

Figure 22:
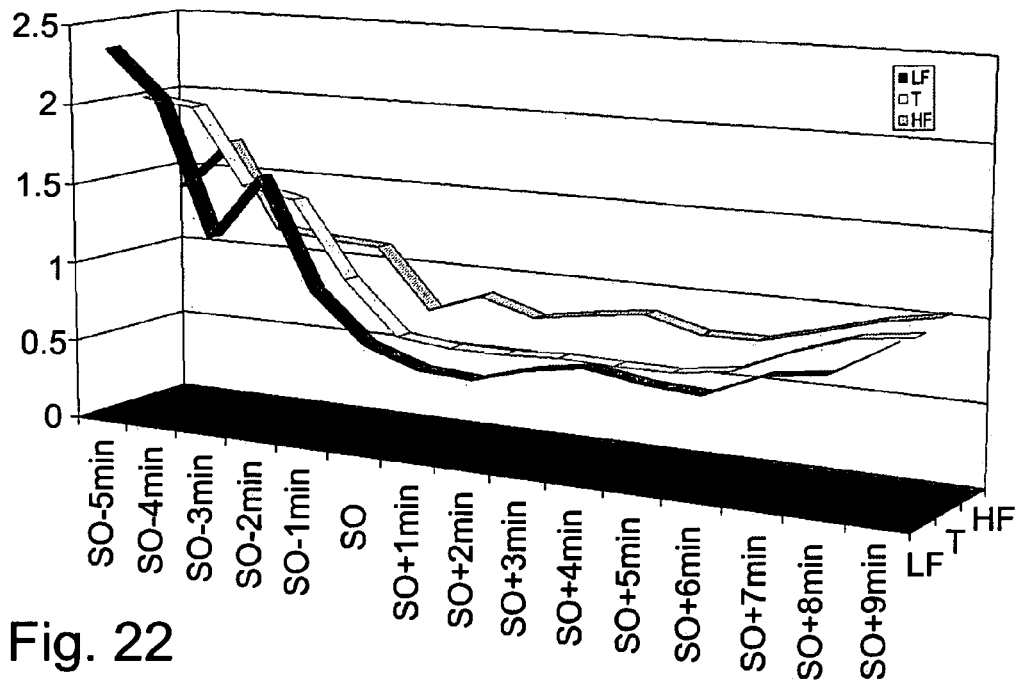
FIG. 22 shows a behavior of the averaged LF, HF and total power over a series of 15 points, starting 5 minutes before sleep-onset (SO) and ending 9 minutes after SO calculated for the first sleep onset study of Example 3.

FIG. 22 shows the behavior of the averaged LF, HF and total power, over a series of 15 points, starting 5 minutes before SO and ending 9 minutes after SO. As can be seen, the above averaging procedure eliminates the individual oscillations seen in FIGS. 21*a-f*. Overall, the power in all frequency bands exhibited a substantial decrease towards SO. The total power and the LF power dropped to one third and one fifth of their value 5 minutes before SO, respectively. HF power fell towards SO by one half All the above changes (before SO) were found significant at least at the 5% level using one way repeated measures ANOVA. Specifically, $F_{(5,35)}=7.24$;

$p<0.0001$, $F(5,35)=2.69$; $p<0.0370$ and $F(5,35)=15.03$; $p<0.0001$ for LF, HF, and T powers, respectively. After SO, there was generally a steady trend, with a mild tendency to increase: ANOVA revealed no significant behavior in this region in any of these bands.

Figure 23:
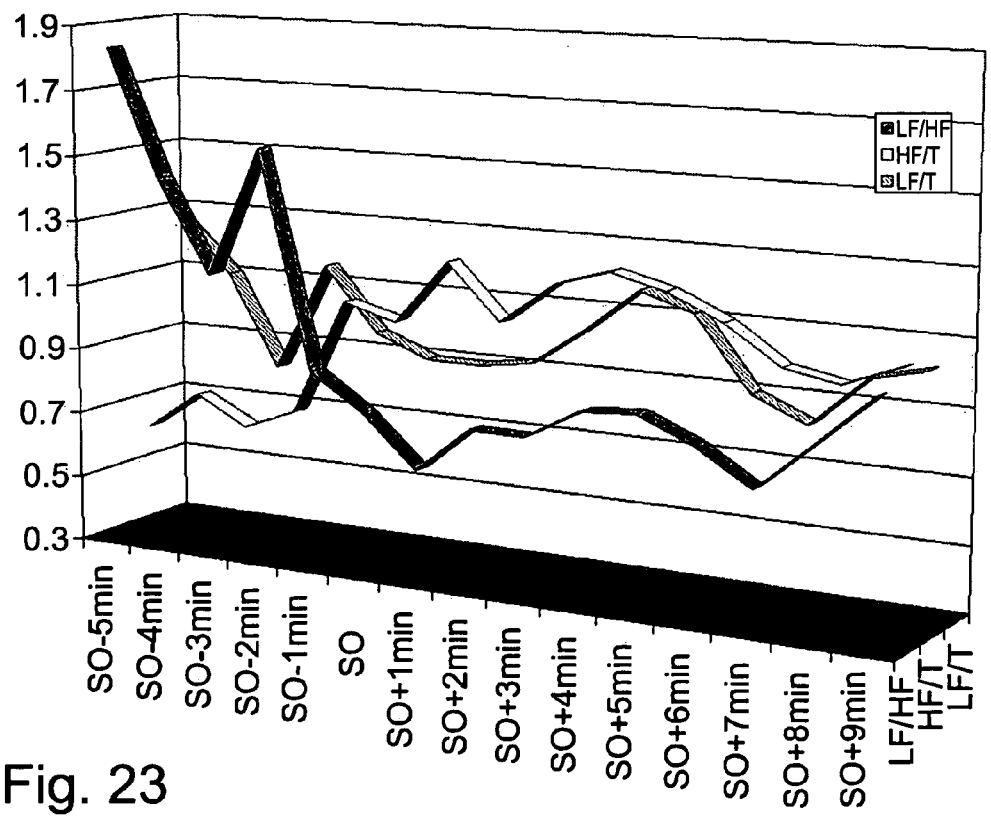
FIG. 23 shows a behavior of the ratios LF/T, HF/T and LF/HF, over the 15 points series calculated for the first sleep onset study of Example 3.

FIG. 23 shows the behavior of the ratios LF/T, HF/T and LF/HF, over the above-mentioned 15 points series. The LF/T ratio had an oscillatory behavior over the entire period, with local minima at 3 minutes before SO and 7 minutes after SO. The HF/T ratio raised towards SO, then reached a plateau: ANOVA detected a significant change before SO ($F(5,35)=4.77$; $p<0.002$) and no significant change after SO. The sympathovagal balance, LF/HF, reached a global minimum one minute after SO, with a significant change prior to SO ($F(5,35)=4.32$, $p<0.004$), and a non-significant posterior behavior.

As stated, in order to verify the descending nature of the LF, HF, and T powers and of the LF/HF ratio, a one-tailed paired t-test was performed between the value of these observables at SO and at each of the other time steps. SO values were found significantly lower ($p<0.05$) than the values prior to SO, starting 5 minutes before SO and ending 2 minutes before SO. Similar tests showed that HF/T values at SO were significantly higher than those values 5 minutes prior to SO up to 2 minutes prior to SO.

Discussion of the Results

The results indicated that during the process of falling asleep, the autonomic activity as represented by the HRV measures LF, HF, and T, the normalized parasympathetic power, HF/T, and the sympathovagal balance, LF/HF, changed markedly. While autonomic activity in both its sympathetic and parasympathetic branches is reduced, the relative parasympathetic contribution increases. Thus, the transition from quiet wakefulness to NREM sleep can be viewed as a shift between two different modes of ANS operation.

The result of decreased LF/HF ratio after SO is in agreement with other studies in which the ANS was investigated on a 24-hour scale [Furlan, R. et al., "Continuous 24-hour assessment of the neural regulation of systemic arterial pressure and RR variabilities in ambulant subjects", Circulation 81, 537-547, 1990; Van De Borne, P. et al., "Effects of wake and sleep states on the 24-h autonomic control of blood pressure and heart rate in recumbent men", *Am. J. Physiol.* 266, H548-H554, 1994]. The lack of significant behavior of the normalized LF power (LF/T), found in the present study, during SO, does not seem to be in accordance with these studies, which showed a decrease of this ratio during the night. However, this difference is due to the fact that the present work investigates the ANS activity continuously, during a short period of time around SO.

The decrease in parasympathetic activity (absolute HF power) found at SO should be viewed more carefully. First, this decrease during SO does not contradict the above studies that have shown a gradual increase in absolute/normalized HF power as NREM sleep deepens (not at SO). Second, as is well known, respiratory rate and volume influence the variability of the HR. The respiratory rate does not represent a problem since in this study, no significant intra-subject change in respiratory rate during SO, was found. However, respiratory tidal volume has been observed to decrease during SO and might account for a certain decrease in absolute HF power [Hirch, J. A. and Bishop B., "Respiratory sinus arrhythmia in humans: how breathing pattern modulates heart rate", *Am. J. Physiol.* 241, H620-H29, 1981]. Nevertheless, the synchronicity, not affected by breathing, which was observed in the present study between the behavior of the LF power and HF power (see the matching surges in FIGS. 21*a*-*f*), suggests that the majority of the decrease in HF power is due to a withdrawal in autonomic activity.

The relative short time interval, around SO, that was under investigation, and the relative fast decline of parasympathetic activity does suggest that the parasympathetic activity at SO is predominantly affected by the sleep system rather than the circadian system.

While the above changes characterize the average behavior of the ANS during SO, it should be emphasized that they represent only the overall trend of the individual behavior. In the individual, the whole process of falling asleep can be viewed as an interplay between quiet wakefulness and NREM sleep. The HRV measures oscillate as the subject approaches SO, and their values gradually descend toward a minimum at SO. Each fall reflects a state closer to unequivocal sleep while each of the subsequent surges represents some recovery of wakefulness. Oscillations of these measures occur also after SO, however with lower amplitudes, indicating a stabilization of the ANS.

Example 4

SO Detection

In this study the behavior of the autonomic nervous system was investigated and compared to the behavior of EEG at sleep onset.

Experimental Methods

The study was performed on sixteen healthy subjects (ages 18-48 years) who had a long sleep latency. For the purpose of validating the method and to compare the results with other commonly employed methods, standard PSG data were also collected.

The subjects underwent a full sleep study including recordings of the following signals: (i) 2 central EEG (at 100 Hz); (ii) 2 occipital EEG (digitized at 100 Hz) (iii) EOG (digitized at 100 Hz); (iv) chin EMG (digitized at 100 Hz); (v) ECG (digitized at 200 Hz); (vi) abdominal and chest respiratory effort (digitized at 12.5 Hz); (vii) nasal and oral airflow (digitized at 12.5 Hz); and (viii) oxygen saturation and pulse wave (digitized at 12.5 Hz).

The PSG data were monitored off-line and sleep stages were determined according to standard R&K criteria by a sleep expert, to provide a reference against which the automated SO detection method was examined. In the standard R&K criteria, SO was defined as the first of two consecutive NREM Stage-1 epochs or the first epoch of any other sleep stage. Each epoch corresponds to 30 seconds.

The procedure included the following steps in which in a first step an SDA was applied on the instantaneous RR interval for each subject. The resultant time-frequency decomposition was integrated over 3 spectral bands: VLF (0.005-0.04 Hz) LF (0.04-0.15 Hz) HF (0.15-0.5 Hz). This step further included a normalization procedure performed on each of the spectral bands.

In a second step, an SDA was applied on the signal recorded from the central EEG channel. The resultant time-frequency decomposition of this step was integrated over 2 spectral bands: Delta (0.5-4 Hz) and Alpha (8-15 Hz).

In a third step two reference points were selected for each subject: (i) an Alpha reference point defined as the time of power decrease to two thirds of average value before SO according to standard criteria; and (ii) a Delta reference point defined as the time of power increase to two thirds of average value after SO according to standard criteria.

In a fourth step, the normalized results of each spectral band were averaged over all subjects. A total number of 21 points (50 seconds apart) was used for the averaging: 10 points before Alpha/Delta reference time, beginning 500 seconds before the respective reference time, 1 point at the reference point, and 10 points immediately following the respective reference time.

Experimental Results

FIGS. 24*a-f* shows the results of for a subject who entered sleep smoothly.

FIGS. 24*a-c* show, respectively, the integrated VLF, LF and HF power spectrum as a function of time measured in units of 30 second epochs; FIGS. 24*d-e* show, respectively, the EEG power spectrum in the Delta and Alpha frequency bands; and FIG. 24*f* shows the corresponding sleep stages based on standard sleep scoring criteria. As shown, the power drop in the Alpha band and power surge in the Delta band, and the power drop in VLF, LF, and HF bands occur simultaneously around epoch 25. Note that these power changes do not necessarily coincide with classical definition of SO, which, for this subject, had occurred at epoch 19. VLF and LF drops repeated in most subjects.

FIG. 25*a-f* shows the same parameters as FIGS. 24*a-f* for a subject who had difficulties to fall asleep, and reached unequivocal sleep, according to standard criteria, in epoch 123. Note the Alpha power decrease and Delta power increase begin with a delay of about 5 epochs (around epoch 130) and are very moderate in comparison with FIGS. 24*b-d*.

Figure 26A:
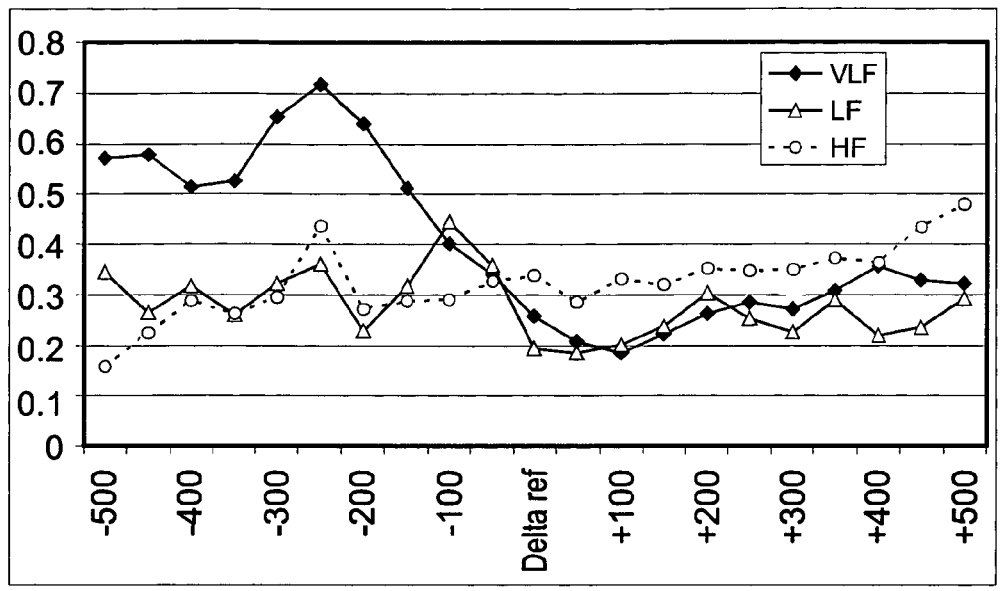
FIG. 26a shows normalized power spectrum of the RRI series, averaged over all the subjects who participated in the second sleep onset study of Example 4, with reference set on the time that the Delta power reached two thirds of its average value after SO.
Figure 26B:
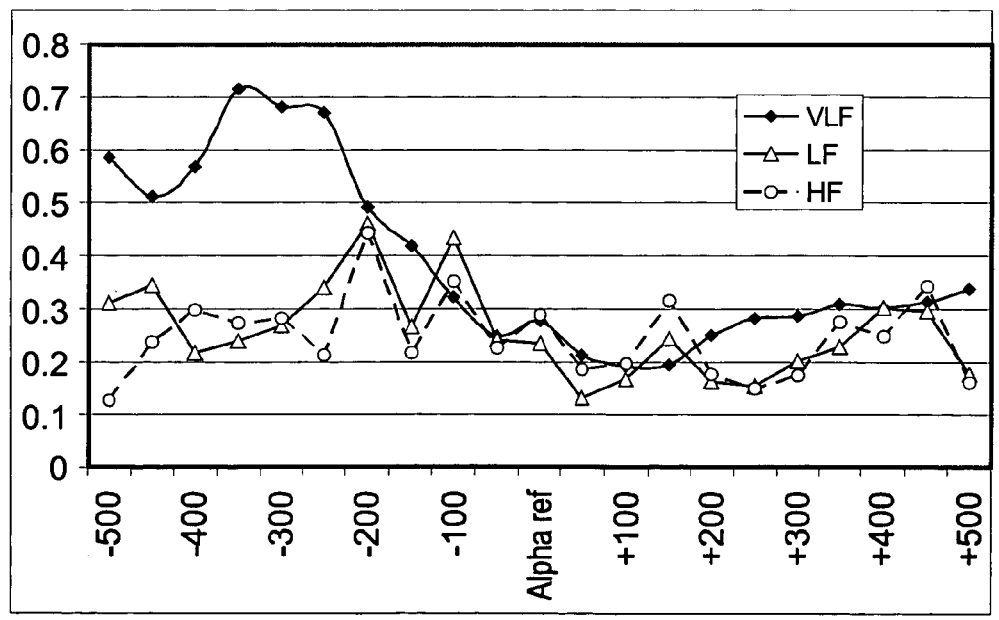
FIG. 26b shows normalized power spectrum of the RRI series, averaged over all the subjects who participated in the second sleep onset study of Example 4, with reference set on the time that the Alpha power reached two thirds of its average value before SO.

FIGS. 26*a-b* show normalized power spectrum of the RRI series, averaged over all subjects (n=16), and synchronized to a common reference point. The abscissa is the time scale in seconds relative to reference point. FIG. 26*a* shows results with reference set on the time that the Delta power reached two thirds of its average value after SO, and FIG. 26*b* shows results with reference set on the time that the Alpha power decreased to two thirds of its average value before SO. As shown, the VLF power decreased gradually towards the reference point, reached minimal values around 100 seconds after the reference and increased moderately thereafter. The LF power displayed similar, yet less pronounced behavior. No significant changes were found in the HF power.

Discussion of the Results

The present study revealed the autonomic changes during SO and their interconnection with an important measure of electro-cortical activity of the brain, the surface EEG.

The results show that the power in the LF frequency band of RRI series, and especially the VLF power decrease towards a minimal value during the process of SO. The averaged minimal values in VLF and LF power occurred within 100 second from a reference point indicating one third decrease from average Alpha/Delta power before/after SO. HF power, that reflects mainly parasympathetic activity and is modulated by respiration, did not change significantly during SO. This finding should be interpreted in the context of the meticulous studies performed by Trinder et al. [Trinder J, et al., "Respiratory instability during sleep onset", *J. Appl. Physiol.*, 1992, 73:2462-9; Worsnop et al., "Activity of respiratory pump and upper airway muscles during sleep onset", *J. Appl. Physiol.*, 1998, 85:908-20], which reported no changes in respiratory rate and a decrease in minute ventilation, which was related with the fluctuations in wakefulness. This suggests that a possible increase in HF power was obscured by the decrease in ventilation, known to reduce HF power. Furthermore, a potential increase in HF during SO, at LS, corroborate with the known HF power increase during deeper stages of NREM sleep (SWS).

An additional finding of the present study is related to the oscillatory waning pattern of wakefulness before SO. This same pattern appears in the decrease of Alpha power as well as in the increase in Delta power of surface EEG. This undulant behavior is accompanied by a similar behavior of the ANS function as derived from HRV. The power in all frequency bands of the RRI series displays fluctuates synchronous with those in Alpha and Delta EEG power bands (see for example epochs 107-108 in FIG. 25*a-f*).

Beside the decrease in VLF power which starts before the changes in EEG power, a wavelike behavior of VLF power that occurred before SO, was also observed, even when the subject developed sleep smoothly (see FIGS. 24*a-f*).

Hence, it was demonstrated that ANS activity at the wake-sleep transition is affected by the same underlying mechanism that governs the process of SO. The ANS activity fluctuates towards the period of SO and reaches a minimal value during that period. Monitoring ANS activity can thus provide an additional indicator of the transition from wakefulness to sleep. This indicator is obtained easily and provides insight into the changes in control mechanisms that occur during sleep.

Example 5

Awakenings and Arousals Detection

Experimental Methods

A study to determine awakenings and arousals was performed on six healthy subjects (4 males and 2 females) without any known sleep problem.

For the purpose of validating the method and to compare the results with other methods, standard PSG data were also collected for two consecutive nights.

Hence, the subjects underwent two consecutive full night sleep studies including recordings of the following signals: two central and two occipital EEG leads (digitized at 100 Hz), two eye movement leads (digitized at 100 Hz), submental EMG (digitized at 100 Hz), leg movement (digitized at 10 Hz), nasal airflow (digitized at 100 Hz), end-tidal $CO_2$ (digitized at 12.5 Hz), oxygen saturation and pulse waveform (digitized at 1 Hz), and chest and abdominal effort (digitized at 10 Hz).

The PSG data were monitored off-line and sleep stages were determined according to standard R&K criteria by a sleep expert. All epochs containing movements and arousals were marked.

The ECG data were computer-scanned for peak detection, in order to obtain the RRI series. The ECG and RRI series were then scanned to correct artifacts (including abnormal beats) and interpolated in case of premature or missing beats.

The procedures for the detection of awakenings and arousals were in accordance with the respective steps of method 40, as further detailed hereinabove.

Experimental Results

Figure 27:
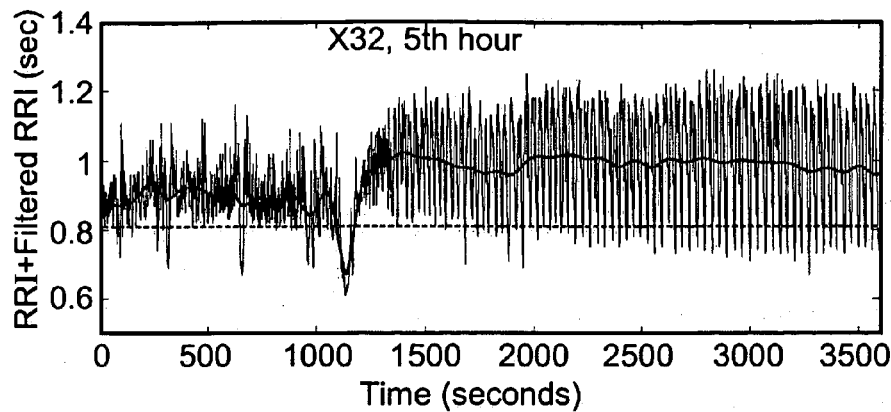
FIG. 27 shows RRI series during the 5th sleep hour of a healthy subject.

FIG. 27 shows the RRI series during the 5th sleep hour of subject x32. A decrease in RRI was seen at a time between seconds 1000-1200. This segment was marked as wake. The solid curved line represents the application of the low-pass-filter, which diminished the periodic pattern after the wake segment and smoothed the first decrease.

Figure 28:
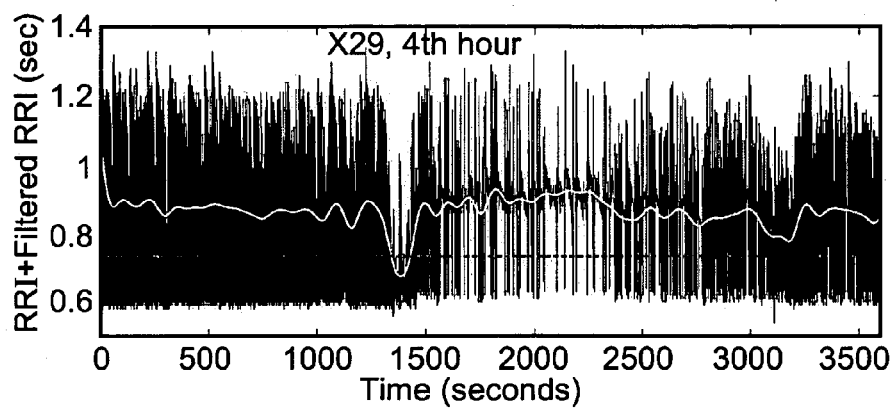
FIG. 28 shows RRI series during the 4th sleep hour of a subject having arrhythmia.

FIG. 28 shows the RRI series during the 4th sleep hour of subject x29. This subject had arrhythmia. FIG. 28 demonstrates the successful application of the designed low-pass-filter even on a very variable RRI series characterizes a patient with frequent premature beats.

From a total of 110 awakening episodes (a sequence of one epoch or more that contain awakening alternating with non-REM sleep), as defined by standard methods, 80% were automatically detected by the present method (range: 76%-92%), 12% of the remaining 20% did not affect the RRI, thus could not be detected.

Example 6

REM Detection Using EMG Parameters

A REM sleep study was performed on the 34 subjects of Example 1, where 17 subjects served as a training set and the other half served as a test set. The procedure described below was first applied on the training set for determining the parameters. Then the procedure was applied on the test set, using the previously determined parameters.

For the purpose of validating the method and to compare the results with other methods standard PSG data were also collected.

Hence, the subjects underwent a full sleep study including recordings of the following signals: 2 central EEG (digitized at 100 Hz), 2 occipital EEG (digitized at 100 Hz), chin and tibialis EMG (digitized at 300 Hz), left and right EOG (digitized at 100 Hz), 2 ECG (digitized at 500 Hz), abdomen and thorax effort (digitized at 10 Hz), oxygen saturation (digitized at 1 Hz) and nasal air flow (digitized at 100 Hz).

As in Example 1, the PSG data were monitored off-line and sleep stages were determined according to standard R&K criteria by a sleep expert, to provide a reference against which the automated REM detection method was examined.

The automated REM detection procedure included the steps described in method 20, where seven EMG parameters were extracted from the ECG signal and used for identifying the REM sleep. The EMG parameters were: mrEMG, nPWR, ZC, MF, MPF, EZC and PVAR, as further detailed hereinabove.

A single ECG lead was used. The lead was connected adjacent to the heart such that two electrode were positioned on the same muscle. This unconventional lead allowed for recording both the ECG and EMG signals simultaneously.

The P and T waves of the ECG signal were eliminated by a high pass 10 Hz filter and the QRS complex was eliminated from the ECG signal by a combination of gating and/or subtraction techniques. The residual signal was then processed to calculate the EMG parameters.

Example 7

Apnea Detection Using ABI

In this study the correlation between the ABIs as defined above and obstructive sleep apnea syndrome (OSAS) was investigated.

Experimental Methods

The study was performed on 24 subjects having at least one sleep disorder or sleep disturbance, including snoring, poor sleep quality, excessive daytime sleepiness or some degree of fatigue.

For the purpose of validating the method and to compare the results with other commonly employed methods, standard PSG data were also collected.

Hence, the subjects underwent a full sleep study including recordings of the following signals: 2 central EEG (digitized at 100 Hz), 2 occipital EEG (digitized at 100 Hz), leg and chin EMG (digitized at 100 Hz), ECG (standard lead II), two eye movement leads (digitized at 100 Hz), and abdominal and chest respiratory effort, nasal and oral airflow, oxygen saturation and pulse wave, all of which digitized at 12.5 Hz. In addition, the subjects were monitor to record body position and connected to an audio channel to record snoring.

The PSG data were monitored off-line and sleep stages were determined according to standard R&K criteria by a sleep expert. All epochs containing arousals, respiratory events (obstructive apneas and hypopneas) and leg movements were carefully registered along with sleep architecture for each subject. The respiratory disturbance index (RDI) commonly defined as the density of apneas and hypopneas per hour of sleep served as cutoff point to discriminate between a control group and an OSAS group, each having 12 subjects. The control group included subjects with no diagnosed sleep disorder and $RDI \leq 5$, and the OSAS group included subjects with RDI>5 and no other sleep disorder.

The procedure consisted the steps described in methods 10, 20 and 40 above, where the time-frequency decomposition was obtained using a wavelet transform and three power components (VLF, LF and HF) were calculated by integrating the transform over the following ranges: 0.005-0.04 Hz (VLF power), 0.04-0.15 Hz (LF power) and 0.15-0.45 Hz (HF power). The RRI series was obtained by a computer-scan for peak detection followed by manual correction of erroneous detections.

One respiratory channel, having minimal number of acquisition artifacts, was selected, and analyzed using the same wavelet transform so as to compare the respiratory spectrum to the above HF range.

Once the time-frequency decomposition was calculated and integrated, the following additional parameters were calculated, sympathovagal balance (defined and referred to hereinafter as LF/HF), total power, normalized LF (defined as LF/(mean HR) and referred to hereinafter as NLF), normalized HF (defined as HF/(mean HR) and referred to hereinafter as NHF) and the percentage of VLF of the total power (hereinafter % VLF).

Three ABIs were defined (see also the description of method 100 above), $ABI_{LS}$, $ABI_{SWS}$ and $ABI_{REM}$. Each ABI was calculated according to the rule: $ABI_S = (\% S)(LF/HF)_S$, where S=LS, SWS or REM. A total ABI was also calculated as the sum of the three ABIs.

Statistical analysis was performed as to compare HRV time-dependent parameters within each group as they change with the sleep-wake state and correlate with respiratory disturbance (multiple measures ANOVA). A two-tailed unpaired t-test was used to compare between the control group and the OSAS group.

Experimental Results

Normal subjects were younger (27.5±15.2y) than OSAS patients (42.3±11.2y) and significantly slimmer with body mass index (BMI) of 24.8±4.6 for the control group and 29.5±3.2 for the OSAS group. Male sex predominated in the OSAS group (9 m/3 f for the control group and 7 m/5 f for the OSAS group).

The two groups also differed, in terms of sleep architecture and quality. The results for total sleep time (TST), percentage of SWS, REM sleep, wake time after sleep onset (WTAS), and other specific sleep feature are presented in table 4.

TABLE 4

| Sleep feature | Normal mean(stdev) | OSAS mean(stdev) |
|---|---|---|
| TST (minutes) | 390.3(70.8) | 389.4(52.4) |
| % SWS | 28.3(7.3) | 25.8(7.9) |
| % LS | 42.7(6.5) | 47.6(12.9) |
| % REM | 19.5(5.9) | 16.7(4.8) |

TABLE 4-continued

| Sleep feature | Normal mean(stdev) | OSAS mean(stdev) |
|---|---|---|
| % WTAS | 8.3(10.3) | 12.0(7.8) |
| Arousals | 78.4(37.9) | 168.6(95.4) |
| Stage shift index | 12.7(2.4) | 17.7(4.4) |
| Sleep efficiency | 89.4(11.7) | 85.3(8.5) |
| RDI | 1.6(1.5) | 35.6(21.4) |
| Mean Sat $O_2$ | 96.9(1.5) | 94.4(2.5) |

Figure 29:
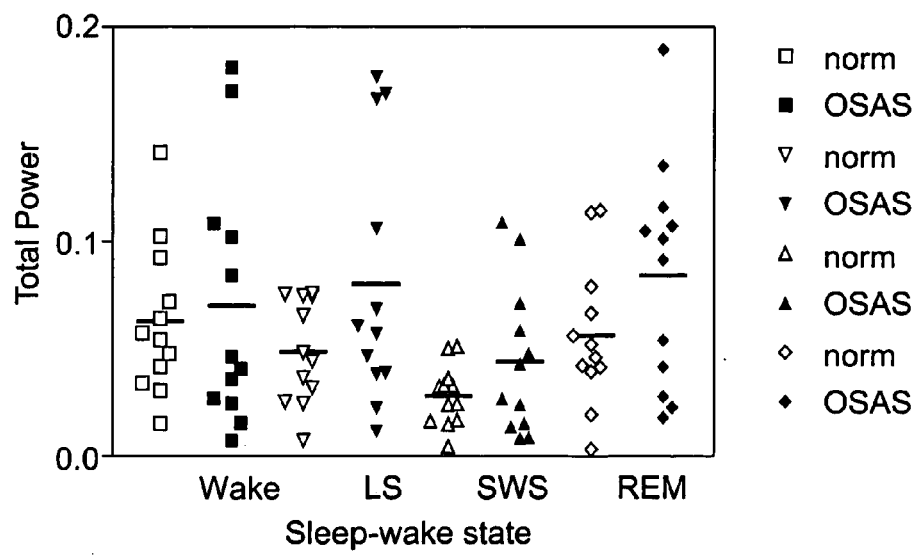
FIG. 29 shows the total power during various sleep stages in obstructive sleep apnea syndrome (OSAS) patients and normal subjects.

FIG. 29 shows total power of HRV for the wake, LS, SWS and REM sleep. As shown, the power was higher in OSAS patients at all stages. The total power of HRV decreased during sleep as compared to wakefulness, with a gradual decrease upon the deepening of NREM sleep, and minimal values during SWS in both OSAS patients and normal subjects.

Figure 30A:
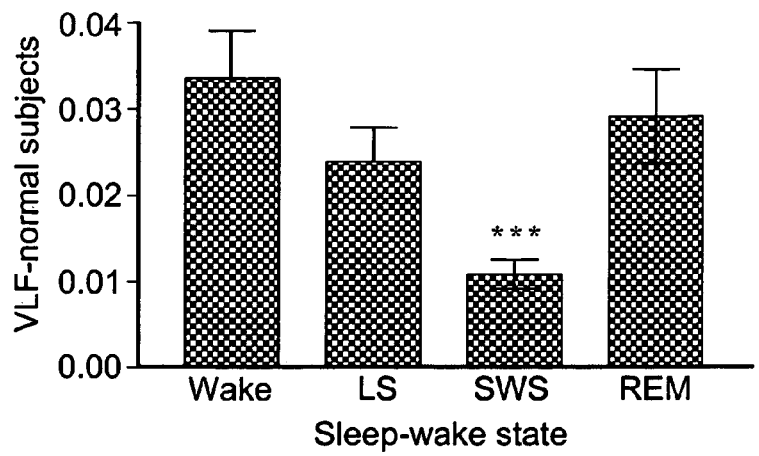
FIGS. 30a-c are charts of VLF power (a), LF power (b) and HF power (c), in normal subjects.
Figure 30B:
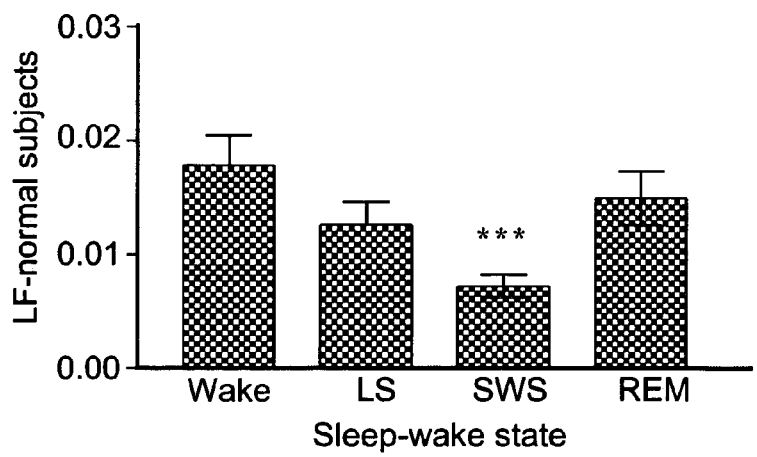
Figure 30C:
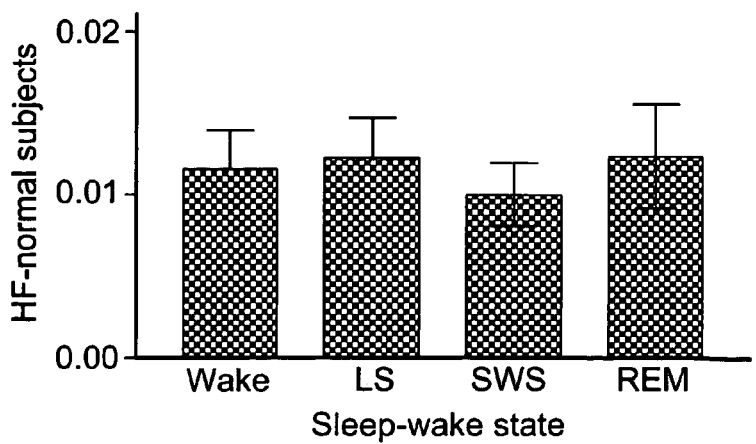

FIGS. 30a-c show, respectively, VLF power, LF power and HF power for the normal group. The normal group displayed significant decrease in total power, VLF, LF, % VLF and LF/HF with the deepening of NREM sleep with minimal values during SWS (multiple measures ANOVA). A similar trend was observed also in OSAS group. The difference between VLF, LF during Wakefulness, LS and SWS was highly significant (p<0.001, two-tailed t-test). The decrease in % VLF, was also very significant and reached minimal values during SWS (p<0.001). It should be noted that when a patient reaches SWS there are less respiratory events than during LS.

The LF/HF ratio decreased in OSAS patients towards lowest values during SWS, however this behavior was inconsistent and did not reach statistical significance.

Table 5 below, summarizes the differences between the groups during SWS:

TABLE 5

| Variable | Normals Mean(stdev) | OSAS Mean(stdev) |
|---|---|---|
| VLF ns | 0.0108 (0.006) | 0.0166 (0.011) |
| LF ** | 0.0072 (0.003) | 0.0136 (0.012) |
| HF ns | 0.0099 (0.007) | 0.0139 (0.015) |
| Tot ns | 0.028 (0.014) | 0.044 (0.035) |
| % VLF ns | 0.028 (0.093) | 0.044 (0.093) |
| LF/HF ** | 0.84 (0.27) | 1.53 (0.87) |

During SWS, the OSAS group showed significantly higher LF and LF/HF values of p<0.001 (denoted by ** in Table 5), whereas the other variables (denoted ns in Table 5) showed no significant results in discriminating between the groups.

Figure 31:
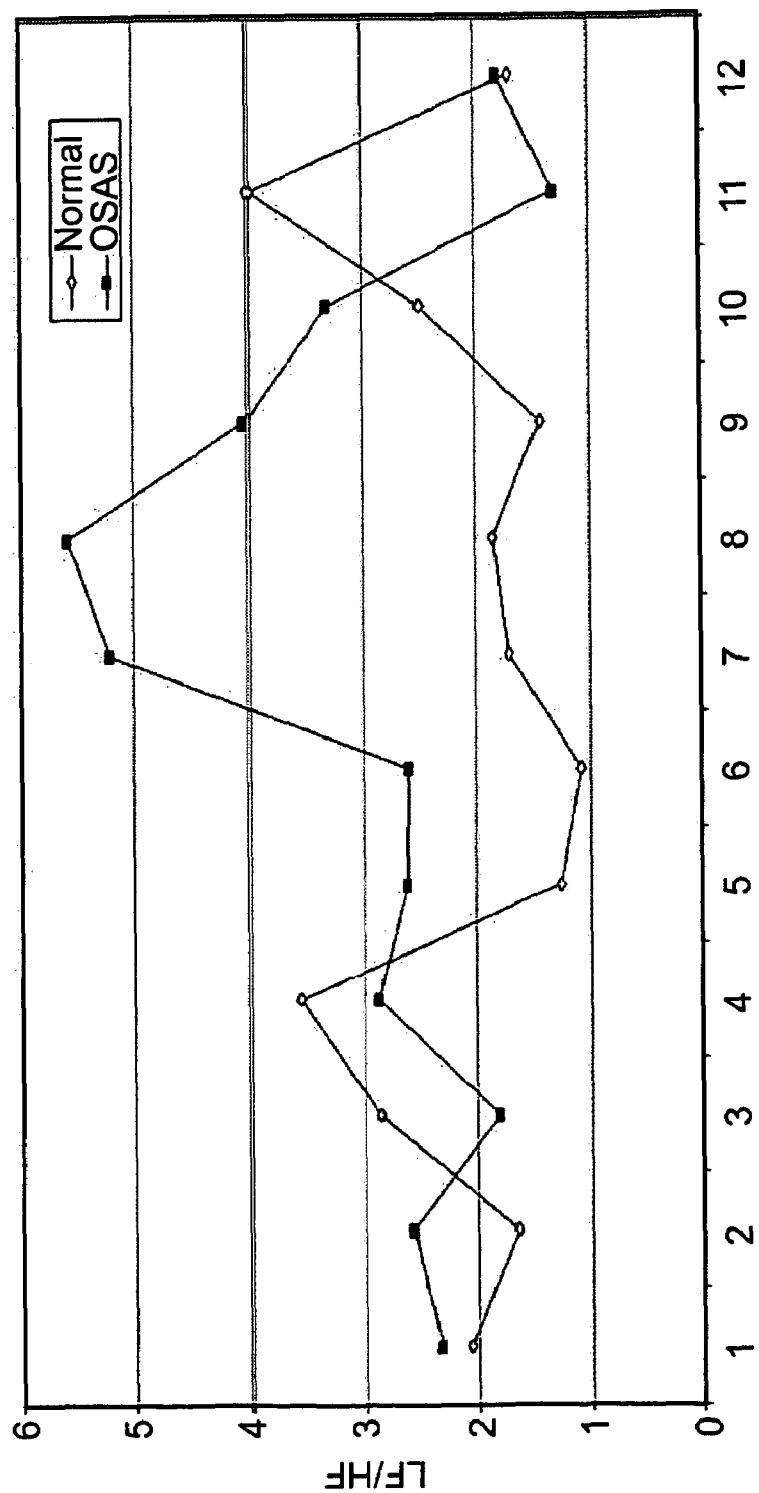
FIG. 31 shows LF/HF power parameter during wakefulness for normal subjects and OSAS patients.

FIG. 31 shows the LF/HF power parameter, used in the definition of the ABI, during wakefulness in both study groups. The horizontal axis represents individual subjects (12 subjects in each group). As shown in FIG. 31, the LF/HF power parameter was higher in most OSAS patients.

Figure 32:
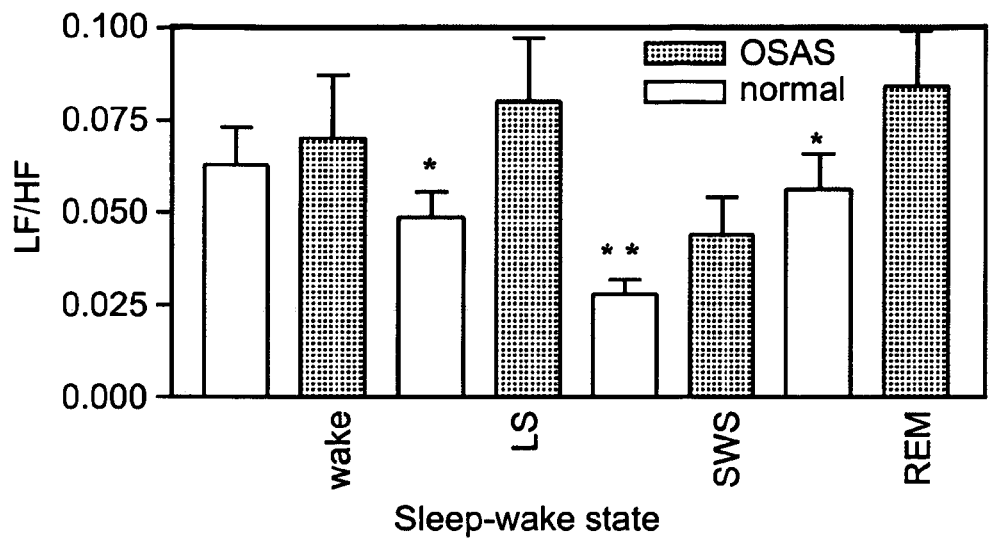
FIG. 32 shows LF/HF power parameter during wakefulness, LS, SWS and REM sleep as calculated globally for normal subjects and OSAS patients.

FIG. 32 shows the LF/HF power parameter during wakefulness, LS, SWS and REM sleep as calculated globally for both study groups. In FIG. 32, the symbol * denotes a p<0.05 level of significance, and the symbol ** denotes a p<0.001 level of significance. As shown, the LF/HF ratio was significantly higher at all sleep stages in OSAS patients.

Figure 33:
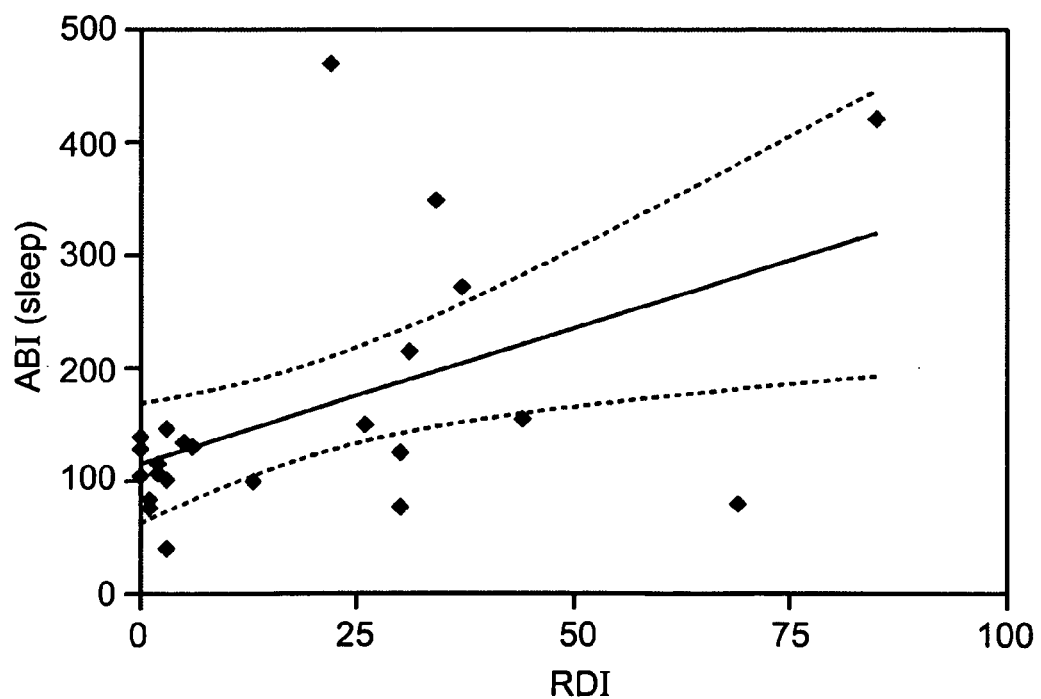
FIG. 33 shows correlation between the total autonomic balance index (ABI) and respiratory disturbance index (RDI)

FIG. 33 shows correlation between the total ABI and the RDI. The dashed line in FIG. 33 represents 95% confidence interval (Pearson correlation $r^2$=0.2559) for all 24 subjects in the study. As shown there is a strong correlation between the total ABI and the RDI. All the ABIs, including the total ABI, were significantly higher in OSAS group. On the other hand, no correlation was found between the number of arousals, the density of arousals per hour of sleep and the RDI or the ABI.

Discussion of the Results

The results of the present study for the normal group show a decrease in the total power of HRV along with a significant decrease of power in the LF range, without an accompanying significant decrease in the HF spectral component with the deepening of NREM sleep. These findings suggest that the autonomic activity and sympathetic activity decrease in NREM sleep with an obvious parasympathetic predominance during SWS. A surge in sympathetic activity during REM sleep brings the level of activity of the ANS to levels similar to those during wakefulness.

The same trend was observed in OSA patients, however the levels of sympathetic activity were significantly higher in this group during wakefulness, as well as during the various sleep stages, including SWS. The LF/HF power parameter in these subjects was significantly higher during all sleep stages. Thus, patients are more sympathetically driven during sleep, and most of them have also increased sympathetic activity during wakefulness.

The ABI shows a good correlation with the RDI indicating that the worse the breathing obstruction the higher the ABI. This autonomic up-regulation does not result from the sleep disruption observed in the OSAS group and measured by the density of detected EEG arousals.

Example 8

Detection of Body Positions

The objective of this study was to determine body positions and changes in the body position using ECG signals.

Experimental Methods

The study was performed on twelve healthy (no heart disease) volunteers (5 females and 7 males), aged 25 to 50 years. Data acquisition consisted of simultaneous recordings of standard ECG leads I, II, & III. Data were sampled at a rate of 1000 Hz and stored on a computer for later analysis. During acquisition, the subjects were asked to rotate between four body positions: Back (hereinafter B), Left (hereinafter L), Prone (hereinafter P) and Right (hereinafter R) every 250 seconds. Each position was repeated 3 times (not in the same order) for a total duration of 3000 seconds, according to the following 12-posture sequence: B-L-P-R-B-R-P-L-B-L-P-R.

The time allowed for each position change was 30 seconds, which were part of the total 250 second epoch spent in each posture. Subjects were instructed to assume a comfortable, relaxed posture in each of the body positions, to lie still and to avoid muscle strain. No further instructions regarding the exact body layout were given, on behalf of generality and in order to avoid uncomfortable postures.

The analysis of the data was in accordance with the steps of method 120 above. Specifically, R-wave peaks (see FIG. 7) were detected using an automated algorithm, based upon finding maxima of absolute values of second order derivatives. The algorithm was followed by a manual scan to correct erroneous and missing detections (less than 1%).

The inflection points, used to determine the RWD function (see FIG. 7) were found by upsampling the recorded signal by a factor of 100, taking its first derivative and searching for local maxima and minima of the first derivative in the vicinity of each R-wave peak (since most of power of the QRS signal is contained at frequencies up to 150 Hz, a sample rate of 1000 Hz should be enough to permit full reconstruction and resampling the signal).

In addition, for each R-Wave two segments, L-RWD, R-RWD were also defined, as further detailed hereinabove.

A non-linear median filter of 131 heart beats width (approximately 2 minutes) was applied for smoothing the RWD values without affecting the step changes that, as stated represent a body position change. The filter was selected to be long enough to diminish relatively fast changes in RWD (caused by, e.g., small body position adjustment, small perturbations in electrodes positions due to sweat or breathing, or failure of the automatic algorithm to measure the RWD correctly), yet short enough so as to include all body positions.

Changes of body positions are related to a ratio between the standard deviation (SD) of the RWD in a given body position and the step change, Δ, in the RWD function when changing body position. Practically, a moving window was used to calculate the mean and SD of 65 points to the left and to the right of each RWD value. A body position change was defined when the absolute difference, between the two adjacent mean RWD values (left and right), was greater than twice the sum of the two adjacent SDs (left and right).

A repeatability coefficient was calculated according to the definition recommended by Bland & Altman [Bland J. M., and Altman D. G., "Statistical methods for assessing agreement between two methods of clinical measurement", (1986), The Lancet, 307-310]. The repeatability coefficient enables a comparison of the reproducibility of the results in each lead upon reassuming a body position.

For each subject, L-RWD and R-RWD values were used to construct a 2 dimensional phase space, when one lead was used, and a 4 dimensional phase space when two leads were used. For each individual case, the k-means iterative algorithm [Duda R. O. et al., "Pattern Classification", chap. 10, John Wiley & Sons, Inc., New York, USA)] was used with minimum distance classifier and minimum Mahalanobis distance classifier. The only a-priori knowledge was the expectation of 4 groups of body positions. The end condition was a change of less than 1% in classification results, between successive iterations. The classification results as a function of time were smoothed by removing any short speckles from a homogeneous environment. Thus, the output of this procedure was a rather smooth classification of each QRS complex into one of four positions. An example of the results of the position classification for a single subject is presented in FIGS. 35 and 36a-c of the Experimental Results subsection (see below).

Evaluation of the classification was performed by comparing the known positions (according to the instructions to the subjects) to the output of the method. The known position related to each QRS complex was used to build a reference classification vector. Then, the centers (in phase space) of each group, according to the reference classification, and according to the algorithm results, were established. Each group obtained by the method, was paired with one group of the reference results according to a minimal distance criterion between their centers. For each of the paired groups, the number of overlapping elements was counted. The score was the ratio of total number of correct classifications to the total number of QRS complexes. QRS belonging to transition periods (during changes of body position) were not scored.

Experimental Results

Figure 34:
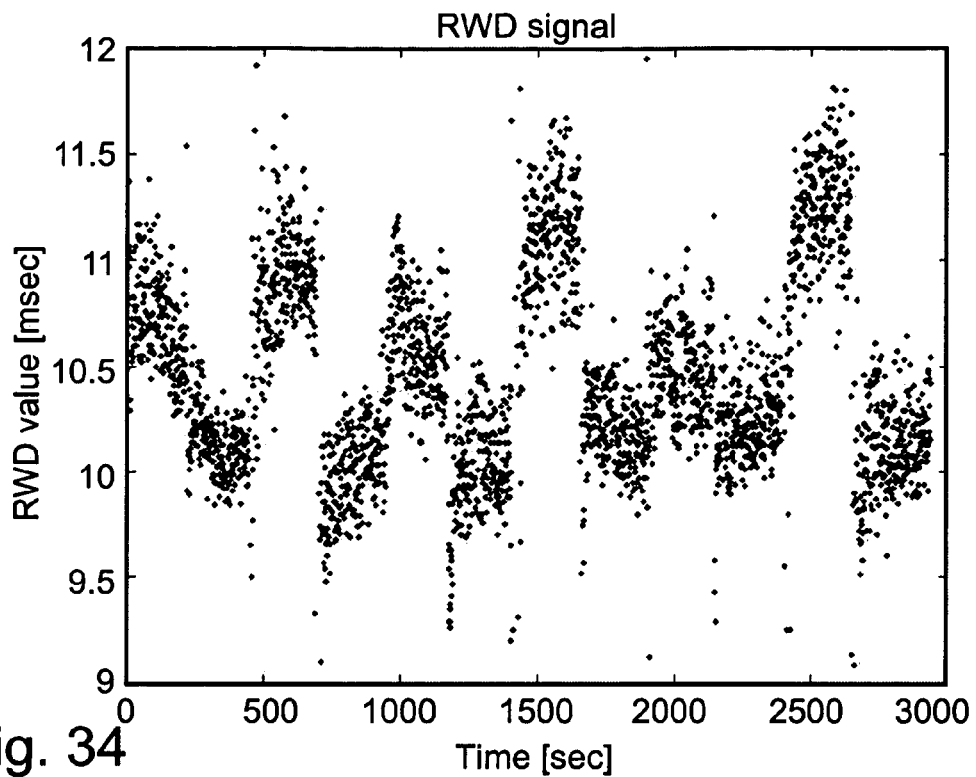
FIG. 34 shows time dependence of the RWD function, calculated from lead II ECG, for a single subject, before a filtering procedure.
Figure 35:
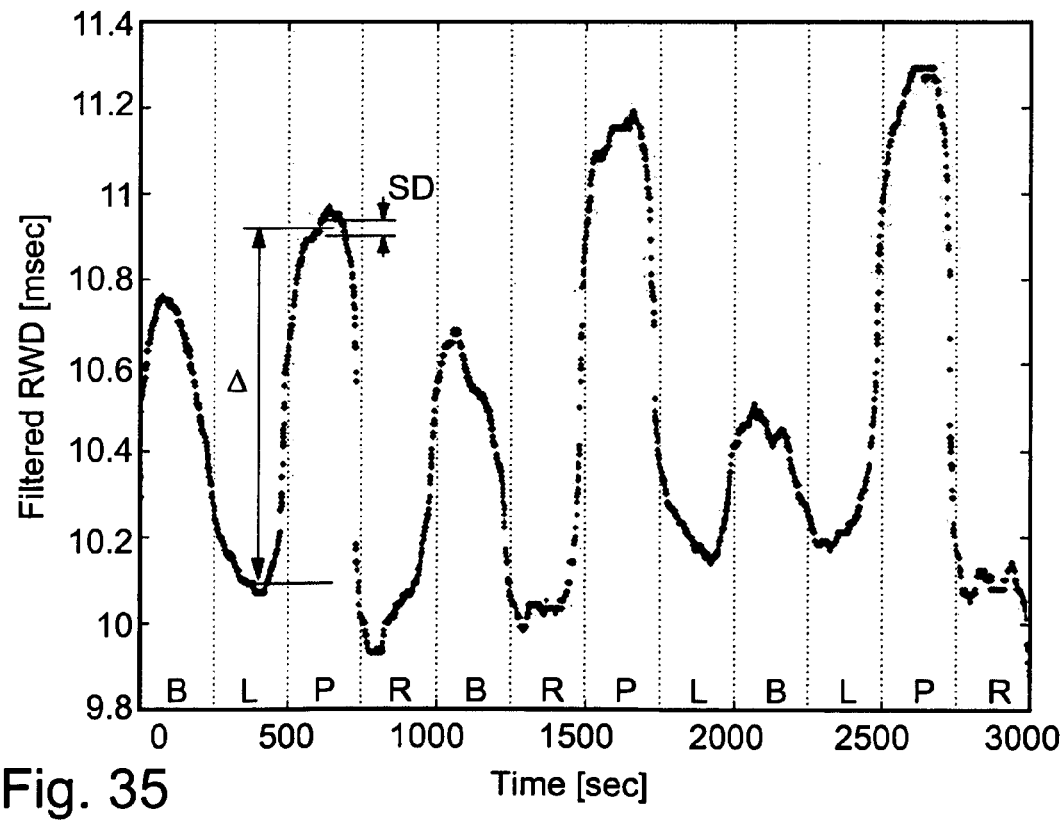
FIG. 35 shows the time dependence of the RWD function, calculated from lead II ECG, for a single subject, after the filtering procedure.

FIGS. 34 and 35 show the time dependence of the RWD function, calculated from lead II ECG, for a single subject, before (FIG. 34) and after (FIG. 35) the filtering. In FIG. 35, different colors indicate different body positions.

Marked step changes in the RWD function are observed every 250 seconds, representing transitions between body positions. The same level of RWD function was approximately maintained throughout each segment of 250 seconds. The ratio between the fluctuations in a specific body position (measured by the standard deviation SD), and the step change, Δ, between two levels of the RWD function in the transition between positions, represents a measure to differentiate between body positions.

For example, in the second position (L), the mean and SD were 10.127±0.047 ms, respectively. The values in the third position (P) were 10.879±0.079 ms, respectively. The difference, Δ, in average RWD values between these two body positions was 0.752 ms. The ratio between the SD and this difference SD/Δ is 0.063 (6.3%), for the left-hand side body position, and 0.105 (10.5%) for the prone position. Similar ratios were calculated for the SD of each body position and the averaged difference between that position and all other positions (SD/avgΔ).

Table 6, below, summarizes the results for each lead.

TABLE 6

| SD/avgΔ | BACK | LEFT | PRONE | RIGHT |
|---|---|---|---|---|
| Lead I: | 5.3% | 14.8% | 11.0% | 15.2% |
| Lead II: | 12.1% | 8.2% | 12.4% | 10.7% |
| Lead III: | 13.9% | 11.5% | 19.9% | 15.0% |
| Average: | 10.4% | 11.5% | 14.4% | 13.6% |

Each cell in the first 4 columns of Table 6 shows the ratio of SD/avgΔ for a specific position, averaged over all subjects. The last column of Table 6 shows the general ratio between average SD for all body positions, and the average difference between any two combinations of body positions in a given lead. The relatively small ratios (5%-20%) indicate that the fluctuations, SD, in the RWD function in a certain body position are small compared to the step changes, Δ, that occur as the subject changes its body position. Using these numbers, one can compare the relative performance of the 3 leads. The last row of Table 6 presents the average of the ratios (SD/avgΔ) for each body position.

These results demonstrate that marked changes can be observed in the RWD function, and that these changes can be used to detect body position changes.

Table 7, below, summarize the number of position changes and the quality of the results as obtained by the method of the present invention.

TABLE 7

| | Lead I | Lead II | Lead III |
|---|---|---|---|
| No. of body position changes | 132 | 132 | 132 |
| No. of events classified as body position changes | 137 | 132 | 135 |
| sensitivity | 94% | 90% | 92% |
| Positive predictive value (PPV) | 91% | 90% | 90% |
| Repeatability coeff. (ms) | 0.642 | 0.206 | 0.450 |
| Avg. RWD change ms) | 0.597 | 0.374 | 0.546 |

The top four rows in table 2 summarize the sensitivity (>90%) and the positive predictive value (~90%) of the body position changes detection algorithm, as defined above. Position changes that were not detected in one lead were usually detectable with the other leads, thus combining data from any two leads, may improve the results. The results of the calculation of the repeatability coefficients are displayed in the fifth row of Table 7. In order to evaluate these results, a limit for a deviation value was calculated as the average change in RWD (over all positions). The last row of table 7 displays these average values. Evidently, lead I has a repeatability coefficient larger than the average inter-body position RWD change, making it unsuitable for specifying body positions. Lead II (with the best result) and lead III have repeatability coefficients smaller than the average change in RWD. They are thus suitable for the final stage of processing that is aimed at separating the heartbeats into four groups (relating to four different body positions) based on the classification technique described.

Figure 36A:
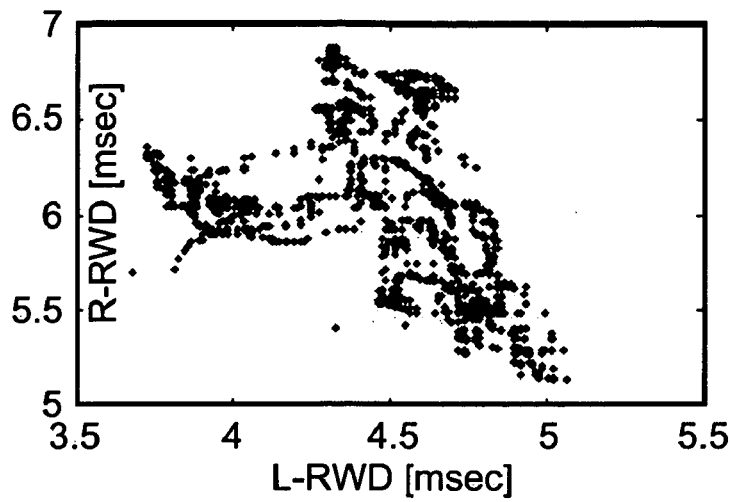
FIG. 36a-c show a two-dimensional phase space, constructed from the RWD function of FIG. 32, for the purpose of classifying 4 different groups.
Figure 36B:
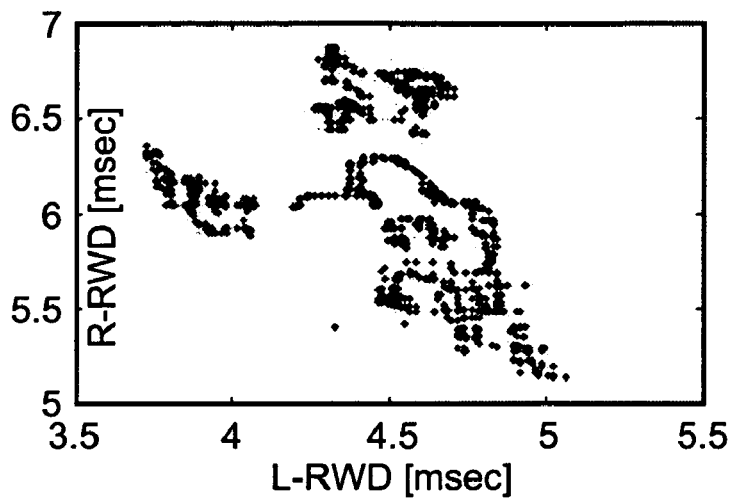
Figure 36C:
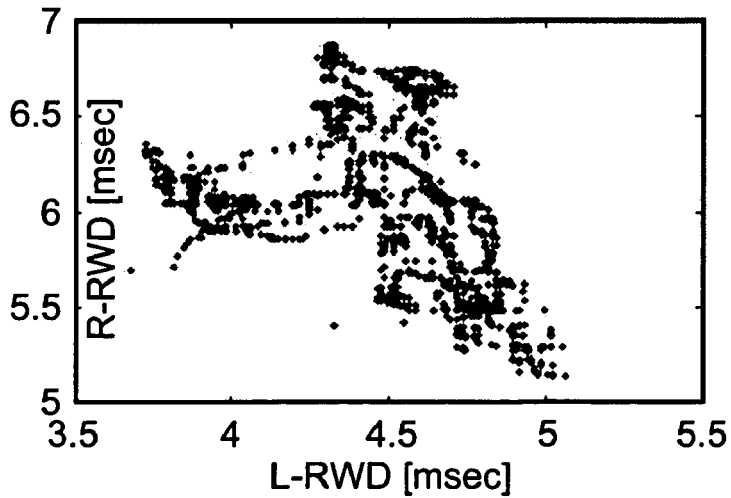

FIGS. 36a-c, show a 2 dimensional phase space, constructed for the purpose of classifying the 4 different groups. In FIGS. 36a-c, the L-RWD is on the abscissa and the R-RWD is on the ordinate. Each point represents one QRS complex.

FIG. 36a shows the phase space prior to the classification, where the four groups of different body positions are not apparent.

FIG. 36b shows the phase space of the reference calcification, as constructed from the known positions.

FIG. 36c shows the results once the K-mean clustering procedure, described above, was applied to relate each point in phase space of FIG. 36a to one of four groups.

Similarly to FIG. 35, the colors in FIG. 36b-c indicate the different clusters (body positions). Note that in some cases, the RWD function of two different postures of the same subject were undistinguishable yet different ratios of the left and right parts of the RWD (L-RWD and R-RWD) facilitates correct classification.

Table 8, below summarizes the results of the clustering procedure.

TABLE 8

|  | Supine | Left | Prone | Right | Total |
|---|---|---|---|---|---|
| 2D Lead II: Sensitivity | 94% | 64% | 84% | 72% | 79% |
| Specificity | 91% | 92% | 94% | 96% | 93% |
| 2D Lead III: Sensitivity | 70% | 83% | 67% | 75% | 74% |
| Specificity | 85% | 92% | 96% | 93% | 92% |
| 4D (II + III): Sensitivity | 97% | 67% | 67% | 83% | 79% |
| Specificity | 88% | 92% | 96% | 95% | 93% |

Discussion of the Results

The relative angle between an ECG lead and the electric axis of the heart changes with body position, and affects the shape of the QRS recorded in that lead. While in many applications this fact is treated as an artifact that should be avoided or eliminated, in the present study, this angle was exploited to identify body position changes, and to classify different body positions.

RWD, measured between two inflection points adjacent to the R wave peak, was introduced as a robust feature of the QRS shape. It has shown to be very sensitive to body position changes, and with its two components L-RWD and R-RWD, capable of classifying four recumbent body positions.

The results presented in Table 6 demonstrate that fluctuations in RWD values, calculated from any of lead I or II or III, at any position, are between 10%-20% of the RWD variation when a position is changed. This result supports the use of RWD measurement as an indicator of body position changes, and explains the achieved detection rates presented in Table 7.

Although, in principle, any of the leads can be used to detect body position changes, with a success rate of over 90%, considering the repeatability coefficients and comparing them to the average change in RWD function, one observes that the performances of the leads differ. Lead I had a repeatability coefficient larger than the average change in RWD function upon changing body position, indicating a somewhat less efficient classification capability, than leads II or III. Lead II achieved the most significant difference between the repeatability coefficient and the average RWD change. The better repeatability results of leads II or III cannot be explained by longer duration of the R-waves in these leads nor by a better resolution for the calculated RWD signal. The results may be explained by the degrees of freedom that the body has at the different locations of the electrodes (in the present study the shoulders vs. the upper thigh). The common electrode location for leads II and III (upper left thigh) has less degrees of freedom, thus it reassumes the same spatial position upon reassuming the same body position.

With respect to the use of the L-RWD and the R-RWD, calculated from leads II and III, as the features for the K-means classifier, lead II had slightly better results with nearly 80% correct classifications of positions (sensitivity) and 93% specificity.

Thus, this work proves that the separation of RWD into at least two components gives additional information that cannot be inferred otherwise. This is apparent in FIG. 35, where certain levels of RWD values were classified into different groups because of the different partition into L-RWD and R-RWD values.

ECG signal monitoring is commonly used, has a good signal-to-noise ratio and is relatively inexpensive. The additional information, during recumbence, as obtained by the method of the present invention, can be extracted from the ECG, with no need for additional channels, no additional data storage place, and most important, no additional inconvenience to the patient. The obtained information is of relevance for sleep studies, Holter monitoring, and various physiologic studies that deal with autonomic function.

Example 9

Incorporating Detection of Body Position with Apnea Detection

In this study the method of detecting body position is incorporated with spectrum analysis for the purpose of efficiently detecting apneic events.

Experimental Methods

The study was performed on a training set data supplied by Physionet database http://www.physionet.org//cinc-challenge-2000.html. The procedure included the steps described in method 130.

Specifically, the database was scanned to construct the RRI series. Two scans were performed, a first scan, in which abnormal beats (les than 1%) were discarded from the series ignored, and a second scan which included all heart beats, and, synthetic heart beats which were and interpolated in case of premature or missing beats. The results of the first scan were used for the purpose of extracting the RWD function, and the second scan was used for the purpose of obtaining the power spectrum, as described above.

Changes of body positions were detected from the results of the first scan using the RWD function (see, e.g., Example 8). According the changes in the body positions, the RRI series of the second scan was dissected into segments were each segment correspond to a single body position. The criterion for accepting a segment for the purpose of further analysis by a discrete transform was a minimal length of 200 seconds. Multiple body position changes during such a period were considered as a single position change.

Awakenings were identified using the by LPF with cutoff frequency of 0.0 Hz, and marking the components under 0.85 of averaged value as wake periods (see also Example 5 and FIGS. 27 and 28 therein). These periods were eliminated from each of the above RRI segments.

The discrete transform was a discrete Fourier transform (DFT), and the power spectrum component was calculated by integrating the power spectrum over the frequency range of 0.01-0.04 Hz. The total power was calculated by integrating the power spectrum over all frequencies below 0.5 Hz, which, to a good accuracy contain most of the power. Denoting the integrated power from 0.01 to 0.04 Hz by AR (apnea range) and the total power by T, every minute in the segment was marked as an apneic event, if the ratio AR/T was larger that 0.5 (i.e., more than 50% of the total power).

All unclassified segments (including short segments) were further processes using a pattern recognition procedure, so as to locate specific U-shaped pattern in the RRI segments. The pattern recognition procedure included detection of transient decreases in the RRI below a threshold of 0.58 seconds. Those minutes in which a U-shape was found, were marked as apneic events, other minutes in the segment were classified as normal.

Experimental Results

Figure 37:
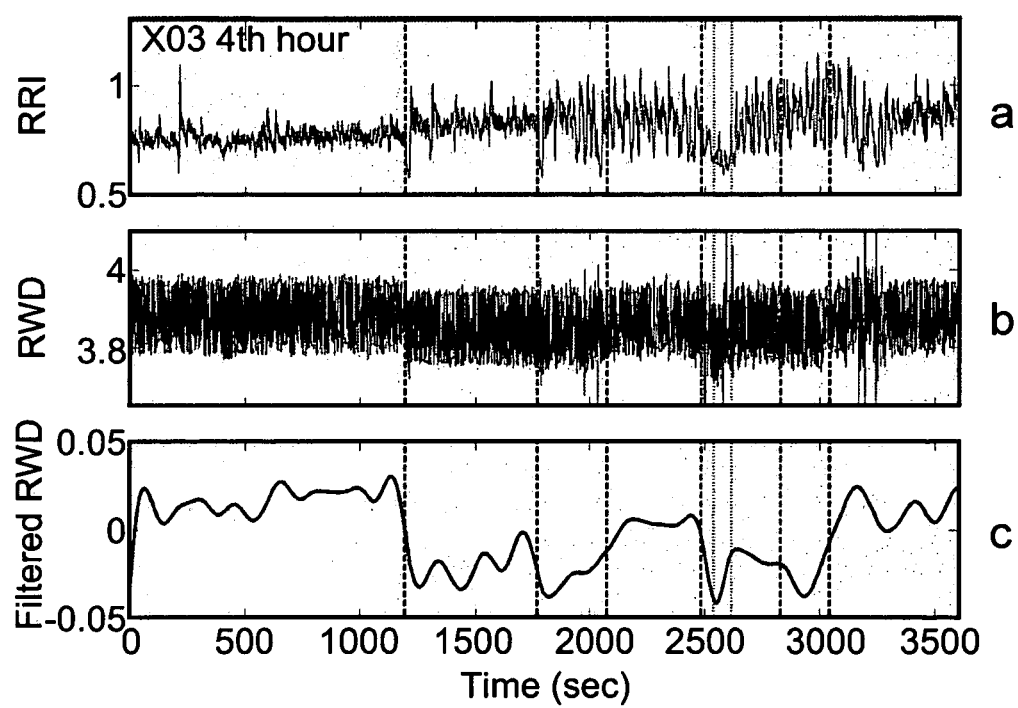
FIGS. 37a-c show results of dissection of an RRI series into a plurality of segments, where each segment corresponds to a different body position.

FIG. 37 shows a typical result of the dissection of the RRI series into segments according to subject's body position. Note that different segments also present different characteristics of the RRI series. This feature was more apparent with apnea segments.

FIGS. 38a-d show the power spectra of three adjacent segments (FIGS. 38b-d) of the RRI series (FIG. 38a). The first spectrum (FIG. 38b), corresponds to the first segment and contains energy in the respiratory range (slightly below 0.3 Hz). The ratio AR/T was below 0.5, hence this segment was not suitable for DFT and was processed by pattern recognition. The next spectrum (FIG. 38d), corresponds with the main central segment from the RRI series, in which AR/T>0.5. Each minute within this segment was marked as apneic with no need to be further processed. The third spectrum (FIG. 38d), was calculated for last short RRI segment right to the main central segment, has most of its energy below the "apnea range," thus was further processed by pattern recognition.

The results of the procedure received the score of 14788 correct minute-by-minute classifications, out of 17268 minutes (~85%) during the recordings. This result is of the same order of the commonly cited inter-observer variability in the sleep diagnosis field.

Conclusions

This study was designed to detect multiple apnea events by means power spectral analysis of the RRI, and identification of sporadic apnea events by tracing a characteristic U-shape in the RRI series.

RRI power spectral analysis may be misleading if applied to periods containing both apneic and normal segments. U-pattern search, on the other hand, may give erroneous results, as this shape also characterizes other events that involve arousals. The combination of the spectral analysis of the RRI and the pattern recognition, allows an efficient detection of apnea substantially devoid of the above problems.

Since apnea is often position related, the segmentation of the entire dataset into single body position segments separate between apneic and non-apneic periods. In addition, the method also avoids the confusion between wake and apnea event by removing awakening periods before the main analysis.

APPENDIX 1

Minimum-Cross-Entropy Method

The cross-entropy distance, subject to data consistency, between a posteriori probability q(x) and a priori distribution p(x) is defined as:

$$H_{CE}(q, p) = \int q_x \log \frac{q_x}{p_x} dx.$$

$H_{CE}$ is also referred to as the relative entropy, Kullback-Leibler number, discrimination information or directed divergence.

For discrete (digital) probability distributions the integration is replaced by summation. The discrete cross-entropy distance between $q_x$ and its prior $p_x$ is then given by:

$$H_{CE}(q, p) = \sum_{x=1}^{N} q_x \log \frac{q_x}{p_x}$$

and subject to the completeness relation:

$$\sum_{x=1}^{N} p_x = \sum_{x=1}^{N} q_x = 1,$$

where N is the number of discrete bins in the distribution.

One may view a signal as a composition of N oscillators having L different frequencies. The spectral decomposition of the signal reveals a distribution of frequencies, which may be regarded as the a posteriori distribution $(f_1, f_2 \ldots f_N)$, while the original frequency distribution of the source oscillators, may constitute the prior distribution $(v_1, v_2 \ldots v_N)$. The relative strength (probability of occurrence: $h_1 \ldots h_N$) to of each frequency, $f_i$, obtained through the power spectrum calculation, allows summation over the L different frequency levels when calculating the cross-entropy term:

$$H_{CE}(f, v) = \sum_{i=1}^{L} h_i f_i \log \frac{f_i}{v_i}$$

Taking T as the index of a threshold frequency, the below- and above-threshold mean frequency values, $\mu_0(T)$ and $\mu_1(T)$, respectively, can be used as estimators of the frequencies of the original oscillators modulating the signal (assuming there are only two):

$$\mu_0(T) = \frac{\sum_{i=1}^{T} h_i f_i}{\sum_{i=1}^{T} h_i}, \text{ and}$$

$$\mu_1(T) = \frac{\sum_{i=T+1}^{L} h_i f_i}{\sum_{i=T+1}^{L} h_i}.$$

Thus, replacing $(v_1, v_2 \ldots v_N)$ with $(\mu_0(T), \mu_1(T))$, the cross-entropy measure becomes:

$$H_{CE}(T) = \sum_{i=1}^{T} h_i f_i \log \frac{f_i}{\mu_0(T)} + \sum_{i=T+1}^{L} h_i f_i \log \frac{f_i}{\mu_1(T)}.$$

The threshold frequency $f_T$ that minimizes this expression, best estimates the separating limit between the two original frequencies modulating the signal. The simplest and most direct scheme for threshold selection would be to iterate through all possible threshold values, T, and to select the threshold corresponding to the minimum of the cross-entropy.

A skilled artisan would appreciate that although $H_{CE}$, $\mu_0$ and $\mu_t$ use non-normalized frequency distributions (and therefore do not constitute probability distributions as required by the principles of information theory), those distributions can be normalized at the expense of an additive constant to $H_{CE}$, which is not dependent on the threshold T.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of determining a Slow-Wave-Sleep (SWS) period and a Non-SWS (NSWS) period from signals of electrical activity recorded of a chest of a sleeping subject, the signals being measured over a plurality of epochs, the method comprising:
    extracting a series of cardiac R-R intervals from the signals and obtaining a time-frequency decomposition from said series of cardiac R-R intervals; and
    using said time-frequency decomposition to determine a SWS period defined over a plurality of SWS epochs, thereby also determining NSWS period defined by all epochs other than said SWS epochs, said NSWS period encompassing at least one Rapid-Eye-Movement (REM) sleep period and at least one Non-REM (NREM) sleep period;
    thereby determining the SWS period and the NSWS period of the sleeping subject.

2. The method of claim 1, wherein said obtaining said time-frequency decomposition comprises calculating, for each epoch, at least one time-dependent power spectrum component selected from the group consisting of a very-low-frequency (VLF) power spectrum, a low-frequency (LF) power spectrum and a high-frequency (HF) power spectrum.

3. The method of claim 2, wherein the SWS period is defined by a plurality of epochs, each characterized by at least one power parameter which is below a predetermined threshold, said at least one power parameter is selected from the group consisting of said VLF power spectrum, said LF power spectrum, said HF power spectrum, and a combination between two of said VLF, said LF and said HF power spectra.

4. The method of claim 3, wherein said combination is a ratio.

5. The method of claim 2, wherein said predetermined threshold is constant.

6. The method of claim 2, wherein said predetermined threshold is a first function of an average value of said at least one power parameter.

7. The method of claim 6, wherein said first function is a linear function.

8. The method of claim 2, wherein said predetermined threshold varies with time.

9. The method of claim 2, wherein at least one of said VLF, said LF and said HF power spectra are calculated within a window along said series of cardiac R-R intervals, said window being characterized by a duration which is a function of a respective frequency.

10. The method of claim 9, wherein said function of said respective frequency is inversely related to said respective frequency.

11. The method of claim 9, wherein said window has an aperture selected from the group consisting of: a rectangular aperture, a Hamming aperture, a Hanning aperture, a Blackman aperture, a Gaussian window, a Lorentzian window, a sinc window, a power of a sine window and a power of a cosine window.

12. The method of claim 9, further comprising determining a frequency resolution.

13. The method of claim 12, wherein said frequency resolution is from 0.001 Hz to 0.03 Hz.

14. The method of claim 9, further comprising determining a time resolution.

15. The method of claim 14, wherein said time resolution is from 1 second to 30 seconds.

16. The method of claim 9, further comprising determining an onset and a termination of said time-dependent power spectra.

17. The method of claim 9, wherein at least one of said VLF, said LF and said HF power spectra are calculated by a wavelet transform.

18. The method of claim 17, wherein said wavelet transform is selected from the group consisting of a discrete wavelet transform and a continuous wavelet transform.

19. The method of claim 9, wherein at least one of said VLF, said LF and said HF power spectra are calculated by a selective discrete spectral transform.

20. The method of claim 19, wherein said selective discrete spectral transform is selected from the group consisting of: a Fourier transform, a Haar transform, a Hartley transform, a sine transform, a cosine transform, and a Hadamard transform.

21. A method of determining a Rapid-Eye-Movement (REM) sleep and a Non-REM (NREM) sleep from signals of electrical activity recorded of a chest of a sleeping subject, the signals being measured over a plurality of epochs, the method comprising:
    extracting a plurality of electromyogram (EMG) parameters from the signals; and
    using said plurality of EMG parameters to determine at least one REM period;

thereby determining the REM sleep and the NREM sleep of the sleeping subject.

22. The method of claim 21, wherein said extracting said plurality of EMG parameters is effected by at least one procedure selected from the group consisting of: eliminating P waves, eliminating T waves and eliminating QRS-complexes from the signals.

23. The method of claim 22, wherein said eliminating P waves and said eliminating T waves from the signals is by high pass filtering.

24. The method of claim 23, wherein said high pass filtering is at a threshold frequency of about 10 Hz.

25. The method of claim 22, wherein said eliminating QRS complexes is by a combination of gating and/or subtraction.

26. The method of claim 21, wherein said plurality of EMG parameters are selected from the group consisting of: normalized amplitude (mrEMG), normalized mean power (nPWR), zero-crossing average (ZC), median frequency (MF), mean power frequency (MPF), Expected Zero Crossing (EZC), power variance (PVAR), turns (NT) and Complexity (Cmplx).

27. The method of claim 21, wherein the REM sleep is defined by a plurality of epochs, each characterized by at least one of said plurality of EMG parameters which is below a predetermined threshold.

28. A method of determining a Rapid-Eye-Movement (REM) sleep and a Non-REM (NREM) sleep from signals of electrical activity recorded of a chest of a sleeping subject, the signals being measured over a plurality of epochs, the method comprising:
   extracting a series of cardiac R-R intervals from the signals;
   constructing a Poincare plot of said series of cardiac R-R intervals; and
   using said Poincare plot to determine the REM sleep and the NREM sleep of the sleeping subject.

29. The method of claim 28, further comprising calculating a plurality of moments with respect to a predetermined line along said Poincare plot, each of said plurality of moments being calculated within a predetermined time-window.

30. The method of claim 29, wherein said plurality of moments is a plurality of moments of inertia.

31. The method of claim 29, wherein the REM sleep is defined by a plurality of epochs, each characterized by a moment which is below a predetermined threshold.

32. The method of claim 29, wherein said predetermined line along said Poincare plot is a straight line, forming a predetermined angle with respect to an axis of said Poincare plot.

33. The method of claim 32, wherein said predetermined angle equals about 45 degrees.

34. The method of claim 29, further comprising normalizing each of said plurality of moments.

35. A method of determining sleep stages from signals of electrical activity recorded of a chest of a sleeping subject, the signals being measured over a plurality of epochs, the method comprising:
   extracting a series of cardiac R-R intervals from the signals and obtaining a time-frequency decomposition from said series of cardiac R-R intervals;
   using said time-frequency decomposition to determine at least one Slow-Wave-Sleep (SWS) period and at least one Non-SWS (NSWS) period;
   from said at least one NSWS period, determining at least one sleep-onset (SO) period and a plurality of non-sleep periods;
   extracting a plurality of electromyogram (EMG) parameters from a portion of the signals, said portion corresponds to a NSWS period other than said at least one SO period and other than said plurality of non-sleep period;
   using said plurality of EMG parameters to determine at least one REM period, thereby obtaining also at least one light-sleep (LS) period defined as a NSWS period other than said at least one SO period, other than said plurality of non-sleep periods and other than said at least one REM period;
   thereby determining the sleep stages of the sleeping subject.

36. The method of claim 35, further comprising determining, from said at least one LS period, at least one Stage-2 period thereby obtaining also a Stage-1 period, said Stage-1 period being defined as a LS period other than said at least one Stage-2.

37. The method of claim 35, wherein said obtaining said time-frequency decomposition comprises calculating, for each epoch, at least one time-dependent power spectrum component selected from the group consisting of a very-low-frequency (VLF) power spectrum, a low-frequency (LF) power spectrum and a high-frequency (HF) power spectrum.

38. The method of claim 37, wherein the SWS period is defined by a plurality of epochs, each characterized by at least one power parameter which is below a predetermined threshold, said at least one power parameter is selected from the group consisting of said VLF power spectrum, said LF power spectrum, said HF power spectrum, and a combination between two of said VLF, said LF and said HF power spectra.

39. The method of claim 38, wherein said combination is a ratio.

40. The method of claim 37, wherein said predetermined threshold is constant.

41. The method of claim 37, wherein said predetermined threshold is a first function of an average value of said at least one power parameter.

42. The method of claim 41, wherein said first function is a linear function.

43. The method of claim 37, wherein said predetermined threshold varies with time.

44. The method of claim 37, wherein at least one of said VLF, said LF and said HF power spectra are calculated within a window along said series of cardiac R-R intervals, said window being characterized by a duration which is a function of a respective frequency.

45. The method of claim 44, wherein said function of said respective frequency is inversely related to said respective frequency.

46. The method of claim 44, wherein said window has an aperture selected from the group consisting of: a rectangular aperture, a Hamming aperture, a Hanning aperture, a Blackman aperture, a Gaussian window, a Lorentzian window, a sinc window, a power of a sine window and a power of a cosine window.

47. The method of claim 44, further comprising determining a frequency resolution.

48. The method of claim 47, wherein said frequency resolution is from 0.001 Hz to 0.03 Hz.

49. The method of claim 44, further comprising determining a time resolution.

50. The method of claim 49, wherein said time resolution is from 1 second to 30 seconds.

51. The method of claim 44, further comprising determining an onset and a termination of said time-dependent power spectra.

52. The method of claim 44, wherein at least one of said VLF, said LF and said HF power spectra are calculated by a wavelet transform.

53. The method of claim 52, wherein said wavelet transform is selected from the group consisting of a discrete wavelet transform and a continuous wavelet transform.

54. The method of claim 44, wherein at least one of said VLF, said LF and said HF power spectra are calculated by a selective discrete spectral transform.

55. The method of claim 54, wherein said selective discrete spectral transform is selected from the group consisting of: a Fourier transform, a Haar transform, a Hartley transform, a sine transform, a cosine transform, and a Hadamard transform.

56. The method of claim 37, wherein said determining at least one SO period comprises calculating at least one SO parameter and defining the SO period to be at least one epoch being characterized by at least one SO parameter which is above a predetermined threshold, over a predetermined time range.

57. The method of claim 56, wherein said predetermined time range is from 2 epochs to 10 epochs.

58. The method of claim 56, wherein said at least one SO parameter comprises at least one integrated power spectrum calculated by integrating at least one of said power spectra over predetermined frequency limits.

59. The method of claim 58, wherein said at least one SO parameter further comprises at least one time-dependent power ratio calculated using said at least one integrated power spectrum.

60. The method of claim 58, further comprising calculating said predetermined frequency limits.

61. The method of claim 60, wherein said calculating said predetermined frequency limits comprises obtaining a steady state power spectrum from series of cardiac R-R intervals, and applying a minimum-cross-entropy method on said steady state power spectrum, so as to provide said frequency limits.

62. The method of claim 61, wherein said minimum-cross-entropy method is executed so as to separate between frequency peaks of said steady state power spectrum.

63. The method of claim 56, further comprising normalizing said at least one SO parameter.

64. The method of claim 56, further comprising analyzing said at least one SO parameter using a plurality of statistical quantities.

65. The method of claim 64, wherein said plurality of statistical quantities selected from the group consisting of an average, a variance and a t-test.

66. The method of claim 35, wherein said plurality of non-sleep periods comprises at least one awakening period and/or at least one arousal period.

67. The method of claim 66, further comprising:
(a) filtering said series of cardiac R-R intervals using a low-pass-filter, thereby providing a first series of signals; and
(b) defining said at least one awakening period as a plurality of epochs each associated with at least one of said first series of signals which is below a predetermined threshold.

68. The method of claim 67, wherein said low-pass-filter is at about 0.01 Hz.

69. The method of claim 67, wherein said predetermined threshold is about 0.85 of an averaged value of said first series of signals.

70. The method of claim 66, further comprising:
(a) filtering said series of cardiac R-R intervals using a band-pass-filter, thereby providing a second series of signals; and
(b) defining said at least one arousal period as a plurality of epochs each associated with at least one of said second series of signals which is below a predetermined threshold.

71. The method of claim 70, wherein said band-pass-filter is characterized by a lower band limit of about 0.05 Hz and an upper band limit of about 0.2 Hz.

72. The method of claim 70, wherein said predetermined threshold is about 0.85 of an averaged value of said second series of signals.

73. The method of claim 35, wherein said extracting a plurality of EMG parameters is effected by at least one procedure selected from the group consisting of: eliminating P waves, eliminating T waves and eliminating QRS-complexes from the signals.

74. The method of claim 73, wherein said eliminating P waves and said eliminating T waves from the signals is by high pass filtering.

75. The method of claim 74, wherein said high pass filtering is at a threshold frequency of about 10 Hz.

76. The method of claim 73, wherein said eliminating QRS complexes is by a combination of gating and/or subtraction.

77. The method of claim 35, wherein said plurality of EMG parameters are selected from the group consisting of: normalized amplitude (mrEMG), normalized mean power (nPWR), zero-crossing average (ZC), median frequency (MF), mean power frequency (MPF), Expected Zero Crossing (EZC), power variance (PVAR), turns (NT) and Complexity (Cmplx).

78. The method of claim 35, wherein the REM sleep is defined by a plurality of epochs, each characterized by at least one of said plurality of EMG parameters which is below a predetermined threshold.

79. The method of claim 35, wherein said at least one Stage-2 period is defined by a plurality of epochs, each associated to a cardiac R-R interval corresponding to a K-complex.

80. The method of claim 79, wherein said cardiac R-R interval corresponding to said K-complex is characterized by a specific width and a specific depth.

81. A method of determining a body position or a change in the body position from signals of electrical activity recorded of a chest of a sleeping subject, the signals being characterized by QRS complexes, the method comprising:
extracting R-wave durations from the QRS complexes, thereby obtaining an R-wave duration (RWD) function; and
using said RWD function to determine the body position or the change in the body position of the sleeping subject.

82. The method of claim 81, wherein the change in the body position is defined when a change of said RWD function is above a predetermined threshold.

83. The method of claim 82, wherein said predetermined threshold is a standard deviation of said RWD function.

84. The method of claim 82, wherein said change of said RWD function is calculated using at least one local average of said RWD function.

85. The method of claim 82, wherein said change of said RWD function is defined as a difference between two Local averages of said RWD function.

86. The method of claim 81, wherein the body position is one of two body positions.

87. The method of claim 86, wherein said two body positions, comprise a first body position, defined when a value of said RWD function is high and a second body position, defined when a value of said RWD function is low.

88. The method of claim 81, further comprising defining at least two segments of each of the QRS complexes and determining width of each of said at least two segments, thereby obtaining, for each QRS complex, a set of widths, said set being representative of the body position.

89. The method of claim 88, wherein each of said segments has a first endpoint and a second endpoint, said first and said second endpoints being characterized by a zero nth-order derivative of a respective R-wave of said QRS complex, where n is a positive integer.

90. The method of claim 81, wherein said at least two segments comprise a left segment and a right segment and the body position is one of four body positions.

91. The method of claim 90, wherein said four body positions comprise:
a first body position, defined when a value of said left segment is high and a value of said right segment is high;
a second body position, defined when a value of said left segment is low and a value of said right segment is high;
a third body position, defined when a value of said left segment is high and a value of said right segment is low; and
a fourth body position, defined when a value of said left segment is low and a value of said right segment is low.

92. The method of claim 88, further comprising applying a clustering procedure on each said sets of widths, so as to define a plurality of clusters, each one of said plurality of clusters corresponding to a different body position.

93. The method of claim 92, wherein said clustering procedure is selected from the group consisting of graph theory procedure, density estimation procedure, Potts-spins-based procedure, hierarchical procedure and partitional procedure.

94. The method of claim 93, wherein said partitioned procedure is selected from the group consisting of a K-means procedure, an adaptive K-means procedure, hard C-means procedure and fuzzy C-means procedure.

95. The method of claim 93, wherein said hierarchical procedure is selected from the group consisting of a nearest neighbor procedure and a minimal spanning tree procedure.

96. A method of determining a sleep apnea from signals of electrical activity recorded of a chest of a sleeping subject, the signals being measured over a plurality of epochs, the method comprising:
(a) extracting a series of cardiac R-R intervals from the signals;
(b) determining awakening periods of the sleeping subject and excluding cardiac R-R intervals corresponding to said awakening periods from said series of cardiac R-R intervals;
(c) obtaining a power spectrum from said series of cardiac R-R intervals; and
(d) using said power spectrum to determine the sleep apnea of the sleeping subject.

97. The method of claim 96, further comprising determining body positions or a change in a body position of the sleeping subject prior to said step (b), and executing said steps (b)-(d) separately for each one of said body positions.

98. The method of claim 96, wherein said determining said awakening periods of said step (b) comprises:
(i) filtering said series of cardiac R-R intervals using a low-pass-filter, thereby providing a first series of signals; and
(ii) defining said awakening periods as a plurality of epochs each associated with at least one of said first series of signals which is below a predetermined threshold.

99. The method of claim 98, wherein said low-pass-filter is at about 0.01 Hz.

100. The method of claim 98, wherein said predetermined threshold is about 0.85 of an averaged value of said first series of signals.

101. The method of claim 96, wherein said obtaining said power spectrum is by a discrete transform.

102. The method of claim 101, wherein said discrete transform is selected from the group consisting of a steady state discrete transform and a time-dependent discrete transform.

103. The method of claim 101, wherein said discrete transform is selected from the group consisting of a discrete Fourier transform, a discrete Hartley transform, a discrete sine transform, a discrete cosine transform, a discrete Hadamard transform, a discrete Haar transform and a discrete wavelet transform.

104. The method of claim 96, wherein said step (d) comprises obtaining, for each period other than said awakening period, a power spectrum component of said power spectrum, and if said power spectrum component is above a predetermined threshold then identifying sleep apnea for said period.

105. The method of claim 104, wherein said power spectrum component is power of signals being at a frequency range representing sleep apnea.

106. The method of claim 105, wherein said frequency range is from about 0.01 Hz to about 0.04 Hz.

107. The method of claim 104, wherein said predetermined threshold is about half of a total power of said power spectrum.

108. The method of claim 97, further comprising:
employing a pattern recognition procedure on a portion of said series of cardiac R-R intervals, so as to identify representative patterns of sleep apnea; and
identifying periods corresponding to said representative patterns as sleep apnea periods.

109. The method of claim 108, wherein said portion of said series of cardiac R-R intervals corresponds to body positions having durations lower than a predetermined threshold.

110. The method of claim 109, wherein said predetermined threshold equals about 200 seconds plus total awakening time in a respective body position.

111. The method of claim 108, wherein said portion of said series of cardiac R-R intervals corresponds to periods characterized by a power spectrum component which is below a predetermined threshold, said power spectrum component is power of signals being at a frequency range representing sleep apnea.

112. The method of claim 111, wherein said predetermined threshold is about half of a total power of said power spectrum.

113. The method of claim 108, wherein said representative patterns are characterized by a U-shape of said cardiac R-R intervals.

114. The method of claim 96, further comprising discarding signals corresponding to abnormal heart beats of the sleeping subject, prior to said step (a).

115. The method of claim 96, further comprising interpolating the signals so as to compensate missing heart beats of the sleeping subject, prior to said step (a).

116. An apparatus for determining a Slow-Wave-Sleep (SWS) period and a Non-SWS (NSWS) period from signals of electrical activity recorded of a chest of a sleeping subject, the signals being measured over a plurality of epochs, the apparatus comprising:

an R-R extractor for extracting a series of cardiac R-R intervals from the signals;
a decomposer for obtaining a time-frequency decomposition from said series of cardiac R-R intervals; and
an SWS determinator, for using said time-frequency decomposition so as to determine a SWS period defined over a plurality of SWS epochs, thereby also determining NSWS period defined by all epochs other than said SWS epochs, said NSWS period encompassing at least one Rapid-Eye-Movement (REM) sleep period and at least one Non-REM (NREM) sleep period;
thereby to determine the SWS period and the NSWS period of the sleeping subject.

117. The apparatus of claim 116, wherein said decomposer is operable to calculate, for each epoch, at least one time-dependent power spectrum component selected from the group consisting of a very-low-frequency (VLF) power spectrum, a low-frequency (LF) power spectrum and a high-frequency (HF) power spectrum.

118. The apparatus of claim 117, wherein said SWS determinator is programmed to define the SWS period by a plurality of epochs, each characterized by at least one power parameter which is below a predetermined threshold, said at least one power parameter is selected from the group consisting of said VLF power spectrum, said LF power spectrum, said HF power spectrum, and a combination between two of said VLF, said LF and said HF power spectra.

119. The apparatus of claim 118, wherein said combination is a ratio.

120. The apparatus of claim 117, wherein said predetermined threshold is constant.

121. The apparatus of claim 117, wherein said predetermined threshold is a first function of an average value of said at least one power parameter.

122. The apparatus of claim 121, wherein said first function is a linear function.

123. The apparatus of claim 117, wherein said predetermined threshold varies with time.

124. The apparatus of claim 117, wherein said decomposer is operable to calculate said VLF, said LF and said HF power spectra within a window along said series of cardiac R-R intervals, said window being characterized by a duration which is a function of a respective frequency.

125. The apparatus of claim 124, wherein said function of said respective frequency is inversely related to said respective frequency.

126. The apparatus of claim 124, wherein said window has an aperture selected from the group consisting of: a rectangular aperture, a Hamming aperture, a Hanning aperture, a Blackman aperture, a Gaussian window, a Lorentzian window, a sinc window, a power of a sine window and a power of a cosine window.

127. The apparatus of claim 124, wherein said decomposer comprises a wavelet processor.

128. The apparatus of claim 127, wherein said wavelet processor is selected from the group consisting of a discrete wavelet processor and a continuous wavelet processor.

129. The apparatus of claim 124, wherein said decomposer comprises a selective discrete spectral processor.

130. The apparatus of claim 129, wherein said decomposer further comprises a spectral transform selector for selecting a transform from the group consisting of: a Fourier transform, a Haar transform, a Hartley transform, a sine transform, a cosine transform, and a Hadamard transform.

131. An apparatus for determining a Rapid-Eye-Movement (REM) sleep and a Non-REM (NREM) sleep from signals of electrical activity recorded of a chest of a sleeping subject, the signals being measured over a plurality of epochs, the apparatus comprising:
an electromyogram (EMG) extractor for extracting a plurality of EMG parameters from the signals; and
a REM determinator for using said plurality of EMG parameters to determine the REM sleep and the NREM sleep of the sleeping subject.

132. The apparatus of claim 131, wherein said EMG extractor comprises an eliminator for eliminating at least one signal selected from the group consisting of: a P wave, a T wave and a QRS-complex.

133. The apparatus of claim 132, wherein said eliminator comprises at least one high pass filter for filtering out said P wave and said T wave.

134. The apparatus of claim 133, wherein said high pass filter is characterized by a threshold frequency of about 10 Hz.

135. The apparatus of claim 132, wherein said eliminator is operable comprises to eliminate said QRS-complex by a combination of gating and/or subtraction.

136. The apparatus of claim 131, wherein said plurality of EMG parameters are selected from the group consisting of: normalized amplitude (mrEMG), normalized mean power (nPWR), zero-crossing average (ZC), median frequency (MF), mean power frequency (MPF), Expected Zero Crossing (EZC), power variance (PVAR), turns (NT) and Complexity (Cmplx).

137. The apparatus of claim 131, wherein said REM determinator is programmed to define the REM period by a plurality of epochs, each characterized by at least one of said plurality of EMG parameters which is below a predetermined threshold.

138. An apparatus for determining a Rapid-Eye-Movement (REM) sleep and a Non-REM (NREM) sleep from signals of electrical activity recorded of a chest of a sleeping subject, the signals being measured over a plurality of epochs, the apparatus comprising:
an R-R extractor, for extracting a series of cardiac R-R intervals from the signals;
a plotter, for constructing a Poincare plot of said series of cardiac R-R intervals; and
a REM determinator, for using said Poincare plot to determine the REM sleep and the NREM sleep of the sleeping subject.

139. The apparatus of claim 138, further comprising electronic-calculating functionality for calculating a plurality of moments with respect to a predetermined line along said Poincare plot, each of said plurality of moments being calculated within a predetermined time-window.

140. The apparatus of claim 139, wherein said plurality of moments is a plurality of moments of inertia.

141. The apparatus of claim 139, wherein said REM determinator is programmed to define the REM period by a plurality of epochs, each characterized by a moment which is below a predetermined threshold.

142. The apparatus of claim 139, wherein said predetermined line along said Poincare plot is a straight line, forming a predetermined angle with respect to an axis of said Poincare plot.

143. The apparatus of claim 142, wherein said predetermined angle equals about 45 degrees.

144. The apparatus of claim 139, further comprising electronic-calculating functionality for normalizing each of said plurality of moments.

145. An apparatus for determining sleep stages from signals of electrical activity recorded of a chest of a sleeping subject, the signals being measured over a plurality of epochs, the apparatus comprising:
- a R-R extractor for extracting a series of cardiac R-R intervals from the signals;
- a decomposer, for obtaining a time-frequency decomposition from said series of cardiac R-R intervals;
- a Slow-Wave-Sleep (SWS) determinator for using said time-frequency decomposition to determine at least one SWS period and at least one Non-SWS (NSWS) period;
- a sleep-onset (SO) determinator for determining at least one SO period onset period from said at least one NSWS period;
- a non-sleep determinator for determining plurality of non-sleep periods from said at least one NSWS period;
- an electromyogram (EMG) extractor, for extracting a plurality of EMG parameters from a portion of the signals, said portion corresponds to a NSWS period other than said at least one SO period and other than said plurality of non-sleep periods;
- a Rapid-Eye-Movement (REM) determinator for using said plurality of EMG parameters to determine at least one REM period, thereby to obtain also at least one LS period defined as a NSWS period other than said at least one SO period, other than said plurality of non-sleep periods and other than said at least one REM period;
- thereby to determine the sleep stages of the sleeping subject.

146. The apparatus of claim 145, further comprising a Stage-2 determinator for determining, from said at least one LS period, at least one Stage-2 period, thereby to obtain also a Stage-1 period, said Stage-1 period being defined as a LS period other than at least one Stage-2 period.

147. The apparatus of claim 145, wherein said decomposer is operable to calculate, for each epoch, at least one time-dependent power spectrum component selected from the group consisting of a very-low-frequency (VLF) power spectrum, a low-frequency (LF) power spectrum and a high-frequency (HF) power spectrum.

148. The apparatus of claim 147, wherein said SWS determinator is programmed to define the SWS period by a plurality of epochs, each characterized by at least one power parameter which is below a predetermined threshold, said at least one power parameter is selected from the group consisting of said VLF power spectrum, said LF power spectrum, said HF power spectrum, and a combination between two of said VLF, said LF and said HF power spectra.

149. The apparatus of claim 148, wherein said combination is a ratio.

150. The apparatus of claim 147, wherein said predetermined threshold is constant.

151. The apparatus of claim 147, wherein said predetermined threshold is a first function of an average value of said at least one power parameter.

152. The apparatus of claim 151, wherein said first function is a linear function.

153. The apparatus of claim 147, wherein said predetermined threshold varies with time.

154. The apparatus of claim 147, wherein said decomposer is operable to calculate said VLF, said LF and said HF power spectra within a window along said series of cardiac R-R intervals, said window being characterized by a duration which is a function of a respective frequency.

155. The apparatus of claim 154, wherein said function of said respective frequency is inversely related to said respective frequency.

156. The apparatus of claim 154, wherein said window has an aperture selected from the group consisting of: a rectangular aperture, a Hamming aperture, a Hanning aperture, a Blackman aperture, a Gaussian window, a Lorentzian window, a sinc window, a power of a sine window and a power of a cosine window.

157. The apparatus of claim 154, wherein said decomposer comprises a wavelet processor.

158. The apparatus of claim 157, wherein said wavelet processor is selected from the group consisting of a discrete wavelet processor and a continuous wavelet processor.

159. The apparatus of claim 154, wherein said decomposer comprises a selective discrete spectral processor.

160. The apparatus of claim 159, wherein said decomposer further comprises a spectral transform selector for selecting a transform from the group consisting of: a Fourier transform, a Haar transform, a Hartley transform, a sine transform, a cosine transform, and a Hadamard transform.

161. The apparatus of claim 147, wherein said SO determinator comprises electronic-calculating functionality for calculating at least one SO parameter and for defining the SO period to be at least one epochs being characterized by at least one SO parameter which is above a predetermined threshold, over a predetermined time range.

162. The apparatus of claim 161, wherein said predetermined time range is from 2 epochs to 10 epochs.

163. The apparatus of claim 161, wherein said at least one SO parameter comprises at least one integrated power spectrum calculated by integrating at least one of said power spectra over predetermined frequency limits.

164. The apparatus of claim 163, wherein said at least one SO parameter further comprises at least one time-dependent power ratio calculated using said at least one integrated power spectrum.

165. The apparatus of claim 163, wherein said SO determinator further comprises electronic-calculating functionality for calculating said predetermined frequency limits.

166. The apparatus of claim 161, further comprising electronic-calculating functionality for normalizing said at least one SO parameter.

167. The apparatus of claim 161, further comprising a statistical analyzer for analyzing said at least one SO parameter using a plurality of statistical quantities.

168. The apparatus of claim 167, wherein said plurality of statistical quantities selected from the group consisting of an average, a variance and a t-test.

169. The apparatus of claim 145, wherein said plurality of non-sleep periods comprises at least one awakening period and/or at least one arousal period.

170. The apparatus of claim 169, wherein said non-sleep determinator comprises:
- (a) a low-pass filter for filtering said series of cardiac R-R intervals, thereby to provide a first series of signals; and
- (b) an awakening period definer for defining said at least one awakening period as a plurality of epochs each associated with at least one of said first series of signals which is below a predetermined threshold.

171. The apparatus of claim 170, wherein said low-pass-filter is at about 0.01 Hz.

172. The apparatus of claim 170, wherein said predetermined threshold is about 0.85 of an averaged value of said first series of signals.

173. The apparatus of claim 169, wherein said non-sleep determinator comprises:
- (a) a band-pass-filter for filtering said series of cardiac R-R intervals, thereby providing a second series of signals; and (b) an arousal period definer for defining said at least one arousal period as a plurality of epochs each associated with at least one of said second series of signals which is below a predetermined threshold.

174. The apparatus of claim 173, wherein said band-pass-filter is characterized by a lower band limit of about 0.05 Hz and an upper band limit of about 0.2 Hz.

175. The apparatus of claim 173, wherein said predetermined threshold is about 0.85 of an averaged value of said second series of signals.

176. The apparatus of claim 169, wherein said predetermined profile is characterized by a specific width and a specific depth.

177. The apparatus of claim 145, wherein said EMG extractor comprises an eliminator for eliminating at least one signal selected from the group consisting of: a P wave, a T wave and a QRS-complex.

178. The apparatus of claim 177, wherein said eliminator comprises at least one high pass filter for filtering out said P wave and said T wave.

179. The apparatus of claim 178, wherein said high pass filter is characterized by a threshold frequency of about 10 Hz.

180. The apparatus of claim 177, wherein said eliminator is operable comprises to eliminate said QRS-complex by a combination of gating and/or subtraction.

181. The apparatus of claim 145, wherein said plurality of EMG parameters are selected from the group consisting of: normalized amplitude (mrEMG), normalized mean power (nPWR), zero-crossing average (ZC), median frequency (MF), mean power frequency (MPF), Expected Zero Crossing (EZC), power variance (PVAR), turns (NT) and Complexity (Cmplx).

182. The apparatus of claim 145, wherein said REM determinator is programmed to define the REM period by a plurality of epochs, each characterized by at least one of said plurality of EMG parameters which is below a predetermined threshold.

183. The apparatus of claim 145, wherein said Stage-2 determinator is programmed to define said at least one Stage-2 period by a plurality of epochs, each associated to a cardiac R-R interval corresponding to a K-complex.

184. The apparatus of claim 183, wherein said cardiac R-R interval corresponding to said K-complex is characterized by a specific width and a specific depth.

185. A system for determining a Slow-Wave-Sleep (SWS) period and a Non-SWS (NSWS) period of a sleeping subject, the system comprising:
an apparatus for providing signals of electrical activity of a chest of the sleeping subject, measured over a plurality of epochs;
an R-R extractor for extracting a series of cardiac R-R intervals from the signals;
a decomposer for obtaining a time-frequency decomposition from said series of cardiac R-R intervals; and
an SWS determinator, for using said time-frequency decomposition so as to determine a SWS period defined over a plurality of SWS epochs, thereby also determining NSWS period defined by all epochs other than said SWS epochs, said NSWS period encompassing at least one Rapid-Eye-Movement (REM) sleep period and at least one Non-REM (NREM) sleep period;
thereby to determine the SWS period and the NSWS period of the sleeping subject.

186. The system of claim 185, wherein said apparatus for providing signals is an electrocardiogram (ECG) apparatus.

187. The system of claim 185, wherein said apparatus for providing signals comprises a single lead, adapted for attachment to a predetermined location on the chest of the sleeping subject, said predetermined location is selected so as to substantially optimize said signals.

188. The system of claim 185, wherein said apparatus for providing signals comprises cardiac electrodes, adapted for attachment to a plurality of predetermined locations on the chest of the sleeping subject, said plurality of predetermined locations are selected so as to substantially optimize said signals.

189. The system of claim 188, wherein each of said plurality of predetermined locations is adjacent to a different muscle.

190. The system of claim 188, wherein at least two of said plurality of predetermined locations are adjacent to the same muscle.

191. The system of claim 185, wherein said decomposer is operable to calculate, for each epoch, at least one time-dependent power spectrum component selected from the group consisting of a very-low-frequency (VLF) power spectrum, a low-frequency (LF) power spectrum and a high-frequency (HF) power spectrum.

192. The system of claim 191, wherein said SWS determinator is programmed to define the SWS period by a plurality of epochs, each characterized by at least one power parameter which is below a predetermined threshold, said at least one power parameter is selected from the group consisting of said VLF power spectrum, said LF power spectrum, said HF power spectrum, and a combination between two of said VLF, said LF and said HF power spectra.

193. The system of claim 192, wherein said combination is a ratio.

194. The system of claim 191, wherein said predetermined threshold is constant.

195. The system of claim 191, wherein said predetermined threshold is a first function of an average value of said at least one power parameter.

196. The system of claim 195, wherein said first function is a linear function.

197. The system of claim 191, wherein said predetermined threshold varies with time.

198. The system of claim 191, wherein said decomposer is operable to calculate said VLF, said LF and said HF power spectra within a window along said series of cardiac R-R intervals, said window being characterized by a duration which is a function of a respective frequency.

199. The system of claim 198, wherein said function of said respective frequency is inversely related to said respective frequency.

200. The system of claim 198, wherein said window has an aperture selected from the group consisting of: a rectangular aperture, a Hamming aperture, a Hanning aperture, a Blackman aperture, a Gaussian window, a Lorentzian window, a sinc window, a power of a sine window and a power of a cosine window.

201. The system of claim 198, wherein said decomposer comprises a wavelet processor.

202. The system of claim 201, wherein said wavelet processor is selected from the group consisting of a discrete wavelet processor and a continuous wavelet processor.

203. The system of claim 198, wherein said decomposer comprises a selective discrete spectral processor.

204. The system of claim 203, wherein said decomposer further comprises a spectral transform selector for selecting a transform from the group consisting of: a Fourier transform, a Haar transform, a Hartley transform, a sine transform, a cosine transform, and a Hadamard transform.

205. A system for determining a Rapid-Eye-Movement (REM) sleep and a Non-REM (NREM) sleep of a sleeping subject, the system comprising:
- an apparatus for providing signals of electrical activity of a chest of the sleeping subject, measured over a plurality of epochs;
- an electromyogram (EMG) extractor for extracting a plurality of EMG parameters from the signals; and
- a REM determinator for using said plurality of EMG parameters to determine the REM sleep and the NREM sleep of the sleeping subject.

206. The system of claim 205, wherein said apparatus for providing signals is an electrocardiogram (ECG) apparatus.

207. The system of claim 205, wherein said apparatus for providing signals comprises a single lead, adapted for attachment to a predetermined location on the chest of the sleeping subject, said predetermined location is selected so as to substantially optimize heart-beat reads from said signals and to substantially optimize EMG reads from said signals.

208. The system of claim 205, wherein said apparatus for providing signals comprises cardiac electrodes, adapted for attachment to a plurality of predetermined locations on the chest of the sleeping subject, said plurality of predetermined locations are selected so as to substantially optimize heart-beat reads from said signals and to substantially optimize EMG reads from said signals.

209. The system of claim 208, wherein each of said plurality of predetermined locations is adjacent to a different muscle.

210. The system of claim 208, wherein at least two of said plurality of predetermined locations are adjacent to the same muscle.

211. The system of claim 205, wherein said EMG extractor comprises an eliminator for eliminating at least one signal selected from the group consisting of: a P wave, a T wave and a QRS-complex.

212. The system of claim 211, wherein said eliminator comprises at least one high pass filter for filtering out said P wave and said T wave.

213. The system of claim 212, wherein said high pass filter is characterized by a threshold frequency of about 10 Hz.

214. The system of claim 211, wherein said eliminator is operable comprises to eliminate said QRS-complex by a combination of gating and/or subtraction.

215. The system of claim 205, wherein said plurality of EMG parameters are selected from the group consisting of: normalized amplitude (mrEMG), normalized mean power (nPWR), zero-crossing average (ZC), median frequency (MF), mean power frequency (MPF), Expected Zero Crossing (EZC), power variance (PVAR), turns (NT) and Complexity (Cmplx).

216. The system of claim 215, wherein said REM determinator is programmed to define the REM period by a plurality of epochs, each characterized by at least one of said plurality of EMG parameters which is below a predetermined threshold.

217. A system for determining a Rapid-Eye-Movement (REM) sleep and a Non-REM (NREM) sleep of a sleeping subject, the system comprising:
- an apparatus for providing signals of electrical activity of a chest of the sleeping subject, measured over a plurality of epochs;
- an R-R extractor, for extracting a series of cardiac R-R intervals from the signals;
- a plotter, for constructing a Poincare plot of said series of cardiac R-R intervals; and
- a REM determinator, for using said Poincare plot to determine the REM sleep and the NREM sleep of the sleeping subject.

218. The system of claim 217, wherein said apparatus for providing signals is an electrocardiogram (ECG) apparatus.

219. The system of claim 217, wherein said apparatus for providing signals comprises a single lead, adapted for attachment to a predetermined location on the chest of the sleeping subject, said predetermined location is selected so as to substantially optimize heart-beat reads from said signals.

220. The system of claim 217, wherein said apparatus for providing signals comprises cardiac electrodes, adapted for attachment to a plurality of predetermined locations on the chest of the sleeping subject, said plurality of predetermined locations are selected so as to substantially optimize heart-beat reads from said signals.

221. The system of claim 220, wherein each of said plurality of predetermined locations is adjacent to a different muscle.

222. The system of claim 220, wherein at least two of said plurality of predetermined locations are adjacent to the same muscle.

223. The system of claim 217, further comprising electronic-calculating functionality for calculating a plurality of moments with respect to a predetermined line along said Poincare plot, each of said plurality of moments being calculated within a predetermined time-window.

224. The system of claim 223, wherein said plurality of moments is a plurality of moments of inertia.

225. The system of claim 223, wherein said REM determinator is programmed to define the REM period by a plurality of epochs, each characterized by a moment which is below a predetermined threshold.

226. The system of claim 223, wherein said predetermined line along said Poincare plot is a straight line, forming a predetermined angle with respect to an axis of said Poincare plot.

227. The system of claim 226, wherein said predetermined angle equals about 45 degrees.

228. The system of claim 223, further comprising electronic-calculating functionality for normalizing each of said plurality of moments.

229. A system for determining sleep stages of a sleeping subject, the system comprising:
- an apparatus for providing signals of electrical activity of a chest of the sleeping subject, measured over a plurality of epochs;
- an R-R extractor for extracting a series of cardiac R-R intervals from the signals;
- a decomposer, for obtaining a time-frequency decomposition from said series of cardiac R-R intervals;
- a Slow-Wave-Sleep (SWS) determinator for using said time-frequency decomposition to determine at least one SWS period and at least one Non-SWS (NSWS) period;
- a sleep-onset (SO) determinator for determining at least one SO period onset period from said at least one NSWS period;
- a non-sleep determinator for determining a plurality of non-sleep periods from said at least one NSWS period;
- an electromyogram (EMG) extractor, for extracting a plurality of EMG parameters from a portion of the signals, said portion corresponds to a NSWS period other than said at least one SO period and other than said plurality of non-sleep period;
- a Rapid-Eye-Movement (REM) determinator for using said plurality of EMG parameters to determine at least one REM period, thereby to obtain also at least one LS period defined as a NSWS period other than said at least one SO period, other than said plurality of non-sleep periods and other than said at least one REM period;

thereby to determine the sleep stages of the sleeping subject.

230. The system of claim 229, wherein said apparatus for providing signals is an electrocardiogram (ECG) apparatus.

231. The system of claim 229, wherein said apparatus for providing signals comprises cardiac electrodes, adapted for attachment to a plurality of predetermined locations on the chest of the sleeping subject, said plurality of predetermined locations are selected so as to substantially optimize heartbeat reads from said signals and to substantially optimize EMG reads from said signals.

232. The system of claim 229, further comprising a Stage-2 determinator for determining, from said at least one LS period, at least one Stage-2 period, thereby to obtain also a Stage-1 period, said Stage-1 period being defined as a LS period other than at least one Stage-2 period.

233. The system of claim 229, wherein said decomposer is operable to calculate, for each epoch, at least one time-dependent power spectrum component selected from the group consisting of a very-low-frequency (VLF) power spectrum, a low-frequency (LF) power spectrum and a high-frequency (HF) power spectrum.

234. The system of claim 233, wherein said SWS determinator is programmed to define the SWS period by a plurality of epochs, each characterized by at least one power parameter which is below a predetermined threshold, said at least one power parameter is selected from the group consisting of said VLF power spectrum, said LF power spectrum, said HF power spectrum, and a combination between two of said VLF, said LF and said HF power spectra.

235. The system of claim 234, wherein said combination is a ratio.

236. The system of claim 233, wherein said predetermined threshold is constant.

237. The system of claim 233, wherein said predetermined threshold is a first function of an average value of said at least one power parameter.

238. The system of claim 237, wherein said first function is a linear function.

239. The system of claim 233, wherein said predetermined threshold varies with time.

240. The system of claim 233, wherein said decomposer is operable to calculate said VLF, said LF and said HF power spectra within a window along said series of cardiac R-R intervals, said window being characterized by a duration which is a function of a respective frequency.

241. The system of claim 240, wherein said function of said respective frequency is inversely related to said respective frequency.

242. The system of claim 240, wherein said window has an aperture selected from the group consisting of: a rectangular aperture, a Hamming aperture, a Hanning aperture, a Blackman aperture, a Gaussian window, a Lorentzian window, a sinc window, a power of a sine window and a power of a cosine window.

243. The system of claim 240, wherein said decomposer comprises a wavelet processor.

244. The system of claim 243, wherein said wavelet processor is selected from the group consisting of a discrete wavelet processor and a continuous wavelet processor.

245. The system of claim 240, wherein said decomposer comprises a selective discrete spectral processor.

246. The system of claim 245, wherein said decomposer further comprises a spectral transform selector for selecting a transform from the group consisting of: a Fourier transform, a Haar transform, a Hartley transform, a sine transform, a cosine transform, and a Hadamard transform.

247. The system of claim 233, wherein said SO determinator comprises electronic-calculating functionality for calculating at least one SO parameter and for defining the SO period to be at least one epoch being characterized by at least one SO parameter which is above a predetermined threshold, over a predetermined time range.

248. The system of claim 247, wherein said predetermined time range is from 2 epochs to 10 epochs.

249. The system of claim 247, wherein said at least one SO parameter comprises at least one integrated power spectrum calculated by integrating at least one of said power spectra over predetermined frequency limits.

250. The system of claim 249, wherein said at least one SO parameter further comprises at least one time-dependent power ratio calculated using said at least one integrated power spectrum.

251. The system of claim 249, wherein said SO determinator further comprises electronic-calculating functionality for calculating said predetermined frequency limits.

252. The system of claim 247, further comprising electronic-calculating functionality for normalizing said at least one SO parameter.

253. The system of claim 247, further comprising a statistical analyzer for analyzing said at least one SO parameter using a plurality of statistical quantities.

254. The system of claim 253, wherein said plurality of statistical quantities selected from the group consisting of an average, a variance and a t-test.

255. The system of claim 229, wherein said plurality of non-sleep periods comprises at least one awakening period and/or at least one arousal period.

256. The system of claim 255, wherein said non-sleep determinator comprises:

(a) a low-pass filter for filtering said series of cardiac R-R intervals, thereby to provide a first series of signals; and (b) an awakening period definer for defining said at least one awakening period as a plurality of epochs each associated with at least one of said first series of signals which is below a predetermined threshold.

257. The system of claim 256, wherein said low-pass-filter is at about 0.01 Hz.

258. The system of claim 256, wherein said predetermined threshold is about 0.85 of an averaged value of said first series of signals.

259. The system of claim 255, wherein said non-sleep determinator comprises:

(a) a band-pass-filter for filtering said series of cardiac R-R intervals, thereby providing a second series of signals; and (b) an arousal period definer for defining said at least one arousal period as a plurality of epochs each associated with at least one of said second series of signals which is below a predetermined threshold.

260. The system of claim 259, wherein said band-pass-filter is characterized by a lower band limit of about 0.05 Hz and an upper band limit of about 0.2 Hz.

261. The system of claim 259, wherein said predetermined threshold is about 0.85 of an averaged value of said second series of signals.

262. The system of claim 255, wherein said predetermined profile is characterized by a specific width and a specific depth.

263. The system of claim 229, wherein said EMG extractor comprises an eliminator for eliminating at least one signal selected from the group consisting of: a P wave, a T wave and a QRS-complex.

264. The system of claim 263, wherein said eliminator comprises at least one high pass filter for filtering out said P wave and said T wave.

265. The system of claim 264, wherein said high pass filter is characterized by a threshold frequency of about 10 Hz.

266. The system of claim 263, wherein said eliminator is operable comprises to eliminate said QRS-complex by a combination of gating and/or subtraction.

267. The system of claim 229, wherein said plurality of EMG parameters are selected from the group consisting of: normalized amplitude (mrEMG), normalized mean power (nPWR), zero-crossing average (ZC), median frequency (MF), mean power frequency (MPF), Expected Zero Crossing (EZC), power variance (PVAR), turns (NT) and Complexity (Cmplx).

268. The system of claim 229, wherein said REM determinator is programmed to define the REM period by a plurality of epochs, each characterized by at least one of said plurality of EMG parameters which is below a predetermined threshold.

269. The system of claim 229, wherein said Stage-2 determinator is programmed to define said at least one Stage-2 period by a plurality of epochs, each associated to a cardiac R-R interval corresponding to a K-complex.

270. The system of claim 269, wherein said cardiac R-R interval corresponding to said K-complex is characterized by a specific width and a specific depth.

271. An apparatus for determining a body position or a change in the body position from signals of electrical activity recorded of a chest of a sleeping subject, the signals being QRS complexes, the apparatus comprising:
an R-wave duration (RWD) extractor for extracting R-wave durations from the QRS complexes, thereby to obtain an R-wave duration function
a body position determinator for determining the body position or the change in the body position of the sleeping subject using said RWD function.

272. The apparatus of claim 271, wherein said RWD extractor is operable to define the change in the body position when a change of said RWD function is above a predetermined threshold.

273. The apparatus of claim 272, wherein said predetermined threshold is a standard deviation of said RWD function.

274. The apparatus of claim 272, wherein said body position determinator is operable to calculate at least one local average of said RWD function.

275. The apparatus of claim 272, wherein said body position determinator is operable to calculate a difference between two local averages of said RWD function.

276. The apparatus of claim 271, wherein the body position is one of two body positions.

277. The apparatus of claim 276, wherein said body position determinator is operable to define a first body position, when a value of said RWD function is high and a second body position, when a value of said RWD function is low.

278. The apparatus of claim 271, further comprising a segment calculator for defining at least two segments of each of the QRS complexes and determining width of each of said at least two segments, thereby to obtain, for each QRS complex, a set of widths, said set being representative of the body position.

279. The apparatus of claim 278, wherein said segment calculator is operable to calculate nth-order derivatives of R-waves of said QRS complex, where n is a positive integer, and further wherein said segment calculator is operable to locate zeros of said nth-order derivatives.

280. The apparatus of claim 271, wherein said at least two segments comprise a left segment and a right segment and the body position is one of four body positions.

281. The apparatus of claim 280, wherein said body position determinator is operable to define:
a first body position, when a value of said left segment is high and a value of said right segment is high;
a second body position, when a value of said left segment is low and a value of said right segment is high;
a third body position, when a value of said left segment is high and a value of said right segment is low; and
a fourth body position, when a value of said left segment is low and a value of said right segment is low.

282. An apparatus for determining a sleep apnea from signals of electrical activity recorded of a chest of a sleeping subject, the signals being measured over a plurality of epochs, the apparatus comprising:
an R-R extractor for extracting a series of cardiac R-R intervals from the signals;
a non-sleep determinator for determining awakening periods of the sleeping subject and excluding cardiac R-R intervals corresponding to said awakening periods from said series of cardiac R-R intervals;
a decomposer for calculating a power spectrum from said series of cardiac R-R intervals; and
a sleep apnea determinator for using said power spectrum and determining the sleep apnea of the sleeping subject.

283. The apparatus of claim 282, further comprising a body positions determinator for determining body positions or a change in a body position of the sleeping subject.

284. The apparatus of claim 282, wherein said non-sleep determinator comprises:
(a) a low-pass filter for filtering said series of cardiac R-R intervals, thereby to provide a first series of signals; and
(b) an awakening period definer for defining said at least one awakening period as a plurality of epochs each associated with at least one of said first series of signals which is below a predetermined threshold.

285. The apparatus of claim 284, wherein said low-pass-filter is at about 0.01 Hz.

286. The apparatus of claim 284, wherein said predetermined threshold is about 0.85 of an averaged value of said first series of signals.

287. The apparatus of claim 282, further comprising a discrete transformer for obtaining said power spectrum.

288. The apparatus of claim 287, wherein said discrete transformer is selected from the group consisting of a steady state discrete transformer and a time-dependent discrete transformer.

289. The apparatus of claim 287, wherein said discrete transformer is operable to perform a transform selected from the group consisting of a discrete Fourier transform, a discrete Hartley transform, a discrete sine transform, a discrete cosine transform, a discrete Hadamard transform, a discrete Haar transform and a discrete wavelet transform.

290. The apparatus of claim 282, wherein said sleep apnea determinator is operable to obtain a power spectrum component of said power spectrum, and to identify sleep apnea if said power spectrum component is above a predetermined threshold.

291. The apparatus of claim 290, wherein said power spectrum component is power of signals being at a frequency range representing sleep apnea.

292. The apparatus of claim 291, wherein said frequency range is from about 0.01 Hz to about 0.04 Hz.

293. The apparatus of claim 290, wherein said predetermined threshold is about half of a total power of said power spectrum.

294. The apparatus of claim 283, further comprising a pattern recognition functionality for identifying representative patterns of sleep apnea.

295. The apparatus of claim 294, wherein said representative patterns are characterized by a U-shape of said cardiac R-R intervals.

296. A system for determining a body position or a change in the body position of a sleeping subject, the system comprising:
an apparatus for providing signals of electrical activity of a chest of the sleeping subject, characterized by QRS complexes;
an R-wave duration (RWD) extractor for extracting R-wave durations from the QRS complexes, thereby to obtain an R-wave duration function
a body position determinator for determining the body position or the change in the body position of the sleeping subject using said RWD function.

297. The system of claim 296, wherein said RWD extractor is operable to define the change in the body position when a change of said RWD function is above a predetermined threshold.

298. The system of claim 297, wherein said predetermined threshold is a standard deviation of said RWD function.

299. The system of claim 297, wherein said body position determinator is operable to calculate at least one local average of said RWD function.

300. The system of claim 297, wherein said body position determinator is operable to calculate a difference between two local averages of said RWD function.

301. The system of claim 296, wherein the body position is one of two body positions.

302. The system of claim 301, wherein said body position determinator is operable to define a first body position, when a value of said RWD function is high and a second body position, when a value of said RWD function is low.

303. The system of claim 296, further comprising a segment calculator for defining at least two segments of each of the QRS complexes and determining width of each of said at least two segments, thereby to obtain, for each QRS complex, a set of widths, said set being representative of the body position.

304. The system of claim 303, wherein said segment calculator is operable to calculate nth-order derivatives of R-waves of said QRS complex, where n is a positive integer, and further wherein said segment calculator is operable to locate zeros of said nth-order derivatives.

305. The system of claim 296, wherein said at least two segments comprise a left segment and a right segment and the body position is one of four body positions.

306. The system of claim 305, wherein said body position determinator is operable to define:
a first body position, when a value of said left segment is high and a value of said right segment is high;
a second body position, when a value of said left segment is low and a value of said right segment is high;
a third body position, when a value of said left segment is high and a value of said right segment is low; and
a fourth body position, when a value of said left segment is low and a value of said right segment is low.

307. A system for determining a sleep apnea of a sleeping subject, the system comprising:
an apparatus for providing signals of electrical activity of a chest of the sleeping subject, measured over a plurality of epochs;
an R-R extractor for extracting a series of cardiac R-R intervals from the signals;
a non-sleep determinator for determining awakening periods of the sleeping subject and excluding cardiac R-R intervals corresponding to said awakening periods from said series of cardiac R-R intervals;
a decomposer for calculating a power spectrum from said series of cardiac R-R intervals; and
a sleep apnea determinator for using said power spectrum and determining the sleep apnea of the sleeping subject.

308. The system of claim 307, further comprising a body positions determinator for determining body positions or a change in a body position of the sleeping subject.

309. The system of claim 307, wherein said non-sleep determinator comprises:
(a) a low-pass filter for filtering said series of cardiac R-R intervals, thereby to provide a first series of signals; and
(b) an awakening period definer for defining said at least one awakening period as a plurality of epochs each associated with at least one of said first series of signals which is below a predetermined threshold.

310. The system of claim 309, wherein said low-pass-filter is at about 0.01 Hz.

311. The system of claim 309, wherein said predetermined threshold is about 0.85 of an averaged value of said first series of signals.

312. The system of claim 307, further comprising a discrete transformer for obtaining said power spectrum.

313. The system of claim 312, wherein said discrete transformer is selected from the group consisting of a steady state discrete transformer and a time-dependent discrete transformer.

314. The system of claim 312, wherein said discrete transformer is operable to perform a transform selected from the group consisting of a discrete Fourier transform, a discrete Hartley transform, a discrete sine transform, a discrete cosine transform, a discrete Hadamard transform, a discrete Haar transform and a discrete wavelet transform.

315. The system of claim 307, wherein said sleep apnea determinator is operable to obtain a power spectrum component of said power spectrum, and to identify sleep apnea if said power spectrum component is above a predetermined threshold.

316. The system of claim 315, wherein said power spectrum component is power of signals being at a frequency range representing sleep apnea.

317. The system of claim 316, wherein said frequency range is from about 0.01 Hz to about 0.04 Hz.

318. The system of claim 315, wherein said predetermined threshold is about half of a total power of said power spectrum.

319. The system of claim 308, further comprising a pattern recognition functionality for identifying representative patterns of sleep apnea.

320. The system of claim 319, wherein said representative patterns are characterized by a U-shape of said cardiac R-R intervals.

321. A method of determining sleep stages from signals of electrical activity recorded of a chest of a sleeping subject, the signals being measured over a plurality of epochs, the method comprising:

extracting a series of cardiac R-R intervals from the signals and obtaining a time-frequency decomposition from said series of cardiac R-R intervals;

using said time-frequency decomposition to determine at least one Slow-Wave-Sleep (SWS) period and at least one Non-SWS (NSWS) period;

constructing a Poincare plot of at least a portion of said series of cardiac R-R intervals, and using said Poincare plot and said time-frequency decomposition for determining at least one REM period, thereby obtaining also at least one light-sleep (LS) period defined as a NSWS period other than said at least one SO period, other than said plurality of non-sleep periods and other than said at least one REM period;

thereby determining the sleep stages of the sleeping subject.

322. The method of claim 321, further comprising calculating a plurality of moments with respect to a predetermined line along said Poincare plot, each of said plurality of moments being calculated within a predetermined time-window.

323. The method of claim 322, wherein the REM sleep is defined by a plurality of epochs, each characterized by a moment which is below a predetermined threshold.

324. The method of claim 321, further comprising determining, from said at least one LS period, at least one Stage-2 period thereby obtaining also a Stage-1 period, said Stage-1 period being defined as a LS period other than said at least one Stage-2.

325. The method of claim 321, wherein said obtaining said time-frequency decomposition comprises calculating, for each epoch, at least one time-dependent power spectrum component selected from the group consisting of a very-low-frequency (VLF) power spectrum, a low-frequency (LF) power spectrum and a high-frequency (HF) power spectrum.

326. The method of claim 325, wherein the SWS period is defined by a plurality of epochs, each characterized by at least one power parameter which is below a predetermined threshold, said at least one power parameter is selected from the group consisting of said VLF power spectrum, said LF power spectrum, said HF power spectrum, and a combination between two of said VLF, said LF and said HF power spectra.

327. The method of claim 325, wherein said determining at least one SO period comprises calculating at least one SO parameter and defining the SO period to be at least one epoch being characterized by at least one SO parameter which is above a predetermined threshold, over a predetermined time range.

328. The method of claim 327, wherein said at least one SO parameter comprises at least one integrated power spectrum calculated by integrating at least one of said power spectra over predetermined frequency limits.

329. The method of claim 328, wherein said at least one SO parameter further comprises at least one time-dependent power ratio calculated using said at least one integrated power spectrum.

330. The method of claim 321, wherein said plurality of non-sleep periods comprises at least one awakening period and/or at least one arousal period.

331. The method of claim 330, further comprising:
(a) filtering said series of cardiac R-R intervals using a low-pass-filter, thereby providing a first series of signals; and
(b) defining said at least one awakening period as a plurality of epochs each associated with at least one of said first series of signals which is below a predetermined threshold.

332. The method of claim 330, further comprising:
(a) filtering said series of cardiac R-R intervals using a band-pass-filter, thereby providing a second series of signals; and
(b) defining said at least one arousal period as a plurality of epochs each associated with at least one of said second series of signals which is below a predetermined threshold.

333. The method of claim 321, wherein said at least one Stage-2 period is defined by a plurality of epochs, each associated to a cardiac R-R interval corresponding to a K-complex.

* * * * *